US00RE45992E

(19) United States
(12) Reissued Patent
Behrens et al.

(10) Patent Number: US RE45,992 E
(45) Date of Reissued Patent: May 3, 2016

(54) OPTIMIZED FC VARIANTS

(71) Applicant: LABORATOIRE FRANCAIS DU FRACTIONNEMENT ET DES BIOTECHNOLOGIES, Les Ulis (FR)

(72) Inventors: Christian Behrens, Palaiseau (FR); Sylvie Jorieux, Villeneuve D'Ascq (FR); Abdelhakim Kharrat, Montgiscard (FR); Khalil Bouayadi, Ramonville Saint Agne (FR); Philippe Mondon, Donneville (FR); Celine Monnet-Mars, Blagnac (FR)

(73) Assignee: LABORATOIRE FRANCAIS DU FRACTIONNEMENT ET DES BIOTECHNOLOGIES, Les Ulis (FR)

(21) Appl. No.: 14/338,413

(22) Filed: Jul. 23, 2014

Related U.S. Patent Documents

Reissue of:
(64) Patent No.: 8,742,074
Issued: Jun. 3, 2014
Appl. No.: 13/257,502
PCT Filed: Mar. 19, 2010
PCT No.: PCT/EP2010/053644
§ 371 (c)(1),
(2) Date: Sep. 19, 2011
PCT Pub. No.: WO2010/106180
PCT Pub. Date: Sep. 23, 2010

(30) Foreign Application Priority Data

Mar. 20, 2009 (EP) ..... 09305250

(51) Int. Cl.

| | |
|---|---|
| ***C07K 16/00*** | (2006.01) |
| ***C07H 21/04*** | (2006.01) |
| ***C12N 15/00*** | (2006.01) |
| ***C12N 5/00*** | (2006.01) |
| ***C12N 1/20*** | (2006.01) |
| ***C12P 21/04*** | (2006.01) |

(52) U.S. Cl.
CPC ..... *C07K 16/00* (2013.01); *C07K 2317/21* (2013.01); *C07K 2317/52* (2013.01); *C07K 2317/92* (2013.01)

(58) Field of Classification Search
CPC ..... C07K 16/00; C07K 2317/21; C07K 2317/92; C07K 2317/52
USPC ..... 530/387.1; 536/23.53; 435/320.1, 325, 435/69.6, 252.3
See application file for complete search history.

(56) References Cited

U.S. PATENT DOCUMENTS

| | | | | |
|---|---|---|---|---|
| 2007/0148164 | A1* | 6/2007 | Farrington et al. | 424/133.1 |
| 2009/0041770 | A1* | 2/2009 | Chamberlain et al. | 424/134.1 |
| 2010/0098730 | A1* | 4/2010 | Lowman et al. | 424/278.1 |

FOREIGN PATENT DOCUMENTS

WO WO 00/42072 A2 7/2000

OTHER PUBLICATIONS

Shields et al., "High resolution mapping of the binding site on human IgG1 for Fc gamma R, Fc gamma RII, Fc gamma RIII, and FcRn and design of IgG1 variants with improved binding to the Fc gamm R," Journal of Biological Chemistry, vol. 276, No. 9, pp. 6591-6604, Mar. 2, 2001.
Ghetie et al., "Increasing the Serum Persisitence of an IgG Fragment by Random Mutagenesis," Nature Biotechnology, vol. 15, No. 7, pp. 637-640, Jan. 1, 1997.
Medesan et al., "Comparative Studies of Rat IgG to Further Delineate the FC: FCRN Interaction Site," European Journal of Immunology, vol. 28, No. 7, pp. 2092-2100, Jan. 1, 1998.
International Search Report issued in application No. PCT/EP2010/053644 on Oct. 19, 2010.
Office Action issued in U.S. Appl. No. 13/257,502 on Nov. 20, 2012.
Office Action issued in U.S. Appl. No. 13/257,502 on Apr. 16, 2013.
Office Action issued in U.S. Appl. No. 13/257,502 on Sep. 20, 2013.
Notice of Allowance issued in U.S. Appl. No. 13/257,502 on Feb. 5, 2014.
Immunogenetics, "IMGT Repertoire (IG and TR)," obtained from the Internet, http://www.imgt.org/IMGTrepertoire/Proteins/allotypes/human/IGH/IGHC/Glm_allotypes.html, accessed on Sep. 15, 2015.
Magdelaine-Beuzelin et al., "IgG1 heavy chain-coding gene polymorphism (G1m allotypes) and development of antibodies-to-infliximab," Pharmacogenetics and Genomics, vol. 00, No. 00, pp. 1-5, 2009.

* cited by examiner

*Primary Examiner* — Shri Ponnaluri
(74) *Attorney, Agent, or Firm* — Foley & Lardner LLP

(57) ABSTRACT

A variant of a parent polypeptide including an Fc region, which variant exhibits increased binding to FcRn as compared to the parent polypeptide and includes at least one amino acid modification in the Fc region.

10 Claims, 16 Drawing Sheets

```
                                                                  226
                                                                  ↑
IgG1m(1,17)    EPKSCDK--THT-----------------------------------------CPPCPAPEL
IgG1m(3)       EPKSCDK--THT-----------------------------------------CPPCPAPEL
IgG2,          ERKCCVE----------------------------------------------CPPCPAPPV
IgG3           ELKTPLGDTTHTCPRCPEPKSCDTPPPCPRCPEPKSCDTPPPCPRCPEPKSCDTPPPCPRCPAPEL
IgG4           ESKYG-------------------------------------------------PPCPS-PAPEF

IgG1m(1,17)    LGGPSVFLFPPKPKDTLMISRTPEVTCVVVDVSHEDPEVKFNWYVDGVEVHNAKTKPREEQYNSTY
IgG1m(3)       LGGPSVFLFPPKPKDTLMISRTPEVTCVVVDVSHEDPEVKFNWYVDGVEVHNAKTKPREEQYNSTY
IgG2           -AGPSVFLFPPKPKDTLMISRTPEVTCVVVDVSHEDPEVQFNWYVDGVEVHNAKTKPREEQYNSTY
IgG3           LGGPSVFLFPPKPKDTLMISRTPEVTCVVVDVSHEDPEVQFKWYVDGVEVHNAKTKPREEQYNSTF
IG4            LGGPSVFLFPPKPKDTLMISRTPEVTCVVVDVSQEDPEVQFNWYVDGMEVHNAKTKPREEQFNSTF

IgG1m(1,17)    RVVSVLTVLHQDWLNGKEYKCKVSNKALPAPIEKTISKAKGQPREPQVYTLPPSRDELTKNQVSLT
IgG1m(3)       RVVSVLTVLHQDWLNGKEYKCKVSNKALPAPIEKTISKAKGQPREPQVYTLPPSREEMTKNQVSLT
IgG2           RVVSVLTVLHQDWLNGKEYKCKVSNKALPAPIEKTISKTKGQPREPQVYTLPPSREEMTKNQVSLT
IgG3           RVVSVLTVLHQDWLNGKEYKCKVSNKALPAPIEKTISKTKGQPREPQVYTLPPSREEMTKNQVSLT
IgG4           RVVSVLTVVHQDWLNGKEYKCKVSNKGLPAPIEKTISKAKGQPREPQVYTLPPSQEEMTKNQVSLT

IgGm(1,17)     CLVKGFYPSDIAVEWESNGQPENNYKTTPPVLDSDGSFFLYSKLTVDKSRWQQGNVFSCSVMHEAL
Igg1m(3)       CLVKGFYPSDIAVEWESNGQPENNYKTTPPVLDSDGSFFLYSKLTVDKSRWQQGNVFSCSVMHEGL
IgG2           CLVKGFYPSDIAVEWESNGQPENNYKTTPPMLDSDGSFFLYSKLTVDKSRWQQGNVFSCSVMHEAL
IgG3           CLVKGFYPSDIAVEWESSGQPENNYNTTPPMLDSDGSFFLYSKLTVDKSRWQQGNIFSCSVMHEAL
IgG4           CLVKGFYPSDIAVEWESNGQPENNYKTTPPVLDSDGSFFLYSRLTVDKSRWQEGNVFSCSVMHEAL

IgG1m(1,17)    HNHYTQKSLSLSPGK
IgG1m(3)       HNHYTQKSLSLSPGK
IgG2,          HNHYTQKSLSLSPGK
IgG3           HNRFTQKSLSLSPGK
IgG4           HNHYTQKSLSLSLGK
```

FIGURE 6

OPTIMIZED FC VARIANTS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The present invention relates to a variant of a parent polypeptide comprising an Fc region. The said variant exhibits increased binding to FcRn as compared to the parent polypeptide and comprises at least one amino acid modification in its Fc region.

DESCRIPTION OF RELATED ART

Monoclonal antibodies are used as therapeutics, to treat a variety of conditions including cancer, autoimmune diseases, chronic inflammatory diseases, transplant rejection, infectious diseases, and cardiovascular diseases. Currently, they are over twenty monoclonal antibodies or monoclonal antibody fragment products approved on the market, and more than four hundred in clinical development. Despite such acceptance and promise, there remains significant need for optimization of the structural and functional properties of antibodies.

One of the critical issues in the use of monoclonal antibodies in therapy is their persistence in the blood circulation. The rate of antibody clearance directly affects the efficacy of therapy, and consequently, the frequency and the quantity of drug administration that may cause adverse effects in the patient and also increase medical costs.

IgG is the most prevalent immunoglobulin class in humans and also the most utilized in therapeutic. The mechanism of IgG homeostasis has been elucidated through studies related to the transfer of passive immunity from mother to fetus or neonate in rodents (Brambell, 1966, Lancet; 2 (7473):1087-93; Rodewald, 1976, J Cell Biol.; 71 (2):666-9; Jones et al., 1972, J Clin Invest., 51 (11):2916-27). In early studies, Brambell had postulated that there was a receptor for the maternofetal transmission of IgG and that the mechanism involved in maternofetal transfer of IgG and catabolism of IgG may be either the same or, at least, very closely related (Brambell, 1966, Lancet; 2 (7473):1087-93).

Studies have found that the transport of IgG within and across polarized cells is mediated by binding of Fc region to a high-affinity Fc-receptor, named neonatal Fc receptor (FcRn). The FcRn is a heterodimer that comprises a transmembrane α-chain with structural homology to the extracellular domains of the α-chain of major histocompatibility complex class I molecules, and a soluble light chain consisting of $\beta_2$-microglobulin ($\beta_2$m) (Simister and Mostov, 1989, Cold Spring Harb Symp Quant Biol.:54 Pt 1:571-80). In humans, the FcRn is expressed in placental cells, in intestinal, kidney and bronchial epithelial cells, in endothelial cells and in hematopoetic cells such as small intestinal macrophages, monocytes and monocyte-derived dendritic cells (Zhu X et al., 2001, J Immunol.; 166:3266-76). FcRn binds its two major ligands, IgG and serum albumin, in a pH-dependent manner, with efficient binding at pH 6.0-6.5 and releasing at pH 7.0-7.5 (Raghavan et al., 1995, Biochemistry., 34:14649-57).

The mechanism proposed for IgG protection from catabolism is that IgGs are internalized by non-specific pinocytosis into the endosomes of the endothelial cells where the low pH promotes binding to FcRn (Ghetie and Ward, 1997, Nat. Biotechnol., 15: 637-40). Bound IgG-FcRn complexes are recycled back to the cell surface and dissociate at the neutral pH of the extracellular fluid, returning to circulation in the blood. IgGs that do not bind to FcRn traffic into the lysosomes where they are degraded by proteases. According to the concentration-dependent catabolism mechanism for the survival of IgG, at low serum IgG concentrations the receptor would bind all endocytosed IgG, and efficiently return it to the circulation, yielding a long IgG half-life. Conversely, at high IgG concentrations, the receptor is saturated by IgG and a major fraction of the IgG is unbound by the receptor and traffics to be degraded, yielding a more rapid catabolism of the unbound IgG.

Various site-specific mutagenesis experiments in the Fc region of mouse IgGs have led to identification of certain critical amino acid residues involved in the interaction between IgG and FcRn (Kim et al., 1994, Eur J Immunol.; 24:2429-34; Kim et al., 1994, Eur J Immunol; 24:542-8; Medesan et al., 1996, Eur J Immunol.; 26:2533-6; Medesan et al., 1997, J Immunol.; 158: 2211-7). These studies and sequence comparison studies found that isoleucine at position 253, histidine at position 310, and histidine at position 435 (according to Kabat numbering, Kabat et al., Sequences of Proteins of Immunological Interest, 5th Ed. Public Health Service, National Institutes of Health, Bethesda, Md. (1991)), are highly conserved in human and rodent IgGs, suggesting their importance in IgG-FcRn binding. These amino acid residues are located at the CH2-CH3 domains interface and the mapping of the functional site to these residues is consistent with the X-ray crystallographic structure of rat FcRn complexed with rat Fc (Burmeister et al., 1994, Nature; 372 (6504):379-83).

Ghetie et al. (1997, Nat. Biotechnol; 15:637-40) randomly mutagenized position 252, position 254, and position 256 in a mouse IgG1 Fc-hinge fragment. One mutant showed an affinity three and a half times higher for mouse FcRn and a half-life about 23% or 65% longer in two mouse strains, respectively, as compared to that of the wild-type.

Kim et al. (1999, Eur J Immunol; 29:2819-25) mutagenized human IgG1 by amino acid substitutions at position 253, position 310, or position 435 of the Fc region. They found that the mutant Fc-hinge fragments have reduced serum half-lives in mice compared to the wild-type IgG1 Fc-hinge fragment, and concluded that Ile253, His310, and His435 play a central role in regulating the serum half-life of IgG.

Hornick et al. (2000, J Nucl Med., 41:355-62) showed that a single amino acid substitution at position 253 in the Fc region of a chimeric human IgG1 antibody accelerates clearance in mice and improves immunoscintigraphy of solid tumors.

Shields et al. (2001, J Biol Chem; 276:6591-604) used alanine scanning mutagenesis to alter residues in the Fc region of a human IgG1 antibody and then assessed the binding to human FcRn. Positions that effectively abrogated binding to FcRn when changed to alanine include I253, S254, H435, and Y436. Other positions showed a less pronounced reduction in binding as follows: E233-G236, R255, K288, L309, S415, and H433. Several amino acid positions exhibited an improvement in FcRn binding when changed to alanine; notable among these are P238, T256, E272, V305, T307, Q311, D312, K317, D376, E380, E382, S424, and N434. Many other amino acid positions exhibited a slight improvement (D265, N286, V303, K360, Q362, and A378) or no change (S239, K246, K248, D249, M252, E258, T260, S267, H268, S269, D270, K274, N276, Y278, D280, V282, E283, H285, T289, K290, R292, E293, E294, Q295, Y296, N297, S298, R301, N315, E318, K320, K322, S324, K326, A327, P329, P331, E333, K334, T335, S337, K338, K340, Q342, R344, E345, Q345, Q347, R356, M358, T359, K360, N361, Y373, S375, S383, N384, Q386, E388, N389, N390, K392, L398, S400, D401, K414, R416, Q418, Q419, N421, V422, E430, T437, K439, S440, S442, S444, and K447) in FcRn binding.

The most pronounced additivity was found for combination variants with improved binding to FcRn. At pH 6.0, the E380A/N434A variant showed over 8-fold better binding to FcRn, relative to native IgG1, compared with 2-fold for E380A and 3.5-fold for N434A. Adding T307A to this effected a 12-fold improvement in binding relative to native IgG1.

Dall'Acqua et al. (2002, J Immunol.; 169:5171-80) described random mutagenesis and screening of human IgG1 hinge-Fc fragment phage display libraries against mouse FcRn. They disclosed random mutagenesis of positions 251, 252, 254-256, 308, 309, 311, 312, 314, 385-387, 389, 428, 433, 434, and 436. The major improvements in IgG1-human FcRn complex stability occur in substituting residues located in a band across the Fc-FcRn interface (M252, S254, T256, H433, N434, and Y436) and to lesser extend substitutions of residues at the periphery like V308, L309, Q311, G385, Q386, P387, and N389. The variant with the highest affinity to human FcRn was obtained by combining the M252Y/S254T/T256E and H433K/N434F/Y436H mutations and exhibited a 57-fold increase in affinity relative to the wild-type IgG1.

Hinton et al. (2004, J Biol Chem.; 279:6213-6) described two mutations, T250Q and M428L, which increased the binding of human IgG2 to human FcRn by about 3 and 7-fold, respectively. In combination, these two mutations induced a 28-fold increased binding capacity of IgG2. Injected to rhesus monkeys for pharmacokinetics studies, both IgG2 mutants, M428L and T250Q/M428L, showed half-lives about 2-fold longer than the wild-type antibody Dall'Acqua et al. (2006, J. Biol. Chem.; 281:23514-24) described a humanized anti-respiratory syncytial virus IgG1 whose Fc region was mutated at position 252, 254 and 256 (M252Y/S254T/T256E). These mutations increase the binding to human FcRn by about 10-fold at pH 6.0 while allowing efficient release at pH 7.4 (Dall'Acqua et al., 2002, J Immunol.; 169:5171-80). The in vivo behaviour of such a mutated human IgG1 exhibited a nearly 4-fold increase in serum half-life in cynomolgus monkey as compared to wild-type IgG1.

Additionally, various publications describe methods for obtaining physiologically active molecules whose half-lives are modified either by introducing an FcRn-binding polypeptide into the molecules (WO 97/43316; U.S. Pat. No. 5,869,046; U.S. Pat. No. 5,747,035; WO 96/32478; WO 91/14438) or by fusing the molecules with antibodies whose FcRn-binding affinities are preserved but affinities for other Fc receptors have been greatly reduced (WO 99/43713) or fusing with FcRn binding domains of antibodies (WO 00/09560; U.S. Pat. No. 4,703,039).

U.S. Pat. No. 6,165,745 discloses a method of producing an antibody with a decreased biological half-life by introducing a mutation into the DNA segment encoding the antibody. The mutation includes an amino acid substitution at position 253, 310, 311, 433, or 434 of the Fc-hinge domain. The full disclosure of U.S. Pat. No. 6,165,745, as well as the full disclosure of all other U.S. patent references cited herein, are hereby incorporated by reference.

PCT Publication No. WO 00/42072 discloses a polypeptide comprising a variant Fc region with altered FcRn binding affinity, which polypeptide comprises an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 386, 388, 400, 413, 415, 424, 433, 434, 435, 436, 439, and 447 of the Fc region, wherein the numbering of the residues in the Fc region is that of the EU index (Kabat et al., op. cit.).

PCT Publication No. WO 02/060919 A2 discloses a modified IgG comprising an IgG constant domain comprising one or more amino acid modifications relative to a wild-type IgG constant domain, wherein the modified IgG has an increased half-life compared to the half-life of an IgG having the wild-type IgG constant domain, and wherein the one or more amino acid modifications are at one or more of positions 251, 253, 255, 285-290, 308-314, 385-389, and 428-435.

There is still a need in the art for novel optimized Fc variants.

SUMMARY OF THE INVENTION

The present invention provides a variant of a parent polypeptide with optimized properties. The optimized properties comprise higher binding property to FcRn than the corresponding parent polypeptide. In a preferred embodiment, the said variant of a parent polypeptide comprises a Fc region, exhibits increased binding to FcRn as compared to the said parent polypeptide, and comprises at least one amino acid modification in the Fc region of said parent polypeptide, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index as in Kabat.

In another embodiment, the invention provides a pharmaceutical composition comprising the variant of the invention.

In another embodiment, the invention provides an isolated nucleic acid encoding the variant of the invention.

In another embodiment, the invention provides a vector comprising the nucleic acid described above.

In another embodiment, the invention provides a host cell containing a vector described above.

In another embodiment, the invention provides a method for producing a polypeptide variant comprising culturing the host cell described above so that the nucleic acid is expressed.

In another embodiment, the invention provides a medicament comprising a variant of the invention.

In another embodiment, the invention provides the use of a variant of the invention for the manufacture of a medicament.

In another embodiment, the invention provides a method for identifying Fc optimized variants.

CVDE: C-terminal part of the VMA1-derived endonuclease, VMA: vacuolar ATPase subunit (VMA), CPIII: C-terminal part of the capsid protein pIII (or p3) of the phage M13

Figure 2B:
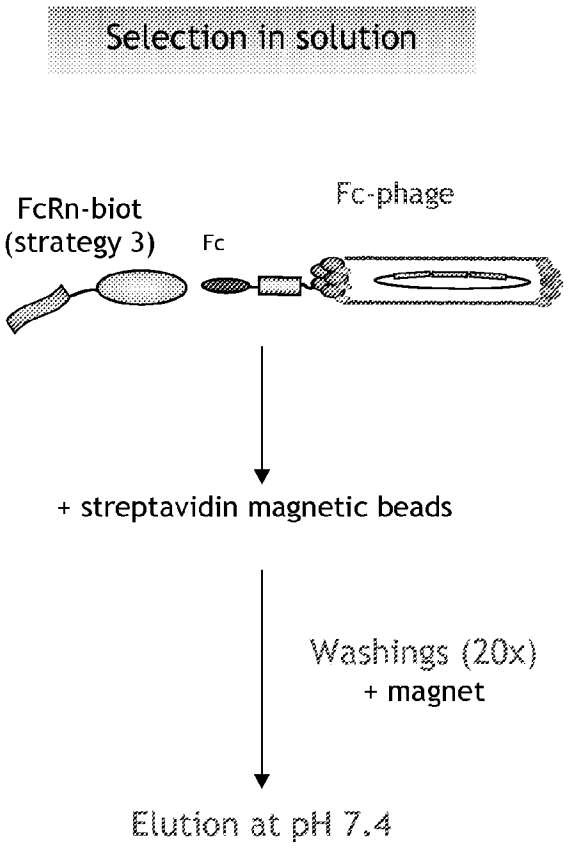
Figure 2A:
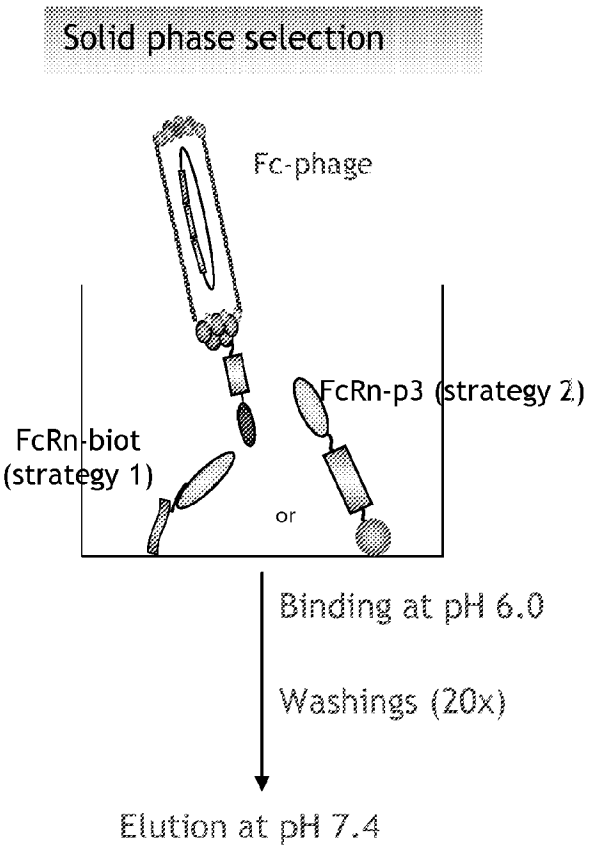

FIG. 2 shows the methods used for Fc variants selection in solid phase (2A) and in solution (2B). FcRn-biot refers to biotinylated FcRn and FcRn-p3 refers to FcRn-p3 fusion protein. The Fc-phage is bacteriophage M13 which expresses an Fc variant on its capsid. In solid phase selection, the wells of immunoplates are coated with FcRn-p3 fusion protein (Fc-Rn-p3) or with neutravidin followed by FcRn-biot.

Figure 3:
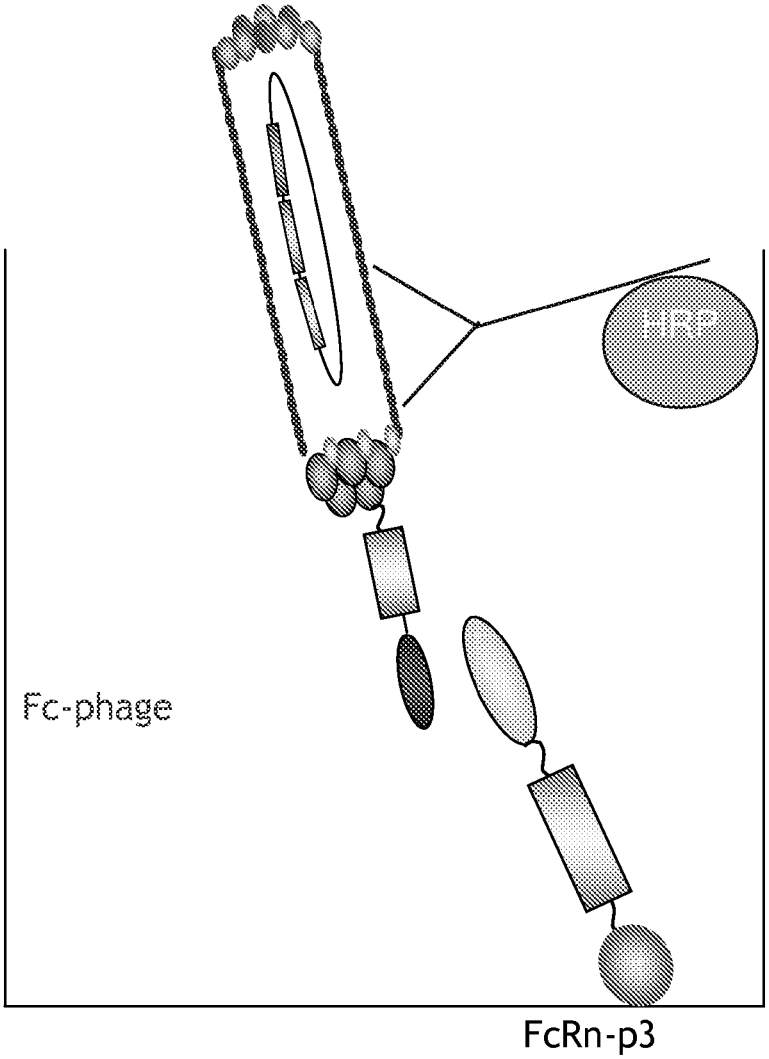

FIG. 3 shows the principle of phage-ELISA assay performed on selected Fc variants. The Fc-phage is a bacteriophage M13 which expresses an Fc variant on its capsid. FcRn-p3 is FcRn-p3 fusion protein coated on wells of immunoplates. Anti-M13 refers to mouse anti-M13 antibody fused to Horseradish peroxidase (HRP) used for ELISA detection.

Figure 4:
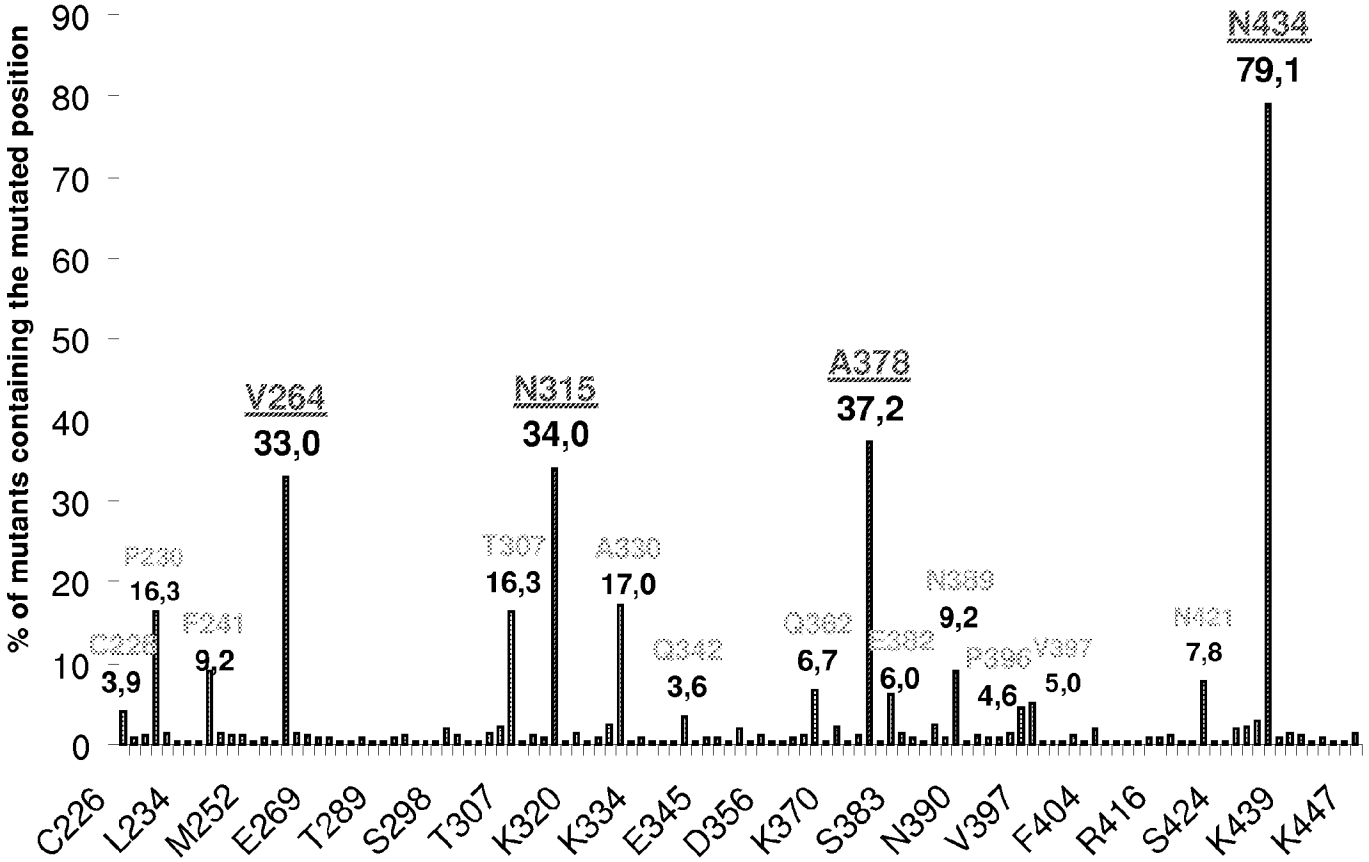

FIG. 4 shows a histogram which represents for each amino acid position of Fc IgG1 the percentage of mutants comprising a modification at said position. X-coordinate: amino acid number according to EU index as in Kabat of the mutated position. Y-coordinate: percentage of Fc variants containing the position mutated.

Figure 5A:
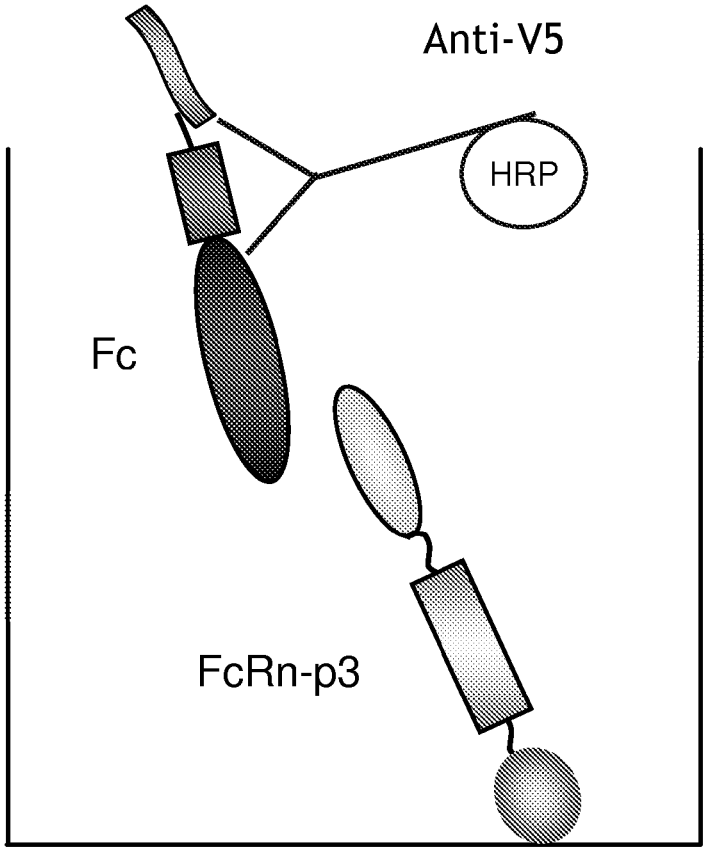

FIG. 5a shows the principle of ELISA assay dedicated to measure the binding affinity of Fc variants for FcRn. FcRn-p3 is an FcRn-p3 fusion protein coated on wells of immunoplates. Fc is an Fc variant comprising V5 tag for ELISA detection. Anti-V5 is an anti-V5 antibody fused to HRP. The antibody is used for ELISA detection.

Figure 5B:
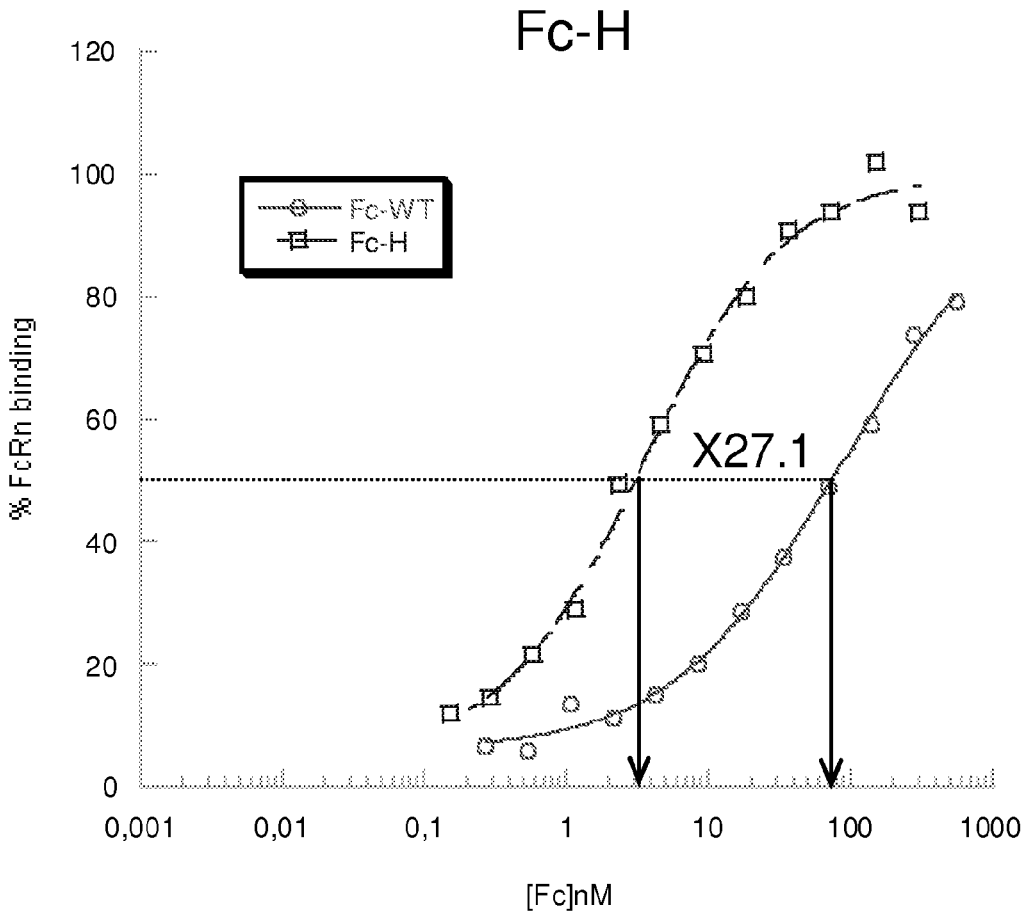

FIG. 5b shows the dose-effect curve for wild-type Fc (rounds) and Fc-H variant (squares) obtained by ELISA assay performed as described in Example 1 in IV.1.a. X-coordinate: Concentration of Fc polypeptide. Y-coordinate: percentage of FcRn bound to Fc polypeptide.

Figure 5C:
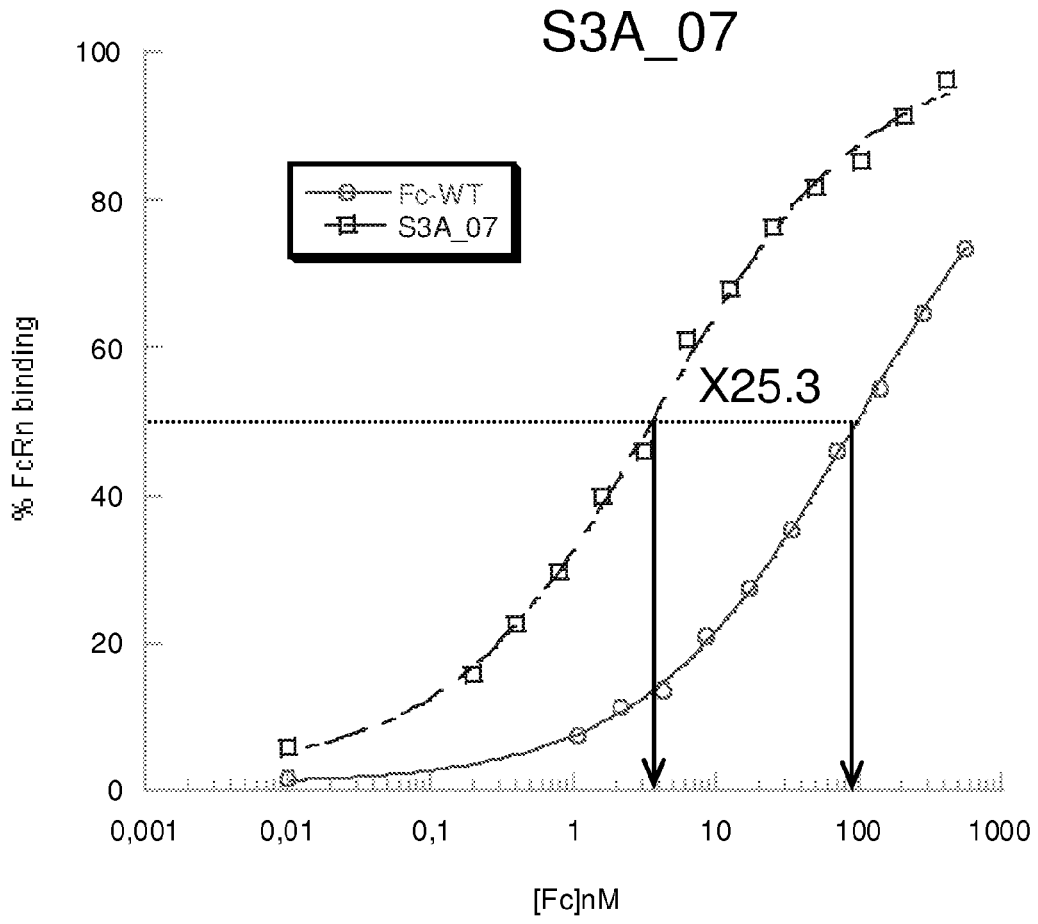

FIG. 5c shows the dose-effect curves for wild-type Fc (rounds) and S3A_07 variant (squares) obtained by ELISA assay performed as described in Example 1 in IV.1.a. X-coordinate: Concentration of Fc polypeptide. Y-coordinate: percentage of FcRn bound to Fc polypeptide.

Figure 5D:
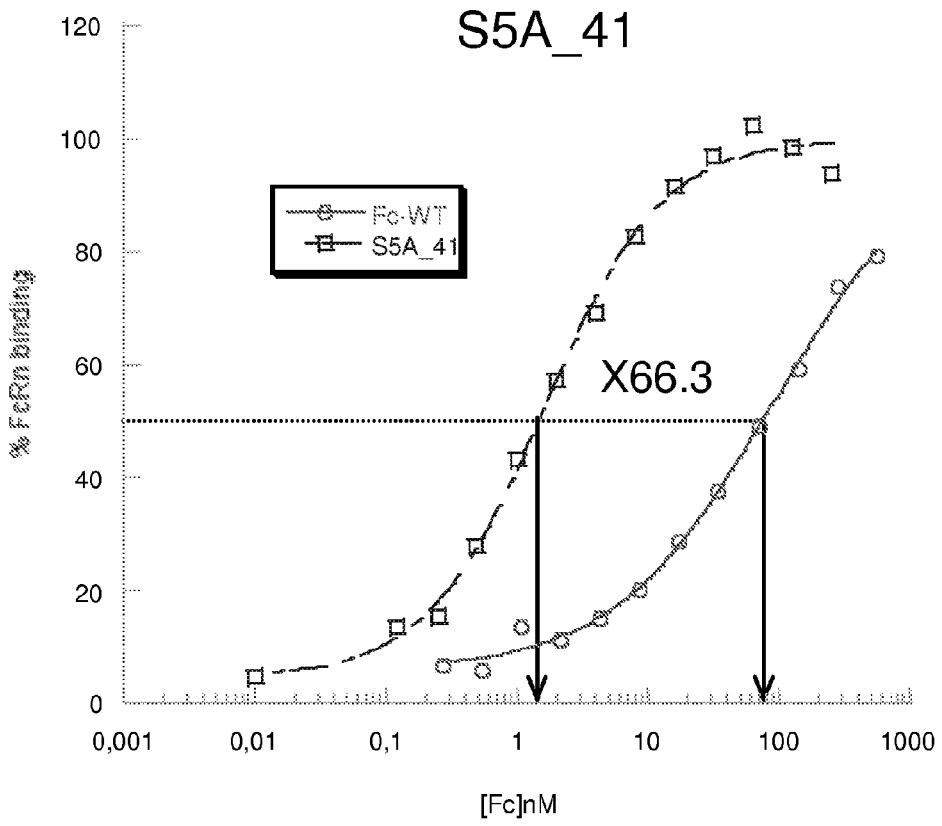

FIG. 5d shows the dose-effect curves for wild-type Fc (rounds) and S5A_41 variant (squares) obtained by ELISA assay performed as described in Example 1 in IV.1.a. X-coordinate: Concentration of Fc polypeptide. Y-coordinate: percentage of FcRn bound to Fc polypeptide.

FIG. 6 shows alignments of native human IgG1 sequences referring to positions 216-447 (according to EU index in Kabat) with the corresponding sequences of human IgG2 (SEQ ID NO:14), human IgG3 (SEQ ID NO:15) and human IgG4 (SEQ ID NO:16). The IgG1 sequences refer to G1m1, 17 allotype (SEQ ID NO:12) and to G1 m3 allotype (SEQ ID NO:13). The "lower hinge-CH2-CH3" domain of IgG1 begins at position 216 (see arrow).

Figure 7:
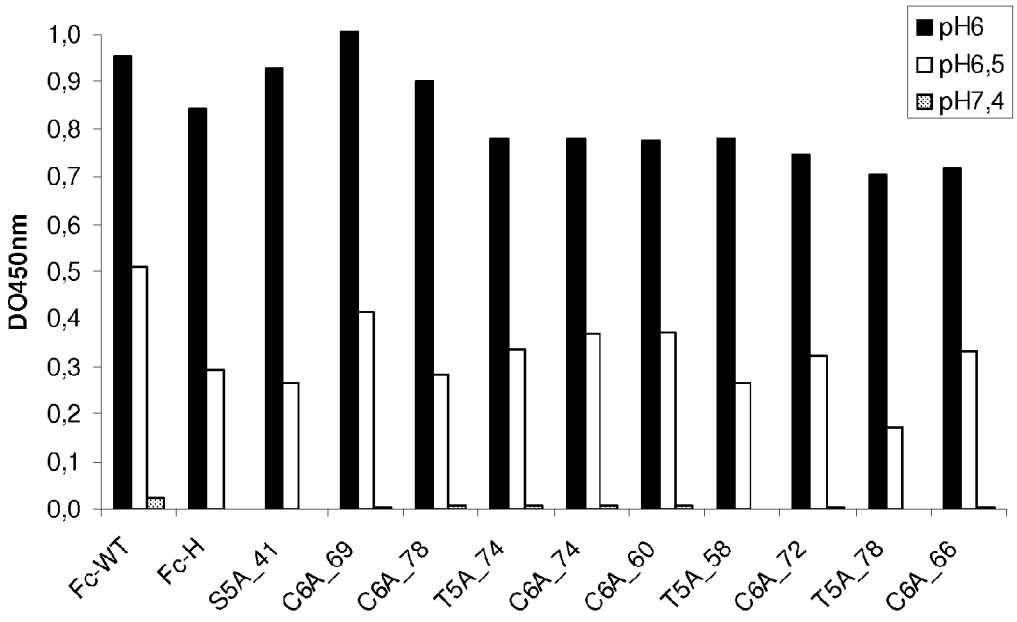

FIG. 7 shows the results of ELISA assays which were performed to show the Fc-variant binding affinity to FcRn at distinct pHs (see for more details Example 2, part IV.2). The histogram represents for each variants the value of $OD_{450nm}$ measured for ELISA assay performed at pH−6 (black bars), at pH=6.5 (white bars) or at pH=7.4 (grey bars). The value of $OD_{450nm}$ correlates with the amount of immobilized FcRn bound to Fc variants.

Figure 8A:
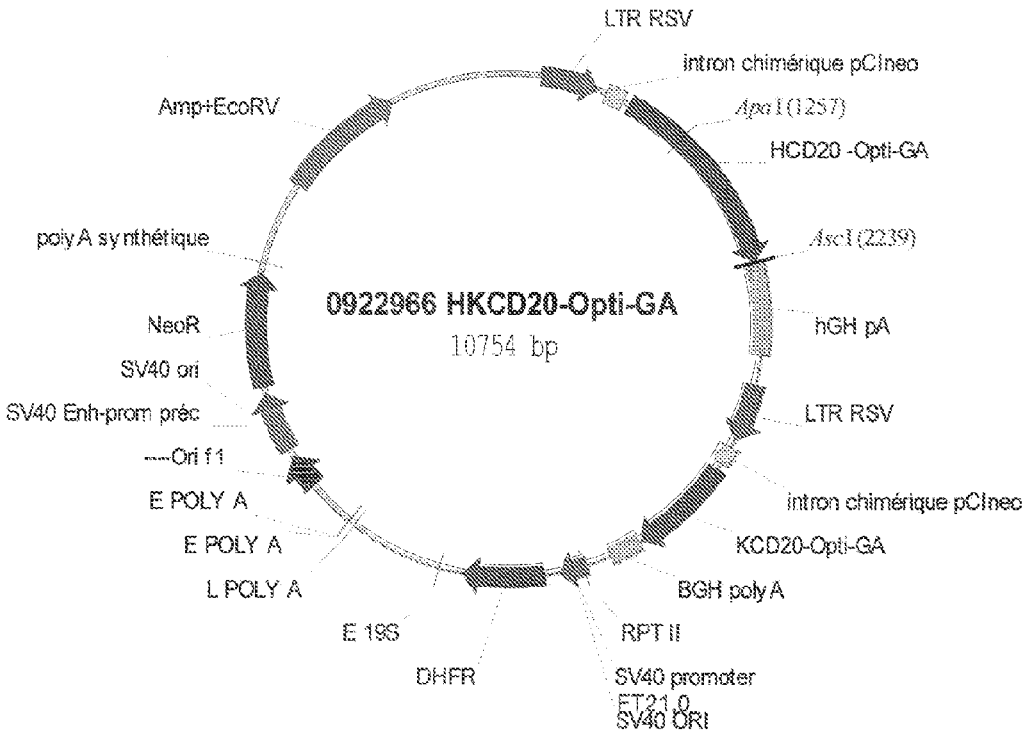

FIG. 8a illustrates a schematic map of the expression vector that is sued for expressing recombinant IgG1 antibodies bearing Fc variants as described herein. The resulting recombinant IgG1 antibodies possess binding specificity for the CD20 antigen. As shown in FIG. 8a, the nucleic acid encoding the heavy chain constant region bearing the mutations described in the specification and in the examples are inserted between the Apa1 and the Asc1 cloning sites present in the HKCD20-Opti-GA vector.

Figure 8B:
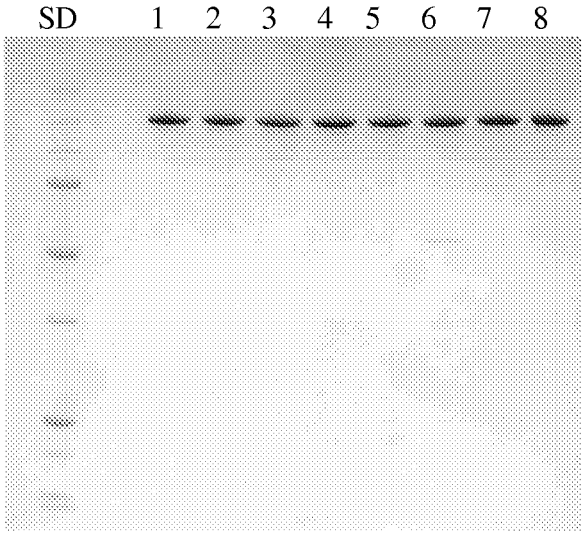
Figure 8C:
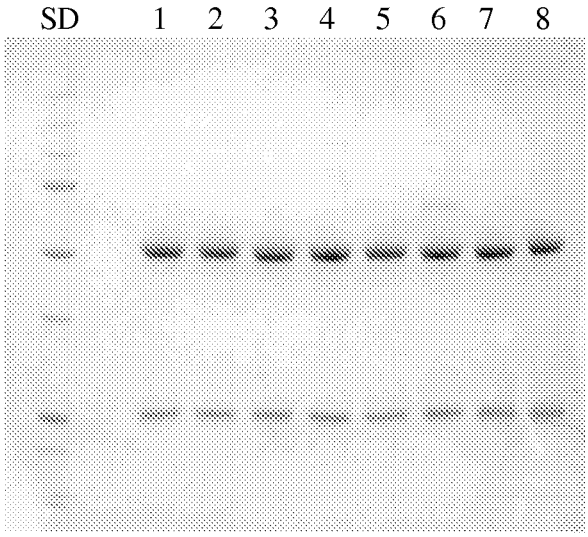

FIGS. 8b and 8c show SDS-PAGE of IgG variants under non reducing conditions and reducing conditions, respectively.

(1) refers to IgG comprising wild-type Fc; (2) refers to IgG comprising Fc-H variant; (3) refers to IgG comprising C6A_69 variant; (4) refers to IgG comprising C6A_78 variant; (5) refers to IgG comprising T5A_74 variant; (6) refers to IgG comprising C6A_74 variant, (7) refers to IgG comprising C6A_60 variant and (8) refers to comprising C6A_66.

Figure 9:
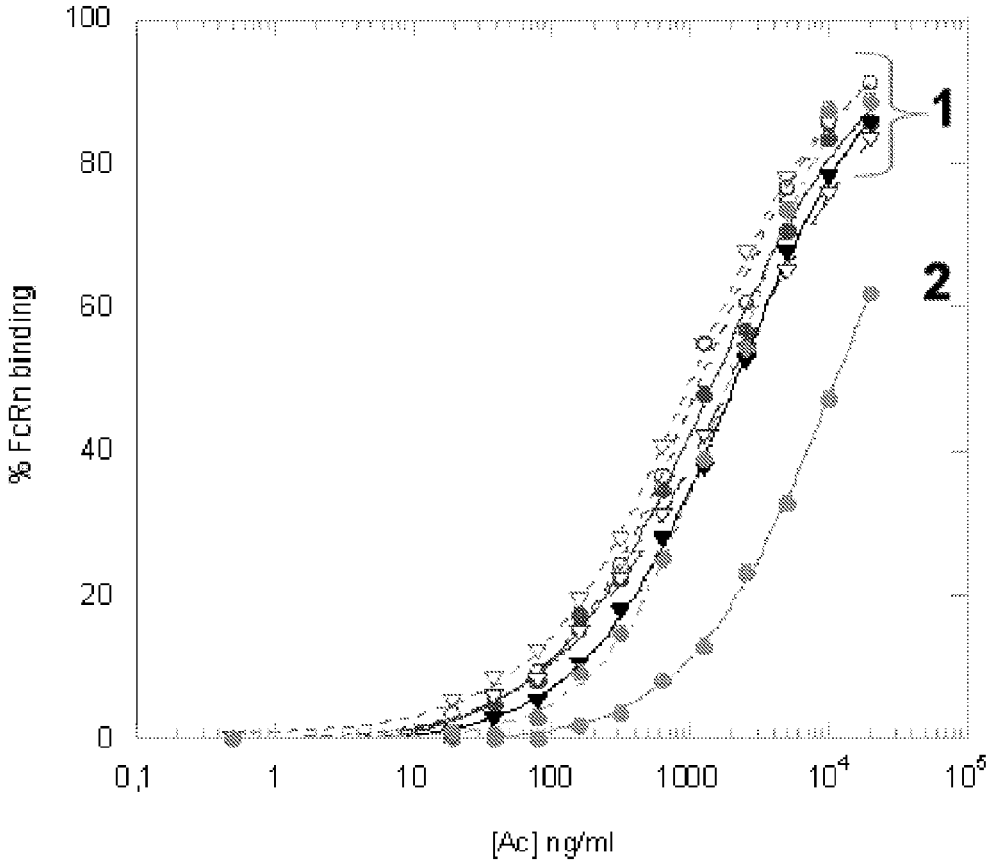

FIG. 9 shows the dose-effect curve for IgG variants of the invention ("1") and wild-type IgG ("2") obtained by ELISA assay performed as described in Example 2, III.1 for characterizing the binding of IgG variants to FcRn. X-coordinate: Concentration of IgG. Y-coordinate: percentage of FcRn bound to IgG.

Figure 10:
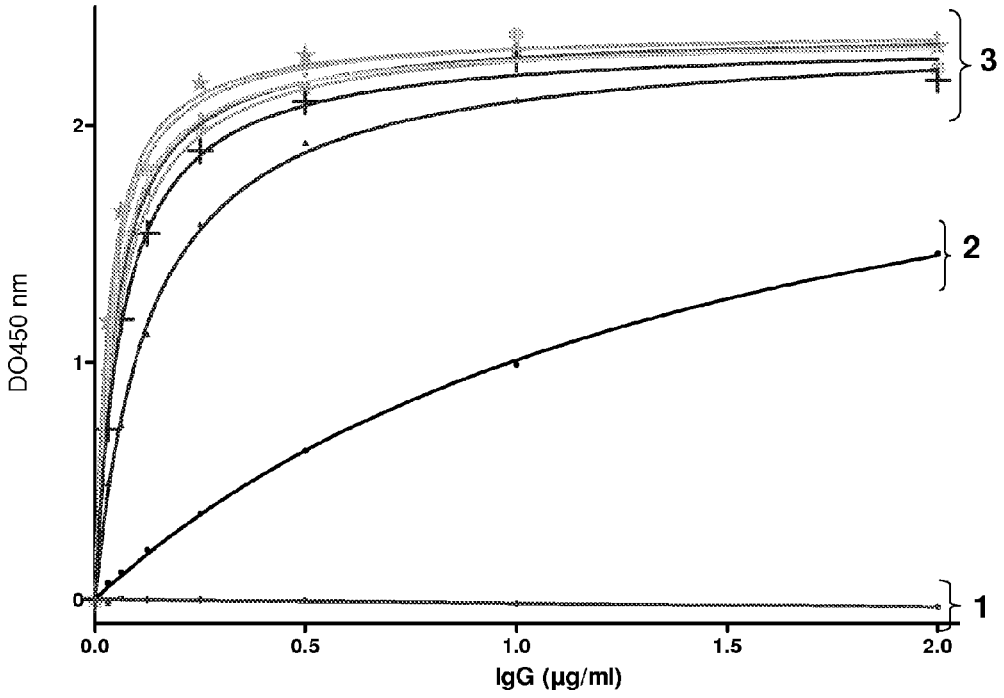

FIG. 10 shows the dose-effect curves obtained by ELISA assay for IgG variants of the invention in order to characterize their affinity to FcγRIIIa. (1) refers to the curve obtained for C6A_66 variant, (2) refers to the curve obtained for Rituximab and (3) refers to curves obtained for C6A_69; C6A_78; T5A_74; C6A_74; C6A_60 variants, and wild-type IgG. The ELISA assay was performed as described in Example 2, in part IV.1.a. X-coordinate: Concentration of IgG. Y-coordinate: percentage of FcγRIIIa bound to IgG.

Figure 11:
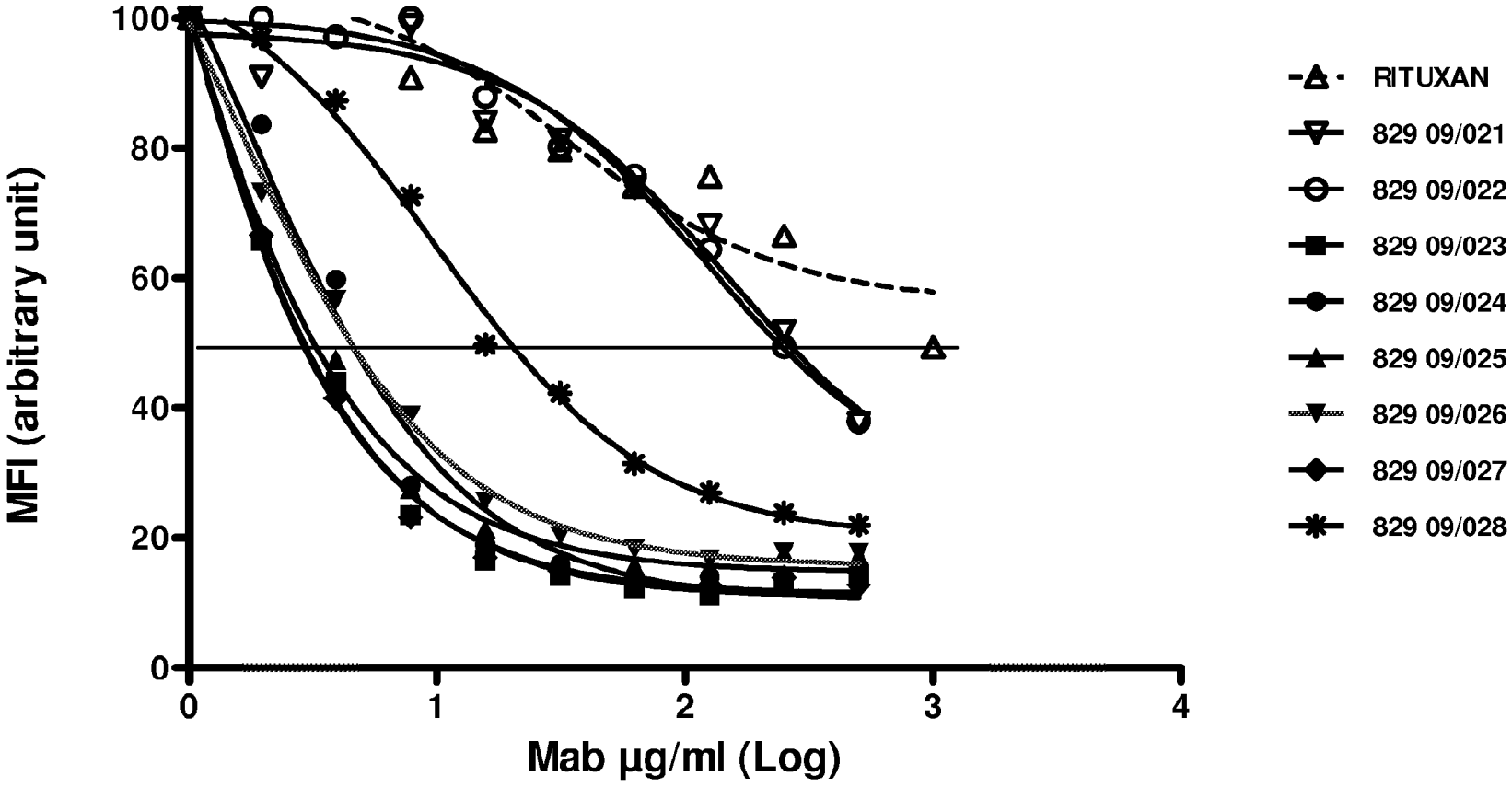

FIG. 11 illustrates the binding of various recombinant IgG to Jurkat FcRn. FIG. 11 shows the binding or Ritixan and of various variants according to the invention to Jurkat FcRn has been determined as described in the Materials and Methods Section above and expressed as mean fluorescence intensity (MFI) values.

Figure 12:
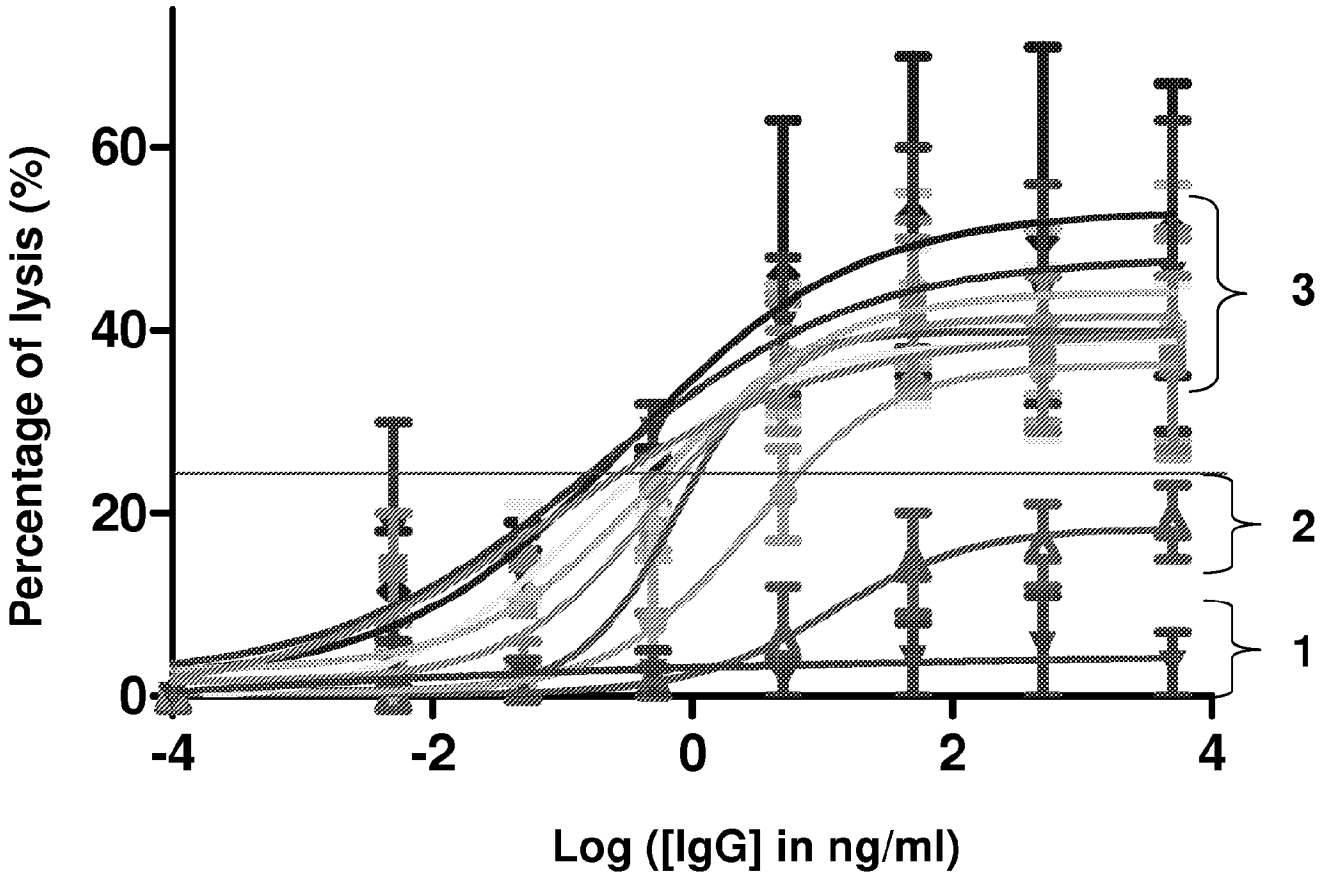

FIG. 12 shows the dose-effect curves obtained in ADCC assay for de IgG variants of the invention. (1) refers to the curve of C6A_66 variant, (2) refers to the curve of Rituximab and (3) refers to the curves of LFB-R603, WT-IgG, and IgG variants of the invention (namely C6A_69; C6A_78; T5A_74; C6A_74; C6A_60 variants). X-coordinate: Concentration of IgG. Y-coordinate: percentage of cell lysis.

DETAILED DESCRIPTION OF THE INVENTION

In order that the application may be more completely understood, several definitions are set forth below. Such definitions are meant to encompass grammatical equivalents.

Throughout the present specification and claims, the numbering of the residues in the Fc region is that of the immunoglobulin heavy chain according to the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

By "polypeptide" or "protein" as used herein is meant at least two covalently attached amino acids, which includes proteins, polypeptides, oligopeptides and peptides.

By "amino acid" as used herein is meant one of the 20 naturally occurring amino acids or any non-natural analogues that may be present at a specific, defined position.

The naturally occurring amino acids can be abbreviated with the three letter code, or with the one letter code:

| Amino acid | Three letter code | One letter code |
|---|---|---|
| alanine | ala | A |
| arginine | arg | R |
| asparagine | asn | N |
| aspartic acid | asp | D |
| asparagine or aspartic acid | asx | B |
| cysteine | cys | C |
| glutamic acid | glu | E |
| glutamine | gln | Q |
| glutamine or glutamic acid | glx | Z |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | try | W |
| tyrosine | tyr | Y |
| valine | val | V |

By "position" as used herein is meant a location in the sequence of a protein. For Fc region, the positions are numbered according to the EU index as in Kabat.

By "amino acid modification" herein is meant a change in the amino acid sequence of a polypeptide. "Amino acid modifications" which may be also termed "amino acid changes" herein include amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution N434S refers to a variant polypeptide, in this case an Fc variant, in which the asparagine at position 434 is replaced with serine. By "amino acid insertion" or "insertion" as used herein is meant the addition of an amino acid at a particular position in a parent polypeptide sequence. For example, insert G>235-236 designates an insertion of glycine between positions 235 and 236. By "amino acid deletion" or "deletion" as used herein is meant the removal of an amino acid at a particular position in a parent polypeptide sequence. For example, E294del designates the deletion of glutamic acid at position 294.

For example, the following format of modifications is preferentially used: 434S, or N434S, means that the parent amino acid in position 434, i.e. asparagine, is replaced by serine.

In case of a combination of substitutions, the preferred format is the following: 259I/315D/434Y or V259I/N315D/N434Y. That means that there are three substitutions in the variant, one in positions 259, one in position 315 and one in position 434, and that amino acid in position 259 of the parent polypeptide, i.e. valine, is replaced by isoleucine, that the amino acid in position 315 of the parent polypeptide, i.e. asparagine, is replaced by aspartic acid and that the amino acid in position 434 of the parent polypeptide, i.e. asparagine, is replaced by tyrosine.

By "variable region" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively. Variables regions comprise Complementarity-Determining Regions (CDRs) and Framework Regions (FR).

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3 which are CH2 and CH3 domains, respectively for IgGs) and the lower hinge region between Cgamma1 (Cγ1) and Cgamma2 (Cγ2). The human IgG1 heavy chain Fc region is defined herein to comprise residues C226 to its carboxyl-terminus, wherein the numbering is according to the EU index as in Kabat. In the context of human IgG1, the lower hinge refers to positions 226-236, the CH2 domain refers to positions 237-340 and the CH3 domain refers to positions 341-447 according to the EU index as in Kabat. The corresponding Fc region of other immunoglobulins can be identified by sequence alignments.

Fc may refer to this region in isolation, or this region in the context of an Fc polypeptide, as described below. By "Fc polypeptide" as used herein is meant a polypeptide that comprises all or part of an Fc region. Fc polypeptides include, but are not limited to, antibodies, Fc fusions, isolated Fcs, Fc-conjugates and Fc fragments.

The term "antibody" is used herein in the broadest sense. "Antibody" refers to any polypeptide which at least comprises (i) a Fc region and (ii) a binding polypeptide domain derived from a variable region of an immunoglobulin. The said binding polypeptide domain is able to bind specifically one given target antigen or a group of target antigens. A binding polypeptide domain which derives from a variable region of an immunoglobulin comprises one or more CDRs. Antibodies include, but are not limited to, full-length immunoglobulins, monoclonal antibodies, multi-specific antibodies, Fc-fusion protein comprising at least one variable region, synthetic antibodies (sometimes referred to herein as "antibody mimetics"), chimeric antibodies, humanized antibodies, fully human antibodies, antibody-fusion proteins, antibody conjugates and fragments of each respectively.

By "full-length antibody" or by "immunoglobulin" as used herein is meant the structure that constitutes the natural biological form of an antibody, including variable and constant regions. "Full length antibody" covers monoclonal full-length antibodies, wild-type full-length antibodies, chimeric full-length antibodies, humanized full-length antibodies, the list not being limitative.

In most mammals, including humans and mice, the structure of full-length antibodies is generally a tetramer. Said tetramer is composed of two identical pairs of polypeptide chains, each pair having one "light" (typically having a molecular weight of about 25 kDa) and one "heavy" chain (typically having a molecular weight of about 50-70 kDa). In some mammals, for example in camels and llamas, full-length antibodies may consist of only two heavy chains, each heavy chain comprising a variable domain attached to the Fc region.

The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see Sequences of Immunological Interest, 5th edition, NIH publication, No. 91-3242, E. A. Kabat et al., incorporated by reference herein in its entirety).

In the case of human immunoglobulins, light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

By "IgG" as used herein is meant a polypeptide belonging to the class of antibodies that are substantially encoded by a recognized immunoglobulin gamma gene. In humans, IgG comprises the subclasses or isotypes IgG1, IgG2, IgG3, and IgG4. In mice, IgG comprises IgG1, IgG2a, IgG2b, IgG3. Full-length IgGs are tetramers and consist of two identical pairs of two immunoglobulin chains, each pair having one light and one heavy chain, each light chain comprising immunoglobulin domains VL and CL, and each heavy chain comprising immunoglobulin domains VH, Cγ1 (also called CH1), Cγ2 (also called CH2), and Cγ3 (also called CH3). In the context of human IgG1, "CH1" refers to positions 118-220, CH2 domain refers to positions 237-340 and CH3 domain refers to positions 341-447 according to the EU index as in Kabat. IgG heavy chain also comprises a hinge domain which refers to positions 221-236 in the case of IgG1.

By "parent polypeptide" or "polypeptide parent" as used herein is meant an unmodified polypeptide that is subsequently modified to generate a variant. Said parent polypeptide may be a naturally occurring polypeptide, a variant of a naturally occurring polypeptide, engineered version of a naturally occurring polypeptide or a synthetic polypeptide. Parent polypeptide may refer to the polypeptide itself, or the amino acid sequence that encodes it. In the context of the present invention, the parent polypeptide comprises an Fc region selected from the group of wild-type Fc regions, their fragments and their mutants. Accordingly, the parent polypeptide may optionally comprise pre-existing amino acid modifications in its Fc region (i.e. an Fc mutant) as compared to wild-type Fc regions.

Advantageously, the parent polypeptide is an antibody, an immunoglobulin, an Fc fusion polypeptide, an Fc conjugate, this list not being limitative. Accordingly, by "Parent immunoglobulin" as used herein is meant immunoglobulin polypeptide that is modified to generate a variant immunoglobulin, and by "parent antibody" as used herein is meant antibody that is modified to generate a variant antibody. It should be noted that "parent antibody" includes, but are not limited to, known commercial, recombinantly produced antibodies.

As used herein, the term "at least one" is equal to "one or more".

By "variant polypeptide", "polypeptide variant" or "variant" as used herein is meant a polypeptide sequence that differs from that of a parent polypeptide sequence by virtue of at least one amino acid modification.

Variant may refer to Fc variant, Fc polypeptide variant, protein variant, antibody variant, immunoglobulin variant, IgG variant, this list not being limitative.

By "immunoglobulin variant" or "variant immunoglobulin" as used herein is meant an immunoglobulin sequence that differs from that of a parent immunoglobulin sequence by virtue of at least one amino acid modification. The parent polypeptide may be a naturally occurring or wild-type (WT) polypeptide, or may be a modified version of a WT polypeptide.

Parent polypeptides of interest are polypeptides which comprise an Fc region as defined above. Preferably the variant of the invention has a polypeptide sequence that differs from that of a parent polypeptide sequence by virtue of at least one amino acid modification in the Fc region. Consequently a variant of interest comprises an Fc variant.

Accordingly, by "Fc variant" or "variant Fc" as used herein is meant an Fc sequence that differs from that of a parent Fc sequence by virtue of at least one amino acid modification. An Fc variant may be an isolated Fc region and fragments thereof, or may exist in the context of an antibody, Fc fusion, and fragments therefore, the list not being limitative.

By "protein variant" or "variant protein" as used herein is meant a protein that differs from a parent protein by virtue of at least one amino acid modification. By "antibody variant" or "variant antibody" as used herein is meant an antibody that differs from a parent antibody by virtue of at least one amino acid modification. By "IgG variant" or "variant IgG" as used herein is meant an antibody that differs from a parent IgG by virtue of at least one amino acid modification. Preferably, the variant has at least one amino acid modification compared to the parent polypeptide, e.g. from about 1 to about 45 amino acid modifications, preferably from about 1 to about 20 amino acid modifications, and more preferably from about 1 to about 10 amino acid modifications.

The variant sequence herein will preferably possess at least about 80% identity with its parent polypeptide sequence, and most preferably at least about 90% identity.

As intended herein, a determined polypeptide having at least about 90% amino acid identity with a reference polypeptide possesses at least about 90%, 91%, 92%, 93%, 94%, 95%, 96%, 97%, 98%, 99% or 99.5% amino acid identity with the said reference polypeptide.

To determine the percent of identity of two amino acid sequences, the sequences are aligned for optimal comparison purposes. For example, gaps can be introduced in one or both of a first and a second amino acid sequence for optimal alignment and non-homologous sequences can be disregarded for comparison purposes. For optimal comparison purposes, the percent of identity of two amino acid sequences can be achieved with CLUSTAL W (version 1.82) with the following parameters: (1) CPU MODE=ClustalW mp; (2) ALIGNMENT=<<full<<; (3) OUTPUT FORMAT=<<aln w/numbers<<; (4) OUTPUT ORDER=<<aligned<<; (5) COLOR ALIGNMENT=<<no<<; (6) KTUP (word size)= <<default<<; (7) WINDOW LENGTH=<<default<<; (8) SCORE TYPE=<<percent<<; (9) TOPDIAG=<<default<<; (10) PAIRGAP=<<default>>; (11) PHYLOGENETIC TREE/TREE TYPE=>>none>>; (12) MATRIX=>>default>>; (13) GAP OPEN=>>default>>; (14) END GAPS=>>default>>; (15) GAP EXTENSION=>>default>>; (16) GAP DISTANCES=>>, default>>; (17) TREE TYPE=>>cladogram>> et (18) TREE GRAP DISTANCES=>>hide>>.

By "wild type or WT" herein is meant an amino acid sequence or a nucleotide sequence that is found in nature, including allelic variations. A WT protein, polypeptide, antibody, immunoglobulin, IgG, etc. have an amino acid sequence or a nucleotide sequence that has not been intentionally modified.

By "FcRn" or "neonatal Fc Receptor" as used herein is meant a protein that binds the IgG antibody Fc region and is encoded at least in part by an FCRN gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FCRN gene. Unless otherwise noted herein, FcRn or FcRn protein refers to the complex of α-chain with beta-2-microglobulin. In human, the gene coding for FcRn is called FCGRT.

By "increased FcRn binding" as used herein is meant the increase in binding affinity, in vivo or in vitro, of the variant of the invention to FcRn, compared to the parent polypeptide. The ability of the polypeptide variant to bind an FcRn may be evaluated in vitro by ELISA (Example 1 part IV.1.a) or SPR technology (Example 1 part IV.1.b.). The variants which have an enhanced binding property for FcRn most often have an enhanced serum retention in vivo and, thus, an increased half-life.

In order to increase the retention of the Fc region in vivo, the increase in binding affinity for FcRn must occur at around pH 6, while maintaining lower affinity at around pH 7.4.

Although still under examination, Fc regions are believed to have a longer half-life in vivo, because the binding to FcRn at pH 6 allow the sequestration of Fc regions into endosomes (Ghetie and Ward, 1997 Immunol Today. 18 (12): 592-598, incorporated by reference herein in its entirety). The endosomal compartment then recycles the Fc regions to the cell surface. Once the compartment opens to the extracellular space, the higher pH, almost 7.4, induces the release of Fc regions back into the blood. Therefore, the amino acid modifications in the Fc region that will increase Fc regions' half-life in vivo will ideally increase FcRn binding at the lower pH while still allowing release of Fc region at higher pH.

The term "in vivo half-life" as used herein refers to a biological half-life of a polypeptide of interest in the circulation of a given animal and is represented by the time required for half the quantity present in the circulation of the animal to be cleared from the circulation and/or other tissues in the animal.

The present invention is based on the identification of amino acid modifications of Fc region which modifications increase the binding affinity of the Fc region for FcRn. The amino acid modifications of interest have been determined by generating two Fc variants libraries by random mutagenesis and by measuring the binding property of said variants for FcRn.

Accordingly, the present invention relates to variants of parent polypeptides comprising an Fc region which display increased binding to FcRn as compared to said parent polypeptides.

A parent polypeptide of the invention is a polypeptide comprising an Fc region. Said polypeptide may comprise one single polypeptide chain or several polypeptide chains which are not covalently linked together. Parent polypeptides include, but are not limited to, antibodies, Fc fusion proteins, Fc conjugates, Fc derivated polypeptides, isolated Fc and fragments thereof. As a consequence, said parent polypeptide may be a naturally occurring polypeptide, a variant of a naturally occurring polypeptide, an engineered version of a naturally occurring polypeptide, a synthetic polypeptide or a polypeptide comprising a non-proteinous fragment. An engineered version of a naturally occurring polypeptide is a polypeptide with is not encoded by a naturally occurring gene. For example, the engineered polypeptide may be a chimeric antibody or a humanized antibody.

The Fc region of the parent polypeptide is preferably selected from the group consisting of wild-type Fc regions of IgGs, fragments and mutants thereof. Herein, Fc region of IgG corresponds to the "lower hinge" -CH2-CH3 domain (For IgGs, CH2 and CH3 are also called Cγ2 and Cγ3 domains). The sequence of "lower hinge" -CH2-CH3 domain of the wild type human IgG1 is the sequence of SEQ ID NO:1. In the context of human IgG1, the lower hinge refers to positions 226-236, the CH2 domain refers to positions 237-340 and the CH3 domain refers to positions 341-447 according to the EU index as in Kabat. The analogous domains for other IgG sub-classes can be determined from amino acid sequence alignment of heavy chains or heavy chain fragments of said IgG sub-classes with that of human IgG1.

Fragments of Fc region are defined as polypeptides which comprise one or more polypeptides derived from a wild-type Fc region, preferably from the "lower hinge-CH2-CH3" domain of a wild-type IgG. The said fragments have a dissociation constant for FcRn lower than 1 microM according to the SPR assay described in Example 1 part IV.1.).

As mentioned above, the parent polypeptide can comprise a wild-type Fc mutant i.e a Fc region which already comprises pre-existing amino acid modifications such as additions, insertions and/or substitutions with proviso that the said Fc mutant has a dissociation constant for FcRn lower than 1 microM according to the SPR assay described in Example 1 part IV.1. and is not a wild-type Fc region.

By "variant polypeptide" or "variant" as used herein is meant a polypeptide sequence which differs from that of a parent polypeptide in virtue of at least one amino acid modification.

The variant polypeptide according to the present invention displays an increased binding to FcRn as compared to the corresponding parent polypeptide. In other words, the affinity of the variant for FcRn is higher than that of the parent polypeptide. Such variants are optimized variants according to the invention.

The affinity of the said polypeptides for FcRn can be evaluated by well-known methods of the prior art. For example, the one skilled in the art may determine the dissociation constant (Kd) using Surface Plasmon Resonance (SPR) experiments as illustrated in the Example 1 part IV.1.b. of the present application. If the variant has a Kd 1.1-fold lower than that of its corresponding parent then the said variant is an optimized variant according to the invention.

As an alternative, the one skilled in the art may perform an appropriate ELISA assay. An appropriate ELISA assay enables to compare the bond strength of the variant and that of the parent to FcRn as illustrated in Example 1. The specific signals detected for the variant and the parent polypeptide are compared. The variant is an optimized variant of the invention if its specific signal is at least 1.2-fold stronger, more preferably at least 3.2-fold stronger than that of the parent polypeptide (i.e. at least as good as the Fc variant having the double amino acid modification T250Q/M428L).

Appropriate ELISA assays are illustrated in Example 1 of the present application. The binding affinity can be indifferently determined by evaluating the full-length polypeptides (see Example 2 part III) or by evaluating the isolated Fc regions thereof (see Example 1 part IV).

According to the invention, polypeptide variants of interest comprise at least one amino acid modification in its Fc region as compared to the parent polypeptide. The amino acid modifications are selected from the group consisting of amino acid insertions, deletions and substitutions.

The applicants have shown that in order to obtain a polypeptide variant having increased binding to FcRn as compared to its parent polypeptide, the at least one amino acid modification should be introduced at an amino acid position selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index as in Kabat.

Herein, the "EU index as in Kabat" refers to the residue numbering of the human IgG1 EU antibody. For example, the analogous positions for other Fc regions can be determined from amino acid sequence alignment of the said Fc regions with human IgG1 heavy chain fragment comprising the polypeptide of SEQ ID NO:1. For illustrative purpose, FIG. 6 depicts the sequence alignment of human IgG1, IgG2, IgG3 and IgG4 heavy chain fragments comprising "lower hinge-CH2-CH3" domain.

By "at least one amino acid modification" as used herein means "one or more modifications". It is considered that the introduction of more than 20 amino acid modifications in the Fc region may drastically impair its biological activities. Accordingly, the polypeptide variant preferably has from 1 to 20 and more preferably from 1 to 10 amino acid modifications, at positions selected from the list cited above. By "1 to 20 amino acid modifications" as used herein encompasses 1, 2, 3, 4, 5, 6, 7, 8, 9, 10, 11, 12, 13, 14, 15, 16, 17, 18, 19 and 20 amino acid modifications. The said polypeptide variant sequence preferably possesses at least about 90% identity with its parent polypeptide sequence.

As intended herein, a determined polypeptide having at least about 90% amino acids with a reference polypeptide possesses at least about 90%, 91%, 92%, 93%, 94%, 95%, 96%, 97%, 98%, 99% or 99.5% amino acids identity with said reference polypeptide.

The Fc variants of the present invention which display the highest binding affinity for FcRn generally comprise more than one amino acid modifications. The results obtained from phage ELISA assay described in example II shows that the optimized variants comprising more than one amino acid modification may have a specific signal from about 3.2-fold to 30-fold stronger (see table 2 and table 3) than the wild-type Fc whereas the variants with a single point amino acid modification (see table 1) may have a signal from about 1.2-fold to 3.5-fold stronger than the wild-type Fc. As illustrated in table 3, the signal of the optimized variant may be from about 1-fold to about 10-fold stronger than that of Fc-H which refers to the Fc variant having the double amino acid modification T250Q/M428L.

Accordingly, in a specific embodiment, the said variant comprises at least two amino acid modifications selected from the list consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index as in Kabat.

As described in table 5 of the present application, Fc variants which display the highest binding affinity for FcRn may have 3 to 6 amino acid modifications.

Accordingly, in a further embodiment, the variant polypeptides of the invention may comprise 3 to 6 amino acid modifications at amino acid positions selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index as in Kabat.

The amino acid modifications are preferably selected from the group of deletions and substitutions.

Some amino acid positions of the above list—namely 226, 230, 241, 264, 307, 315, 330, 342, 362, 378, 382, 389, 396, 397, 421 and 434—are key positions. In other words, the Fc variants which display high binding affinity for FcRn are likely to comprise at least one amino acid modification at the said amino acid positions.

In certain embodiments, the polypeptide variant according to the invention comprises at least one amino acid modification at amino acid positions selected from the group consisting of 226, 230, 241, 264, 307, 315, 330, 342, 362, 378, 382, 389, 396, 397, 421 and 434 of the Fc region as compared to the parent polypeptide, wherein the numbering of the amino acids in the Fc region is that of the EU index as in Kabat.

Among the above key positions, the sequencing of the Fc variants which display the strongest binding for FcRn have shown that the amino acid positions 230, 264, 307, 315, 330, 378 and 434 are the most often mutated positions. Accordingly, in another embodiment, the at least one modification occurs at one position selected from the group consisting of 230, 264, 307, 315, 330, 378 and 434, more preferably from the group consisting of 264, 315, 378 and 434 of the Fc region as compared to the parent polypeptide, wherein the numbering of the amino acids in the Fc region is that of the EU index as in Kabat.

As mentioned above, the introduction of at least two amino acid modifications can noticeably enhance the binding affinity of Fc variant for FcRn as compared to the Fc parent.

Accordingly, in an alternate embodiment, the polypeptide variant comprises at least two amino acid modifications, said at least two amino acid modifications comprising:

(i) one modification at an amino acid position selected from the group consisting of 226, 230, 241, 264, 307, 315, 330, 342, 362, 378, 382, 389, 396, 397, 421, and 434; and (ii) at least one modification at an amino acid position selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447, of the Fc region as compared to the parent polypeptide wherein the numbering of the amino acids in the Fc region is that of the EU index as in Kabat and with the proviso that the modification (i) does not occur at the same amino acid position as the modification (ii).

For example, according to the said proviso, if the amino acid modification (i) occurs at position 434, the at least one amino acid modification (ii) can occur at any position of the list cited in (ii) except on position 434.

In another embodiment, the polypeptide variant comprises at least two amino acid modifications, said at least two amino acid modifications comprising:

(i) one modification at an amino acid position selected from the group consisting of 264, 315, 378 and 434; and (ii) at least one modification at an amino acid position selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447 of the Fc region, wherein the numbering of the amino acids in the Fc region is that of the EU index as in Kabat and with the proviso that the modification (i) does not occur at the same amino acid position as the modification (ii).

In an additional embodiment, the said variant comprises at least two amino acid modifications, said at least two amino acid modifications comprising:

(i) one amino acid modification at a position selected from the group consisting of 264, 315, 378 and 434; and (ii) at least one amino acid modification at a position selected from the group consisting of 226, 230, 241, 264, 307, 315, 330, 342, 362, 378, 382, 389, 396, 397, 421 and 434 of the Fc region, wherein the numbering of the amino acids in the Fc region is that of the EU index as in Kabat and with the proviso that the modification (i) does not occur at the same amino acid position as the modification (ii).

In another additional embodiment the said variant comprises at least two amino acid modifications comprising:

(i) one amino acid modification at a position selected from the group consisting of 378 and 434; and (ii) at least one amino acid modification at a position selected from the group consisting of 226, 230, 241, 264, 307, 315, 330, 342, 362, 378, 382, 389, 396, 397, 421 and 434 of the Fc region, wherein the numbering of the amino acids in the Fc region is that of the EU index as in Kabat and with the proviso that the modification (i) does not occur at the same amino acid position as the modification (ii).

In an alternate embodiment, the polypeptide variant comprises at least three amino acid modifications in its Fc region. Accordingly, the said at least three amino acid modifications may comprise:

(i) two modifications at two amino acid positions selected from the group consisting of 226, 230, 241, 264, 307, 315, 330, 342, 362, 378, 382, 389, 396, 397, 421 and 434; and (ii) at least one modification at an amino acid position selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447 of the Fc region as compared to the parent polypeptide wherein the numbering of the amino acids in the Fc region is that of the EU index as in Kabat and with the proviso that the modification (i) does not occur at the same amino acid position as the modification (ii).

In an alternate embodiment, the polypeptide variant comprises at least three amino acid modifications, said at least three amino acid modifications comprising:

(i) one modification at an amino acid position selected from the group consisting of 264, 315, 378 and 434;

(ii) one modification at an amino acid position selected from the group consisting of 226, 230, 241, 264, 307, 315, 330, 342, 362, 378, 382, 389, 396, 397, 421 and 434; and (iii) at least one modification at an amino acid position selected from the group consisting of 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447 of the Fc region, wherein the numbering of the amino acids in the Fc region is that of the EU index as in Kabat and with the proviso that modification (i), modification (ii) and modification (iii) do not simultaneously occur at the same amino acid positions.

In other embodiments, the polypeptide variant comprises at least three amino acid modifications, said at least three amino acid modifications comprising:

(i) one modification at an amino acid position selected from the group consisting of 378 and 434;

(ii) one modification at an amino acid position selected from the group of 226, 230, 241, 264, 307, 315, 330, 342, 362, 378, 382, 389, 396, 397, 421 and 434; and (iii) at least one modification at an amino acid position selected from the group consisting of 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447 of the Fc region, wherein the numbering of the amino acids in the Fc region is that of the EU index as in Kabat and with the proviso that modification (i), modification (ii) and modification (iii) do not simultaneously occur at the same amino acid positions.

In all previously cited embodiments of the present invention, the amino acid modifications are preferably selected from the group consisting of amino acid substitutions and deletions.

A further object of the invention relates to a variant of a parent polypeptide comprising a Fc region which exhibits increased binding to FcRn as compared to said parent polypeptide and comprises at least one amino acid modification in the Fc region selected from the group consisting of 226G, 226Y, 227S, 227L, 228R, 228L, 230S, 230T, 230L, 230A, 230Q, 231T, 231V, 233D, 234R, 239A, 241L, 241Y, 241R, 243L, 246R, 250A, 252L, 256N, 259I, 264A, 264E, 264M, 265G, 265N, 267N, 267R, 269D, 269G, 270N, 270E, 276S, 284L, 285Y, 288R, 2891, 290R, 290E, 291S, 291Q, 292W, 294del, 297D, 298G, 298N, 299M, 299A, 299K, 301C, 302A, 303A, 3031, 305A, 307P, 307A, 307N, 308I, 309P, 311R, 315D, 317R, 320T, 320E, 322R, 325S, 327V, 327T, 330V, 330T, 332V, 334E, 334R, 335A, 338R, 340E, 342R, 342E, 342K, 343S, 345Q, 345G, 347R, 350A, 352S, 354P, 355Q, 355G, 356N, 359A, 360N, 360R, 361D, 361S, 362R, 362E, 369A, 370R, 371D, 375A, 375G, 378V, 378T, 378S, 380Q, 382V, 382G, 383R, 383N, 384I, 384T, 385R, 386R, 386K, 387S, 387T, 389T, 389K, 389R, 390S, 392E, 392R, 393N, 394A, 395A, 395S, 396S, 396L, 397A, 397M, 398P, 399N, 400P, 401A, 401G, 403T, 404L, 408T, 411A, 412A, 414R, 415D, 415N, 416K, 416G, 418R, 418K, 418E, 419H, 420R, 421T, 421S, 421D, 422A, 424L, 426T, 428L, 433R, 433P, 434Y, 434S, 434H, 438R, 439R, 440R, 440N, 443R, 444F, 444P, 445S, 446A, 447E and 447N of the Fc region, as compared to the parent polypeptide, wherein the numbering of the amino acids in the Fc region is that of the EU index as in Kabat.

In an alternate embodiment, the said polypeptide comprises at least one modification selected from the group consisting of 226G, 227L, 230S, 230T, 230L, 231T, 241L, 243L, 250A, 256N, 259I, 264E, 265G, 267R, 290E, 294del, 303A, 305A, 307P, 307A, 308I, 315D, 322R, 325S, 327V, 330V, 342R, 347R, 352S, 361D, 362R, 362E, 370R, 378V, 378T, 382V, 383N, 386R, 386K, 387T, 389T, 389K, 392R, 395A, 396L, 397M, 403T, 404L, 415N, 416K, 421T, 426T, 428L, 433R, 434Y, 434S and 439R of the Fc region, as compared to the parent polypeptide, wherein the numbering of the amino acids in the Fc region is that of the EU index as in Kabat.

Preferably, the said variant has from 1 to 20, more preferably from 1 to 10 amino acid modifications selected from the above lists, as compared to the parent polypeptide. As used herein, by "from 1 to 20 modifications" is meant 1, 2, 3, 4, 5, 6, 7, 8, 9, 10, 11, 12, 13, 14, 15, 16, 17, 18, 19 and 20 modifications.

In some embodiments, the said variant comprises from 3 to 6 amino acid modifications selected from the group consisting of 226G, 226Y, 227S, 227L, 228R, 228L, 230S, 230T, 230L, 230A, 230Q, 231T, 231V, 233D, 234R, 239A, 241L, 241Y, 241R, 243L, 246R, 250A, 252L, 256N, 259I, 264A, 264E, 264M, 265G, 265N, 267N, 267R, 269D, 269G, 270N, 270E, 276S, 284L, 285Y, 288R, 2891, 290R, 290E, 291S, 291Q, 292W, 294del, 297D, 298G, 298N, 299M, 299A, 299K, 301C, 302A, 303A, 3031, 305A, 307P, 307A, 307N, 308I, 309P, 311R, 315D, 317R, 320T, 320E, 322R, 325S, 327V, 327T, 330V, 330T, 332V, 334E, 334R, 335A, 338R, 340E, 342R, 342E, 342K, 343S, 345Q, 345G, 347R, 350A, 352S, 354P, 355Q, 355G, 356N, 359A, 360N, 360R, 361D, 361S, 362R, 362E, 369A, 370R, 371D, 375A, 375G, 378V, 378T, 378S, 380Q, 382V, 382G, 383R, 383N, 384I, 384T, 385R, 386R, 386K, 387S, 387T, 389T, 389K, 389R, 390S, 392E, 392R, 393N, 394A, 395A, 395S, 396S, 396L, 397A, 397M, 398P, 399N, 400P, 401A, 401G, 403T, 404L, 408T, 411A, 412A, 414R, 415D, 415N, 416K, 416G, 418R, 418K, 418E, 419H, 420R, 421T, 421S, 421D, 422A, 424L, 426T, 428L, 433R, 433P, 434Y, 434S, 434H, 438R, 439R, 440R, 440N, 443R, 444F, 444P, 445S, 446A, 447E and 447N of the Fc region, as compared to the parent polypeptide, wherein the numbering of the amino acids in the Fc region is that of the EU index as in Kabat.

In an alternate embodiment, the said polypeptide comprises from 3 to 6 amino acid modifications selected from the group consisting of 226G, 227L, 230S, 230T, 230L, 231T, 241L, 243L, 250A, 256N, 259I, 264E, 265G, 267R, 290E, 294del, 303A, 305A, 307P, 307A, 308I, 315D, 322R, 325S, 327V, 330V, 342R, 347R, 352S, 361D, 362R, 362E, 370R, 378V, 378T, 382V, 383N, 386R, 386K, 387T, 389T, 389K, 392R, 395A, 396L, 397M, 403T, 404L, 415N, 416K, 421T, 426T, 428L, 433R, 434Y, 434S and 439R of the Fc region, as compared to the parent polypeptide, wherein the numbering of the amino acids in the Fc region is that of the EU index as in Kabat.

Some amino acid modifications of the above lists are key modifications. In other words, the Fc variants which display high binding affinity to FcRn are likely to comprise at least one amino acid modification selected from the said key modifications.

Accordingly, the said polypeptide variant may comprise at least one modification selected from the group consisting of 226G, 230S, 230T, 230L, 241L, 264E, 307P, 315D, 330V, 342R, 362R, 362E, 378V, 378T, 382V, 389T, 389K, 396L, 397M, 421T, 434Y and 434S of the Fc region compared to said parent polypeptide, wherein the numbering of the amino acids in the Fc region is that of the EU index as in Kabat.

In another embodiment, the said polypeptide variant comprises at least one amino acid modification selected from the group consisting of 264E, 315D, 378V, 378T, 434Y and 434S of the Fc region as compared to said parent polypeptide, wherein the numbering of the amino acids in the Fc region is that of the EU index as in Kabat.

In a further embodiment, the said polypeptide variant comprises at least one amino acid modification selected from the group consisting of 378V, 378T, 434Y and 434S of the Fc region as compared to said parent polypeptide, wherein the numbering of the amino acids in the Fc region is that of the EU index as in Kabat.

As mentioned above, the introduction of at least two amino acid modifications can noticeably enhance the binding of Fc variants to FcRn as compared to the parents. At least one of said modifications may be selected from the key modifications i.e. from the group consisting of 226G, 230S, 230T, 230L, 241L, 264E, 307P, 315D, 330V, 342R, 362R, 362E, 378V, 378T, 382V, 389T, 389K, 396L, 397M, 421T, 434Y and 434S.

In an alternate embodiment, the said polypeptide variant comprises at least two amino acid modifications, the said at least two modifications comprising (i) one modification selected from the group consisting of 226G, 230S, 230T, 230L, 241L, 264E, 307P, 315D, 330V, 342R, 362R, 362E, 378V, 378T, 382V, 389T, 389K, 396L, 397M, 421T, 434Y and 434S; and (ii) at least one amino acid modification at an amino acid position selected from the group consisting of 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447 of the Fc region, as compared to the parent polypeptide, wherein the numbering of the amino acids in the Fc region is that of the EU index as in Kabat and with the proviso that the modification (i) does not occur at the same amino acid position as the modification (ii).

In a further embodiment, the said variant comprises at least two amino acid modifications, the said at least two modifications comprising (i) one amino acid modification selected from the group consisting of 378V, 378T, 434Y and 434S; and (ii) at least one amino acid modification at an amino acid position selected from the group consisting of 226, 230, 241, 264, 307, 315, 330, 342, 362, 378, 382, 389, 396, 397, 421 and 434 of the Fc region, wherein the numbering of the amino acids in the Fc region is that of the EU index as in Kabat and with the proviso that the modification (i) does not occur at the same amino acid position as the modification (ii).

In another embodiment, the said variant comprises at least two amino acid modifications, the said at least two modifications comprising:

(i) one amino acid modification selected from 378V, 378T, 434Y and 434S; and (ii) at least one amino acid modification selected from 226G, 230S, 230T, 230L, 241L, 264E, 307P, 315D, 330V, 342R, 362R, 362E, 378V, 378T, 382V, 389T, 389K, 396L, 397M, 421T, 434Y and 434S, and more preferably, from 226G, 230S, 230T, 230L, 241L, 264E, 307P, 315D, 330V, 362R, 378V, 378T, 389T, 389K, 434Y and 434S of the Fc region, wherein the numbering of the amino acids in the Fc region is that of the EU index as in Kabat and with the proviso that the modification (i) does not occur at the same amino acid position as the modification (ii).

Accordingly, a further object of the invention relates to a variant of a parent polypeptide comprising an Fc region which exhibits increased binding to FcRn as compared to said parent polypeptide and comprises at least one combination of amino acid modifications in the Fc region.

The at least one combination of modifications is selected from the group consisting of: 226G/330V, 230L/264E, 230L/378V, 230S/315D, 230S/434Y, 230T/378V, 241L/434S, 250A/434Y, 264E/378T, 305A/315D, 305A/330V, 305A/434Y, 307P/434Y, 315D/389T, 330V/382V, 330V/389T, 378V/421T, 389K/434Y, 389T/434Y, 396L/434S, 230T/264E, 230T/315D, 230T/434S, 230T/434Y, 241L/307P, 264E/307P, 264E/396L, 315D/362R, 315D/382V, 362R/434Y, 378V/434Y, 382V/434Y, 226G/315D, 226G/434Y, 241L/378V, 307P/378V, 241L/264E, 378V/434S, 264E/378V, 264E/434S, 315D/330V, 330V/434Y and 315D/434Y of the Fc region, wherein the numbering of the amino acids in the Fc region is that of the EU index as in Kabat.

The said variant may further comprise at least one modification selected from the group of 226G, 226Y, 227S, 227L, 228R, 228L, 230S, 230T, 230L, 230A, 230Q, 231T, 231V, 233D, 234R, 239A, 241L, 241Y, 241R, 243L, 246R, 250A, 252L, 256N, 259I, 264A, 264E, 264M, 265G, 265N, 267N, 267R, 269D, 269G, 270N, 270E, 276S, 284L, 285Y, 288R, 2891, 290R, 290E, 291S, 291Q, 292W, 294del, 297D, 298G, 298N, 299M, 299A, 299K, 301C, 302A, 303A, 3031, 305A, 307P, 307A, 307N, 308I, 309P, 311R, 315D, 317R, 320T, 320E, 322R, 325S, 327V, 327T, 330V, 330T, 332V, 334E, 334R, 335A, 338R, 340E, 342R, 342E, 342K, 343S, 345Q, 345G, 347R, 350A, 352S, 354P, 355Q, 355G, 356N, 359A, 360N, 360R, 361D, 361S, 362R, 362E, 369A, 370R, 371D, 375A, 375G, 378V, 378T, 378S, 380Q, 382V, 382G, 383R, 383N, 384I, 384T, 385R, 386R, 386K, 387S, 387T, 389T, 389K, 389R, 390S, 392E, 392R, 393N, 394A, 395A, 395S, 396S, 396L, 397A, 397M, 398P, 399N, 400P, 401A, 401G, 403T, 404L, 408T, 411A, 412A, 414R, 415D, 415N, 416K, 416G, 418R, 418K, 418E, 419H, 420R, 421T, 421S, 421D, 422A, 424L, 426T, 428L, 433R, 433P, 434Y, 434S, 434H, 438R, 439R, 440R, 440N, 443R, 444F, 444P, 445S, 446A, 447E and 447N of the Fc region, as compared to the parent polypeptide, wherein the numbering of the amino acids in the Fc region is that of the EU index as in Kabat.

In another embodiment, a variant according to the present invention comprises:

(i) at least one combination of amino acid modifications selected from the group consisting of:

226G/330V, 230L/264E, 230L/378V, 230S/315D, 230S/434Y, 230T/378V, 241L/434S, 250A/434Y, 264E/378T, 305A/315D, 305A/330V, 305A/434Y, 307P/434Y, 315D/389T, 330V/382V, 330V/389T, 378V/421T, 389K/434Y, 389T/434Y, 396L/434S, 230T/264E, 230T/315D, 230T/434S, 230T/434Y, 241L/307P, 264E/307P, 264E/396L, 315D/362R, 315D/382V, 362R/434Y, 378V/434Y, 382V/434Y, 226G/315D, 226G/434Y, 241L/378V, 307P/378V, 241L/264E, 378V/434S, 264E/378V, 264E/434S, 315D/330V, 330V/434Y, and 315D/434Y; and (ii) at least one amino acid modifications selected from the group consisting of 226G, 227L, 228L, 228R 230S, 230T, 230L, 231T, 241L, 243L, 250A, 256N, 259I, 264E, 265G, 267R, 290E, 294del, 303A, 305A, 307P, 307A, 308I, 315D, 322R, 325S, 327V, 330V, 342R, 347R, 352S, 361D, 362R, 362E, 370R, 378V, 378T, 382V, 383N, 386R, 386K, 387T, 389T, 389K, 392R, 395A, 396L, 397M, 403T, 404L, 415N, 416K, 421T, 426T, 428L, 433R, 434Y, 434S and 439R of the Fc region, as compared to the parent polypeptide, wherein the numbering of the amino acids in the Fc region is that of the EU index as in Kabat and with the proviso that the modifications (i) does not occur at the same amino acid position as the modification (ii).

In other embodiments, the said variant comprises at least one combination of amino acid modifications selected from the group consisting of 250A/434Y, 307P/434Y, 230T/434S, 264E/396L, 378V/434Y, 378V/434S, 264E/378V, 264E/434S, 315D/330V, and 315D/434Y of the Fc region, wherein the numbering of the amino acids in the Fc region is that of the EU index as in Kabat.

The said variant may further comprise at least one amino acid modification selected from the group of 226G, 226Y, 227S, 227L, 228R, 228L, 230S, 230T, 230L, 230A, 230Q, 231T, 231V, 233D, 234R, 239A, 241L, 241Y, 241R, 243L, 246R, 250A, 252L, 256N, 259I, 264A, 264E, 264M, 265G, 265N, 267N, 267R, 269D, 269G, 270N, 270E, 276S, 284L, 285Y, 288R, 2891, 290R, 290E, 291S, 291Q, 292W, 294del, 297D, 298G, 298N, 299M, 299A, 299K, 301C, 302A, 303A, 3031, 305A, 307P, 307A, 307N, 308I, 309P, 311R, 315D, 317R, 320T, 320E, 322R, 325S, 327V, 327T, 330V, 330T, 332V, 334E, 334R, 335A, 338R, 340E, 342R, 342E, 342K, 343S, 345Q, 345G, 347R, 350A, 352S, 354P, 355Q, 355G, 356N, 359A, 360N, 360R, 361D, 361S, 362R, 362E, 369A, 370R, 371D, 375A, 375G, 378V, 378T, 378S, 380Q, 382V, 382G, 383R, 383N, 384I, 384T, 385R, 386R, 386K, 387S, 387T, 389T, 389K, 389R, 390S, 392E, 392R, 393N, 394A, 395A, 395S, 396S, 396L, 397A, 397M, 398P, 399N, 400P, 401A, 401G, 403T, 404L, 408T, 411A, 412A, 414R, 415D, 415N, 416K, 416G, 418R, 418K, 418E, 419H, 420R, 421T, 421S, 421D, 422A, 424L, 426T, 428L, 433R, 433P, 434Y, 434S, 434H, 438R, 439R, 440R, 440N, 443R, 444F, 444P, 445S, 446A, 447E and 447N of the Fc region, as compared to the parent polypeptide, wherein the numbering of the amino acids in the Fc region is that of the EU index as in Kabat.

In another embodiment, a variant according to the present invention comprises:

(i) at least one combination of amino acid modifications selected from the group consisting of:

250A/434Y, 307P/434Y, 230T/434S, 264E/396L, 378V/434Y, 378V/434S, 264E/378V, 264E/434S, 315D/330V, and 315D/434Y; and (ii) at least one amino acid modifications selected from the group consisting of 226G, 227L, 228L, 228R, 230S, 230T, 230L, 231T, 241L, 243L, 250A, 256N, 259I, 264E, 265G, 267R, 290E, 294del, 303A, 305A, 307P, 307A, 308I, 315D, 322R, 325S, 327V, 330V, 342R, 347R, 352S, 361D, 362R, 362E, 370R, 378V, 378T, 382V, 383N, 386R, 386K, 387T, 389T, 389K, 392R, 395A, 396L, 397M, 403T, 404L, 415N, 416K, 421T, 426T, 428L, 433R, 434Y, 434S and 439R of the Fc region, as compared to the parent polypeptide, wherein the numbering of the amino acids in the Fc region is that of the EU index as in Kabat and with the proviso that the modifications (i) does not occur at the same amino acid position as the modification (ii).

In some embodiments, the said variant comprises at least one amino acid combination of modifications selected from the group consisting of:

226G/315D/330V, 226G/315D/434Y, 226G/330V/434Y, 230L/264E/378V, 230T/264E/378V, 230T/264E/434S, 230S/315D/434Y, 230T/315D/434Y, 230T/389T/434S, 241L/264E/434S, 241L/264E/378V, 241L/264E/307P, 241L/307P/378V, 250A/389K/434Y, 256N/378V/434Y, 259I/315D/434Y 264E/378T/396L, 264E/378V/416K, 294del/307P/434Y, 264E/307P/378V, 264E/396L/434S, 264E/378V/434S, 305N315D/330V, 305A/315D/434Y, 305A/330V/434Y, 307P/378V/434Y, 315D/330V/382V, 315D/330V/389T, 315D/378V/434Y, 315D/389T/434Y, 315D/362R/434Y, 315D/382V/434Y, 315D/330V/434Y 330V/382V/434Y, 330V/389T/434Y, and 378V/383N/434Y of the Fc region, wherein the numbering of the amino acids in the Fc region is that of the EU index as in Kabat.

The said variant may comprise at least one additional modification selected from the group consisting of 226G, 226Y, 227S, 227L, 228R, 228L, 230S, 230T, 230L, 230A, 230Q, 231T, 231V, 233D, 234R, 239A, 241L, 241Y, 241R, 243L, 246R, 250A, 252L, 256N, 259I, 264A, 264E, 264M, 265G, 265N, 267N, 267R, 269D, 269G, 270N, 270E, 276S, 284L, 285Y, 288R, 2891, 290R, 290E, 291S, 291Q, 292W, 294del, 297D, 298G, 298N, 299M, 299A, 299K, 301C, 302A, 303A, 3031, 305A, 307P, 307A, 307N, 308I, 309P, 311R, 315D, 317R, 320T, 320E, 322R, 325S, 327V, 327T, 330V, 330T, 332V, 334E, 334R, 335A, 338R, 340E, 342R, 342E, 342K, 343S, 345Q, 345G, 347R, 350A, 352S, 354P, 355Q, 355G, 356N, 359A, 360N, 360R, 361D, 361S, 362R, 362E, 369A, 370R, 371D, 375A, 375G, 378V, 378T, 378S, 380Q, 382V, 382G, 383R, 383N, 384I, 384T, 385R, 386R, 386K, 387S, 387T, 389T, 389K, 389R, 390S, 392E, 392R, 393N, 394A, 395A, 395S, 396S, 396L, 397A, 397M, 398P, 399N, 400P, 401A, 401G, 403T, 404L, 408T, 411A, 412A, 414R, 415D, 415N, 416K, 416G, 418R, 418K, 418E, 419H, 420R, 421T, 421S, 421D, 422A, 424L, 426T, 428L, 433R, 433P, 434Y, 434S, 434H, 438R, 439R, 440R, 440N, 443R, 444F, 444P, 445S, 446A, 447E and 447N of the Fc region, as compared to the parent polypeptide, wherein the numbering of the amino acids in the Fc region is that of the EU index as in Kabat.

In another embodiment, a variant according to the present invention comprises:

(i) at least one combination of amino acid modifications selected from the group consisting of:

226G/315D/330V, 226G/315D/434Y, 226G/330V/434Y, 230L/264E/378V, 230T/264E/378V, 230T/264E/434S, 230S/315D/434Y, 230T/315D/434Y, 230T/389T/434S, 241L/264E/434S, 241L/264E/378V, 241L/264E/307P, 241L/307P/378V, 250A/389K/434Y, 256N/378V/434Y, 259I/315D/434Y 264E/378T/396L, 264E/378V/416K, 294del/307P/434Y, 264E/307P/378V, 264E/396L/434S, 264E/378V/434S, 305A/315D/330V, 305N315D/434Y, 305A/330V/434Y, 307P/378V/434Y, 315D/330V/382V, 315D/330V/389T, 315D/389T/434Y, 315D/362R/434Y, 315D/378V/434Y, 315D/382V/434Y, 315D/330V/434Y 330V/382V/434Y, 330V/389T/434Y, and 378V/383N/434Y; and (ii) at least one amino acid modification selected from the group consisting of 226G, 227L, 228L, 228R, 230S, 230T, 230L, 231T, 241L, 243L, 250A, 256N, 259I, 264E, 265G, 267R, 290E, 294del, 303A, 305A, 307P, 307A, 308I, 315D, 322R, 325S, 327V, 330V, 342R, 347R, 352S, 361D, 362R, 362E, 370R, 378V, 378T, 382V, 383N, 386R, 386K, 387T, 389T, 389K, 392R, 395A, 396L, 397M, 403T, 404L, 415N, 416K, 421T, 426T, 428L, 433R, 434Y, 434S and 439R of the Fc region, as compared to the parent polypeptide, wherein the numbering of the amino acids in the Fc region is that of the EU index as in Kabat and with the proviso that the modifications (i) does not occur at the same amino acid position as the modification (ii).

In other embodiments, the said variant comprises at least one amino acid combination of modifications selected from the group consisting of:

226G/315D/434Y, 230S/315D/434Y, 230T/315D/434Y, 230T/264E/434S, 230T/389T/434S, 241L/264E/378V, 241L/264E/434S, 250A/389K/434Y, 256N/378V/434Y, 259I/315D/434Y, 264E/378T/396L, 264E/378V/416K, 264E/378V/434S, 264E/396L/434S, 294del/307P/434Y, 307P/378V/434Y, 315D/330V/434Y, 315D/378V/434Y, 315D/382V/434Y and 378V/383N/434Y of the Fc region, wherein the numbering of the amino acids in the Fc region is that of the EU index as in Kabat.

The said variant may further comprise at least one additional modification selected from the group consisting of 226G, 226Y, 227S, 227L, 228R, 228L, 230S, 230T, 230L, 230A, 230Q, 231T, 231V, 233D, 234R, 239A, 241L, 241Y, 241R, 243L, 246R, 250A, 252L, 256N, 259I, 264A, 264E, 264M, 265G, 265N, 267N, 267R, 269D, 269G, 270N, 270E, 276S, 284L, 285Y, 288R, 2891, 290R, 290E, 291S, 291Q, 292W, 294del, 297D, 298G, 298N, 299M, 299A, 299K, 301C, 302A, 303A, 3031, 305A, 307P, 307A, 307N, 308I, 309P, 311R, 315D, 317R, 320T, 320E, 322R, 325S, 327V, 327T, 330V, 330T, 332V, 334E, 334R, 335A, 338R, 340E, 342R, 342E, 342K, 343S, 345Q, 345G, 347R, 350A, 352S, 354P, 355Q, 355G, 356N, 359A, 360N, 360R, 361D, 361S, 362R, 362E, 369A, 370R, 371D, 375A, 375G, 378V, 378T, 378S, 380Q, 382V, 382G, 383R, 383N, 384I, 384T, 385R, 386R, 386K, 387S, 387T, 389T, 389K, 389R, 390S, 392E, 392R, 393N, 394A, 395A, 395S, 396S, 396L, 397A, 397M, 398P, 399N, 400P, 401A, 401G, 403T, 404L, 408T, 411A, 412A, 414R, 415D, 415N, 416K, 416G, 418R, 418K, 418E, 419H, 420R, 421T, 421S, 421D, 422A, 424L, 426T, 428L, 433R, 433P, 434Y, 434S, 434H, 438R, 439R, 440R, 440N, 443R, 444F, 444P, 445S, 446A, 447E and 447N of the Fc region, as compared to the parent polypeptide, wherein the numbering of the amino acids in the Fc region is that of the EU index as in Kabat.

In another embodiment, a variant according to the present invention comprises:

(i) at least one combination of amino acid modifications selected from the group consisting of:

226G/315D/434Y, 230S/315D/434Y, 230T/315D/434Y, 230T/264E/434S, 230T/389T/434S, 241L/264E/378V, 241L/264E/434S, 250A/389K/434Y, 256N/378V/434Y, 259I/315D/434Y, 264E/378T/396L, 264E/378V/416K, 264E/378V/434S, 264E/396L/434S, 294del/307P/434Y, 307P/378V/434Y, 315D/330V/434Y, 315D/378V/434Y, 315D/382V/434Y and 378V/383N/434Y; and (ii) at least one amino acid modification selected from the group consisting of 226G, 227L, 228R, 228L, 230S, 230T, 230L, 231T, 241L, 243L, 250A, 256N, 259I, 264E, 265G, 267R, 290E, 294del, 303A, 305A, 307P, 307A, 308I, 315D, 322R, 325S, 327V, 330V, 342R, 347R, 352S, 361D, 362R, 362E, 370R, 378V, 378T, 382V, 383N, 386R, 386K, 387T, 389T, 389K, 392R, 395A, 396L, 397M, 403T, 404L, 415N, 416K, 421T, 426T, 428L, 433R, 434Y, 434S and 439R of the Fc region, as compared to the parent polypeptide, wherein the numbering of the amino acids in the Fc region is that of the EU index as in Kabat and with the proviso that the modifications (i) does not occur at the same amino acid position as the modification (ii).

In all previously cited embodiments, the said variant preferably has from 1 to 20, more preferably from 1 to 10 amino acid modifications as compared to the parent polypeptide.

In an alternate embodiment, the said variant comprises one combination of amino acid modifications selected from the group consisting of 307A/315D/330V/382V/389T/434Y, 307A/315D/382V/389T/434Y, 256N/378V/383N/434Y, 256N/378V/434Y, 315D/330V/361D/378V/434Y, 315D/361D/378V/434Y, 259I/315D/434Y, 230S/315D/428L/434Y, 241L/264E/307P/378V/433R, 250A/389K/434Y, 305A/315D/330V/395A/434Y, 264E/386R/396L/434S/439R, 315D/330V/362R/434Y, 294del/307P/434Y, 305N315D/330V/389K/434Y, 315D/327V/330V/397M/434Y, 230T/241L/264E/265G/378V/421T, 264E/396L/415N/434S, 227L/264E/378V/434S, 264E/378T/396L, 230T/315D/362R/426T/434Y, 226G/315D/330V/434Y, 230L/241L/243L/264E/307P/378V, 250A/315D/325S/330V/434Y, 290E/315D/342R/382V/434Y, 241L/315D/330V/392R/434Y, 241L/264E/307P/378V/434S, 230T/264E/403T/434S, 264E/378V/416K, 230T/315D/362E/434Y, 226G/315D/434Y, 226G/315D/362R/434Y, 226G/264E/347R/370R/378V/434S, 308I/315D/330V/382V/434Y, 230T/264E/378V/434S, 231T/241L/264E/378T/397M/434S, 230L/264E/378V/434S, 230T/315D/330V/386K/434Y, 226G/315D/330V/389T/434Y, 267R/307P/378V/421T/434Y, 230S/315D/387T/434Y, 230S/264E/352S/378V/434S and 230T/303A/322R/389T/404L/434S of Fc region, wherein the numbering of the amino acids in the Fc region is that of the EU index as in Kabat.

In other embodiment, the said variant comprises one combination of amino acid modifications selected from the group consisting of 256N/378V/434Y, 307A/315D/330V/382V/389T/434Y, 256N/378V/383N/434Y, 315D/330V/361D/378V/434Y, 259I/315D/434Y and 230S/315D/428L/434Y.

A further object of the invention is to provide polypeptide variants with increased binding for FcRn as compared to their parent polypeptides and comprising a Fc variant selected from the group consisting of 307A/315D/330V/382V/389T/434Y, 307A/315D/382V/389T/434Y 256N/378V/383N/434Y, 315D/330V/361D/378V/434Y, 315D/361D/378V/434Y 259I/315D/434Y, 230S/315D/428L/434Y, 241L/264E/307P/378V/433R, 250N389K/434Y, 256N/378V/434Y, 305A/315D/330V/395A/434Y, 264E/386R/396L/434S/439R, 315D/330V/362R/434Y, 294del/307P/434Y, 305N315D/330V/389K/434Y, 315D/327V/330V/397M/434Y, 230T/241L/264E/265G/378V/421T, 264E/396L/415N/434S, 227L/264E/378V/434S, 264E/378T/396L, 230T/315D/362R/426T/434Y, 226G/315D/330V/434Y, 230L/241L/243L/264E/307P/378V, 250A/315D/325S/330V/434Y, 290E/315D/342R/382V/434Y, 241L/315D/330V/392R/434Y, 241L/264E/307P/378V/434S, 230T/264E/403T/434S, 264E/378V/416K, 230T/315D/362E/434Y, 226G/315D/434Y, 226G/315D/362R/434Y, 226G/264E/347R/370R/378V/434S, 308I/315D/330V/382V/434Y, 230T/264E/378V/434S, 231T/241L/264E/378T/397M/434S, 230L/264E/378V/434S, 230T/315D/330V/386K/434Y, 226G/315D/330V/389T/434Y, 267R/307P/378V/421T/434Y, 230S/315D/387T/434Y, 230S/264E/352S/378V/434S and 230T/303A/322R/389T/404L/434S, wherein the numbering of the amino acids in the Fc region is that of the EU index as in Kabat. In some other embodiments, the polypeptide variant with increased binding for FcRn as compared to its parent polypeptide comprises a Fc variant selected from the group consisting of 256N/378V/434Y, 307A/315D/330V/382V/389T/434Y, 256N/378V/383N/434Y, 315D/330V/361D/378V/434Y, 259I/315D/434Y and 230S/315D/428L/434Y.

For all the above-mentioned variants according to the invention, the Fc region of their parent polypeptides may derive from the Fc regions of wild-type IgGs (e.g "lower hinge-CH2-CH3") and fragments thereof. In a more preferred embodiment, the Fc region of parent polypeptides derives from the human IgG subclasses namely IgG1, IgG2, IgG3 and IgG4. In another preferred embodiment, the Fc region of the parent polypeptides is selected from the group consisting of the wild-type IgG1 Fc region (SEQ ID NO:1), the wild-type IgG2 Fc region (SEQ ID NO:2), the wild-type IgG3 Fc region (SEQ ID NO:3) and the wild-type IgG4 Fc region (SEQ ID NO:4).

In this context, another object of the invention is a polypeptide comprising a IgG1 Fc variant wherein said IgG1 Fc variant comprises at least one amino acid modification as compared to the wild-type sequence of IgG1 Fc (SEQ ID NO:1) and displays an increased binding to FcRn as compared to the wild-type IgG1 Fc with the proviso that the sequence of said IgG1 Fc variant is not SEQ ID NO:2, SEQ ID NO:3 and SEQ ID NO:4.

Another object of the invention is a polypeptide comprising an IgG2 Fc variant wherein said IgG2 Fc variant comprises at least one amino acid modification as compared to the wild-type sequence of IgG2 Fc (SEQ ID NO:2) and displays an increased binding to FcRn as compared to the wild-type IgG2 Fc with the proviso that the sequence of said IgG2 Fc variant is not SEQ ID NO:1, SEQ ID NO:3 and SEQ ID NO:4.

An additional object of the invention is a polypeptide comprising an IgG3 Fc variant wherein said IgG3 Fc variant comprises at least one amino acid modification as compared to the wild-type sequence of IgG3 Fc (SEQ ID NO:3) and displays an increased binding to FcRn as compared to the wild-type IgG3 Fc with the proviso that the sequence of said IgG3 Fc variant is not SEQ ID NO:1, SEQ ID NO:2 and SEQ ID NO:4.

Another object of the invention is a polypeptide comprising an IgG4 Fc variant wherein said IgG4 Fc variant comprises at least one amino acid modification as compared to the wild-type sequence of IgG4 Fc (SEQ ID NO:4) and displays an increased binding to FcRn as compared to the wild-type IgG4 Fc with the proviso that the sequence of said IgG2 Fc variant is not SEQ ID NO:1, SEQ ID NO:3 and SEQ ID NO:2.

In preferred embodiments, the at least one amino acid modification comprised in the IgG1, IgG2, IgG3 or IgG4 Fc variant polypeptides are selected from the group of amino acid modifications and combinations of amino acid modifications that are described above in the instant specification when generally defining the variant of a polypeptide comprising an Fc region and having an increased binding to FcRn as compared to the corresponding parent polypeptide.

As described above, a variant according to the invention exhibits an increased binding to FcRn as compared to the corresponding parent polypeptide. In one embodiment, the effector functions and the other binding properties of the said variant are similar to that of the corresponding parent. The said variant may particularly exhibit no significant change in binding to Fc-gamma receptors or C1q as compared to its parent polypeptide.

In another embodiment, the said variant has an increased binding to FcRn combined with one or more altered effector functions and/or binding to Fc ligands (other than FcRn).

As illustrated in Example 2, the variant of the invention may have an increased binding to FcRn combined with unaltered binding to a FcγR, in particular to FcγRIIIa, ADCC (Antibody-Dependent Cell-mediated Cytotoxicity) activity and CDC (Complement-Dependent Cytotoxicity) activity as compared to the polypeptide variant. The variant of the invention may also have an increased binding to FcRn combined with ADCC and CDC activities which are at least similar to that of its polypeptide parent. In some other cases, the variant of the invention may have an increased binding to FcRn combined with at least one reduced effector activity selected from ADCC and CDC as compared to its polypeptide parent.

ADCC and CDC activities may be assessed by well-known methods of the prior art such as those described in Example 2 parts IV.2 and IV.3 of the present specification.

The binding to FcγR may be assessed by conventional methods such as SPR or ELISA assay.

A further object of the invention is to provide variants which optionally comprise additional amino acid modifications which differ from those cited previously with the proviso that the resulting variants have an increased binding to FcRn as compared to the parent polypeptide.

Accordingly, the Fc modifications of the present invention may be combined with other Fc modifications which are known to increase the Fc affinity for FcRn (see for example the references cited in the part of the present application dedicated to the description of the related art).

Alternatively, the Fc modifications may be combined with other Fc modifications including but not limited to modifications that alter effector function or interaction with one or more Fc ligands. As a consequence, such variants may display an increased binding to FcRn combined with an altered binding to one Fc ligand (other than FcRn) or/and an altered effector function as compared to the parent polypeptide.

Fc ligands include but are not limited to FcγRs (Fcgamma. receptors), C1q, C3, mannan binding lectin, mannose receptor, staphylococcal protein A, streptococcal protein G, and viral FcγRs. Fc ligands also include Fc receptor homologs (FcRH), which are a family of Fc receptors that are homologous to the FcgammaRs (Davis et al., 2002, Immunological Reviews 190:123-136).

By "effector function" as used herein is meant a biochemical or cellular event that results from the interaction of an antibody Fc region with an Fc receptor or ligand. Effector functions include but are not limited to ADCC (Antibody-Dependent Cell-mediated Cytotoxicity), ADCP (Antibody-Dependent Cell-mediated Phagocytosis), and CDC (Complement Dependent Cytotoxicity).

The variants of the present invention encompass any polypeptide comprising an Fc region and displaying an increased binding affinity for FcRn as compared to its parent polypeptide with the proviso that the said polypeptide differs from its parent polypeptide in virtue of at least one amino acid modification or combination of amino acid modifications in the Fc region. The modifications and the combinations of amino acid modifications of interest are those described above when giving general features of the variants according to the invention.

The variants (and thus the parent polypeptides) include, but are not limited to, antibodies, Fc fusion proteins, Fc conjugates, isolated Fc and their fragments respectively. In particular, the variants can be an Fc-comprising binding protein. In other words, the variants comprising (i) an Fc variant and (ii) a binding polypeptide domain which is able to specifically bind to a given molecule.

In one embodiment, the polypeptide variants of the invention are selected from the group consisting of Fc-fusion protein variants and Fc-conjugate variants. Fc-fusion protein and Fc-conjugates consist of an Fc region linked to a partner. The Fc region can be linked to its partner with or without a spacer.

According to the present invention, an Fc fusion protein is a protein encoded by a single gene and comprises a protein, a polypeptide or a small peptide linked to an Fc region. An Fc fusion protein optionally comprises a peptide spacer. Virtually any protein or small molecule may be linked to Fc regions to generate an Fc fusion. Protein fusion partners may include, but are not limited to, the variable region of any antibody, a polypeptide derived from a variable region of any antibody, the target-binding region of a receptor, an adhesion molecule, a ligand, an enzyme, a cytokine, a chemokine, or some other protein or protein domain. In particular the Fc-fusion protein can be an immunoadhesin i.e antibody-like protein which combines the binding domain of a heterologous "adhesion" protein (i.e receptor, ligand or enzyme) with a fragment of immunoglobulin constant domain (i.e. an Fc region) (see for a review about immunoadhesins, Ashkenazi A, Chamow S M. 1997, Curr Opin Immunol.; 9 (2):195-200).

Small peptide fusion partners may include, but are not limited to, any therapeutic agent that directs the Fc fusion to a therapeutic target. Such targets may be any molecule, preferably an extracellular receptor that is implicated in disease.

According to the present invention, an Fc conjugate results from the chemical coupling of a Fc region with a conjugate partner. The conjugate partner can be proteinaceous or non-proteinaceous. The coupling reaction generally uses functional groups on the Fc region and on the conjugate partner. Various linkers are known in the art to be appropriate for the synthesis of conjugate; for example, homo- or hetero-bifunctional linkers are well known (see, Pierce Chemical Company catalog, 2005-2006, technical section on cross-linkers, pages 321-350, incorporated herein by reference.

Suitable conjugate partners include, but are not limited to, therapeutic polypeptides, labels (for example of labels, see further below), drugs, cytotoxic agents, cytotoxic drugs (e.g., chemotherapeutic agents), toxins and active fragments of such toxins. Suitable toxins and their corresponding fragments include, but are not limited to, diptheria A chain, exotoxin A chain, ricin A chain, abrin A chain, curcin, crotin, phenomycin, enomycin and the like. A cytotoxic agent may be any radionuclide which can be directly conjugated to the Fc variant or sequestrated by a chelating agent which is covalently attached to the Fc variant. In additional embodiments, the conjugate partners can be selected from the group consisting of calicheamicin, auristatins, geldanamycin, maytansine, and duocarmycins and analogs; (for the latter, see U.S. 200310050331, hereby incorporated by reference in its entirety).

Such variants of interest may have an increased binding to FcRn at lowered pH (e.g at about pH 6), and substantially unmodified binding at higher pH (e.g. at about pH 7.4). Of particular interest are Fc-fusion protein and Fc-conjugate variants which display increased in vivo half-lives as compared to parent polypeptides.

In a preferred embodiment, the polypeptide variant of the present invention is a variant antibody of a parent antibody. The term "antibody" is used herein in the broadest sense. According to the present invention, "antibody" refers to any polypeptide which at least comprises (i) a Fc region and (ii) a binding polypeptide domain derived from a variable domain of an immunoglobulin. The said binding polypeptide domain is able to bind specifically one given target antigen or a group of target antigens. A binding polypeptide domain which derives from a variable region of an immunoglobulin comprises at least one or more CDRs. Herein, antibodies include, but are not limited to, full-length immunoglobulins, monoclonal antibodies, multi-specific antibodies, Fc-fusion protein comprising at least one variable region, synthetic antibodies (sometimes referred to herein as "antibody mimetics"), chimeric antibodies, humanized antibodies and fully human antibodies. Antibodies also encompass antibody-fusion proteins, antibody conjugates and fragments of each respectively. Accordingly a variant antibody of the invention comprises, in its Fc region, at least one amino acid modification or combination of modifications above-cited that increase its binding affinity for FcRn as compared to its parent antibody. Of particular interest are antibody variants that display increased binding affinity to FcRn at lowered pH (e.g at about pH 6), and have substantially unmodified binding at higher pH (e.g. at about pH 7.4). Furthermore, of particular interest are antibody variants which have increased in vivo half-lives as compared to parent polypeptides.

In one embodiment, a variant antibody of the invention is selected from the group consisting of variants of parent full-length antibodies. By "full length antibody" herein is meant the structure that constitutes the natural biological form of an antibody, including variable and constant regions. The parent polypeptide of a full-length antibody variant of the present invention can be a wild-type antibody, a mutant of a wild-type antibody (e.g. comprising pre-existing modifications), an engineered version of a wild-type antibody (e.g. for example a chimeric, a humanized antibody or a fully human antibody, see further below), this list not being limitative. The structure of a full-length antibody is generally a tetramer except for some mammals such as llamas and camels in which some immunoglobulins are dimers. Each tetramer is typically composed of two identical pairs of polypeptide chains, each pair having one "light" (typically having a molecular weight of about 25 kDa) and one "heavy" chain (typically having a molecular weight of about 50-70 kDa).

Examples of full-length antibodies are human immunoglobulins which encompass IgM, IgD, IgG, IgA and IgE classes.

In preferred embodiments, the said full-length antibody variant is selected from the group consisting of variants of IgGs.

In more preferred embodiments, the said full-length antibody variant is selected from the group consisting of variants of human IgG1, IgG2, IgG3 and IgG4 with the proviso that the said Fc region sequence of said variant is not SEQ ID NO:1, SEQ ID NO:2, SEQ ID NO:3 and SEQ ID NO:4.

The said IgG variant comprises one or more amino acid modifications as compared to its parent IgG, said one or more modifications or combinations of amino acid modifications are those previously described in the present specification when generally defining the variants of a polypeptide comprising a Fc region and having an increased binding to FcRn as compared to the corresponding parent polypeptide.

In another embodiment, the said antibody variant is selected from the group consisting of Fc-fusion protein comprising a binding polypeptide domain derived from a variable domain of an immunoglobulin. Of particular interest are antibodies that comprise (a) a Fc variant of the inventions, and (b) one of the following binding polypeptide domains derived from a variable region of an immunoglobulin (i.e. which comprise at least one CDR): (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) isolated CDR regions, (v) F(ab')2 fragments, a bivalent fragment comprising two linked Fab fragments (vi) single chain Fv molecules (scFv), wherein a VH domain and a VL domain are linked by a peptide linker which allows the two domains to associate to form an antigen binding site, (vii) bispecific single chain Fv and (viii) "diabodies" or "triabodies", multivalent or multispecific fragments constructed by gene fusion, this list not being limitative.

In another embodiment, the antibody is a minibody. Minibodies are minimized antibody-like proteins comprising a scFv joined to a CH3 domain (Hu et al., 1996, Cancer Res. 56:3055-3061, incorporated by reference herein in its entirety). In some cases, the scFv can be joined to a full-length Fc region (De Lorenzo et al., 2005, Carcinogenesis 26:1890-1895, incorporated by reference herein its entirety), and may also include the hinge region or fragment thereof.

In one embodiment, the antibodies of the invention are selected from the group of multispecific antibodies, and notably from the group of bispecific antibodies which are sometimes referred to as "diabodies". These antibodies bind to two (or more) different antigens. Diabodies can be manufactured in a variety of ways known in the art (Holliger and Winter, 1993, Current Opinion Biotechnol. 4:446-449, incorporated by reference herein in its entirety), e.g., chemically prepared or derived from hybridomas.

In some embodiments, the scaffold components of the antibody variants can be a mixture from different species. Such antibody variant may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a non-human animal, generally the mouse (or rat, in some cases) and the constant region(s) from a human. For the most part, humanized antibodies are chimeric antibodies that contain minimal sequence derived from non human immunoglobulin. Generally, in a humanized antibody, the entire antibody, except the CDRs, is encoded by a polynucleotide of human origin or is identical to a human antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018; Jones, 1986, Nature 321:522-525; Verhoeyen et al., 1988, Science 239: 1534-1536, all incorporated by reference herein in their entirety. The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system (Roque et al., 2004, Biotechnol. Prog. 20:639-654, incorporated by reference herein in its entirety). A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all incorporated by reference in their entirety). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9; Presta et al., 1997, Cancer Res. 57 (20):4593-9; Gorman et al., 1991, Proc. Natl. Acad. Sci. USA 88:4181-4185; O'Connor et al., 1998, Protein Eng 11:321-8, all incorporated by reference in their entirety. Humanization or other methods of reducing the immunogenicity of nonhuman antibody variable regions may include resurfacing methods, as described for example in Roguska et al., 1994, Proc. Natl. Acad. Sci. USA 91:969-973, incorporated by reference herein in its entirety.

In one embodiment, the said antibody variant is a fully human antibody with at least one amino acid modification as outlined herein. "Fully human antibody" or "complete human antibody" refers to an antibody entirely comprising sequences originating from human genes. In some cases this may be human antibodies that have the gene sequence of an antibody derived from a human chromosome with the modifications outlined herein. Alternatively, the components of the antibody may be human but not be derived from a single gene. Thus, for example, human CDRs from one antibody can be combined with sequences, such as scaffold sequences, from one or more human antibodies. For example, a variety of germline sequences can be combined to form a human antibody or human scaffold (e.g. for use in humanized or chimeric sequences as outlined above), as well as U.S. patent application Ser. No. 11/022,289, incorporated herein by reference in its entirety.

In certain embodiments, the antibody variant of the invention is selected from the group consisting of chimeric IgGs, humanized IgGs and fully-human IgGs.

Covalent modifications of antibodies are also included within the scope of this invention, and are generally, but not always, done post-translationally. Such modifications include, but are not limited to, glycosylations, labelling and conjugation.

Accordingly, in some embodiments, the polypeptide variants disclosed herein can be modified to include one or more engineered glycoforms. By "engineered glycoform" as used herein is meant a carbohydrate composition that is covalently attached to the polypeptide comprising the Fc variant, wherein said carbohydrate composition differs chemically from that of a polypeptide parent. Engineered glycoforms may be useful for a variety of purposes, including but not limited to enhancing or reducing effector function. The engineered glycoforms can be attached at any amino acid of the variant sequence. In a preferred embodiment, the said glycoforms are attached at amino acids of the Fc region.

Engineered glycoforms may be generated by a variety of methods known in the art (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. No. 6,602,684; U.S. Ser. Nos. 10/277,370; 10/113,929; WO 00/61739A1; WO 01/29246A1; WO 02/31140A1; WO 02/30954A1, WO 01/77181, all incorporated by reference in their entirety; (Potelligent® technology [Biowa, Inc., Princeton, N.J.]; GlycoMAb® glycosylation engineering technology [Glycart Biotechnology AG, Zuerich, Switzerland]). Many of these techniques are based on controlling the level of fucosylated and/or bisecting oligosaccharides that are covalently attached to the Fc region, for example by expressing the antibody variant in various organisms or cell lines, engineered or otherwise (for example Lec-13 CHO cells or rat hybridoma YB2/0 cells), by regulating enzymes involved in the glycosylation pathway (for example FUT8 [α1,6-fucosyltranserase] and/or (β1-4-N-acetylglucosaminyltransferase III [GnTIII]), or by modifying carbohydrate(s) after the antibody variant has been expressed.

Alternatively, engineered glycoform may refer to the antibody variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, CRC Crit. Rev. Biochem., pp. 259-306.

Removal of carbohydrate moieties present on the starting antibody may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131. Enzymatic cleavage of carbohydrate moieties on polypeptides can be achieved by the use of a variety of endo- and exo-glycosidases as described by Thotakura et al., 1987, Meth. Enzymol. 138:350. Glycosylation at potential glycosylation sites may be prevented by the use of the compound tunicamycin as described by Duskin et al., 1982, J. Biol. Chem. 257:3105. Tunicamycin blocks the formation of protein-N-glycoside linkages.

In some embodiments, the antibody variant of the invention is selected from the group consisting of chimeric IgGs, humanized IgGs and fully-human IgGs which comprise engineered glycoforms.

In an alternative embodiment, the covalent modification of the antibody variants of the invention comprises the addition of one or more labels. In some cases, these are considered antibody fusions. The term "labeling group" means any detectable label. In some embodiments, the labeling group is coupled to the antibody via spacer arms of various lengths to reduce potential steric hindrance. Various methods for labeling proteins are known in the art and may be used in performing the present invention.

In general, labels fall into a variety of classes, depending on the assay or on the diagnostic procedure in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc).

Specific labels include optical dyes, including, but not limited to, chromophores, phosphors and fluorophores, with the latter being specific in many instances. Fluorophores can be either fluorescent "small molecules" fluorescent, or fluorescent proteins.

In another embodiment, the antibody variants of the present invention may be fused to or conjugated to a protein or a small molecule which are not used as a labelling group as described above. Virtually any protein or small molecule may be linked to an antibody. Protein fusion partners may include, but are not limited to, the target-binding region of a receptor, an adhesion molecule, a ligand, an enzyme, a cytokine, a chemokine, or some other protein or protein domain. Small molecules include, but are not limited to drugs, cytotoxic agents (e.g., chemotherapeutic agents), toxins or active fragments of such toxins.

As described above, the antibody variants of the invention are able to bind specifically one target antigen or a group of target antigens. By "target antigen" as used herein is meant the molecule that is bound specifically by the variable region of a given antibody or immunoglobulin. A target antigen may be a protein, a carbohydrate, a lipid, or other chemical compound.

The choice of suitable antigen depends on the desired application. Virtually, any antigen may be targeted, for example membrane proteins comprising but not limited to the RhD antigen, CD3, CD4, CD19, CD20, CD22, CD25, CD28, CD32B, CD33, CD38, CD40, CD44, CD52, CD71 (transferrin receptor), CD80, CD86, CTLA-4, CD147, CD160, CD224, growth factor receptors like those belonging to the ErbB family of receptors ErbB1, ErbB2, ErbB3, ErbB4 (EGFR, HER2/neu, HER3, HER4), VEGF-R1, VEGF-R2, IGF-R1, PIGF-R, MHC class I and MHC class II molecules, e.g. HLA-DR, interleukin receptors like IL-1R, IL-2R alpha, IL-2R beta and IL-2R gamma, IL-6R, hormone receptors like Müllerian inhibitory substance type II receptor, LDL receptor, NKp44L, chemokine receptors like CXCR4 and CCR5, integrins, adhesion molecules like CD2, ICAM, EpCAM. The membrane proteins also include tumour markers like GD2, GD3, CA125, MUC-1, MUC-16, carcinoembryonic antigen (CEA), Tn, glycoprotein 72, PSMA, HMW-MAA. Antibodies of the invention can also target soluble proteins, including but not limited to cytokines (for instance IL-1 beta, IL-2, IL-6, IL-12, IL-23, TGF beta, TNF alpha, IFN gamma), chemokines, growth factors like VEGF-A, EGF, PIGF, PDGF, IGF, hormones, bacterial toxins and toxins of other origin like botulinus toxin, ricin, B. anthracis protective antigen, B. anthracis lethal factor, B. anthracis edema factor, shigatoxins 1 and 2, viral antigens from different viruses, for example pathogenic viruses, an inhibitory antibody, including a FVIII inhibitory antibody.

In a preferred embodiment, the variant of the present invention may target CD20. In this case, the parent polypeptide can be selected from: EMAB6 or EMAB603 (see WO2006064121), RITUXIMAB (Rituxan®, IDEC/Genentech/Roche) (see for example U.S. Pat. No. 5,736,137, incorporated by reference in its entirety), HUMAX®-CD20, described in U.S. Pat. No. 5,500,362 incorporated by reference in its entirety, AME-133 (Applied Molecular Evolution), hA20 (Immunomedics, Inc.), HumaLYM (Intracel), and PRO70769 (PCT/US2003/040426, entitled "Immunoglobulin Variants and Uses Thereof", incorporated by reference in its entirety).

In another embodiment, the variant of the present invention may target RhD antigen. In this case, the parent polypeptide can be selected from EMAB2 (see FR 03 12 229), Sym001 (Symphogen A/S) or MonoRho (ZLB, Zurich).

The parent polypeptide may also be Avastin® (anti-VEGF), Remicade® (anti-TNF-α), Erbitux®, Vectibix® (anti-EGFR), Tysabri® (anti-alpha4 chain of integrine), Herceptin® (anti-HER2/neu), the list not being limitative.

The present application also provides variants that display an increased binding to FcRn combined with another optimized property selected from a variety of well-known therapeutically relevant properties. The most preferred property that may be optimized is the in vivo half-life. To display an increased in vivo half-life, the variant should exhibit increased binding affinity to FcRn at lower pH, such as the pH associated with endosomes, e.g. pH 6.0, while maintaining the reduced affinity at higher pH, such as 7.4, to allow increased binding to FcRn into endosomes but normal release rates (Dall'Acqua et al., 2002, J. Immunol. 169: 5171-5180; Gurbaxani et al., 2006, Mol Immunol. 43 (9):1462-73). Similarly, these variants with such modulated FcRn binding may optionally have other desirable properties, such as modulated FcγR binding. In one additional embodiment, the variants are optimized to possess enhanced affinity for a human activating FcγR, preferably FcγRIIIa in addition to the FcRn binding profile. In an alternate embodiment, the variants are optimized to have increased affinity for FcRn and increased or decreased affinity for a human FcγR, including but not limited to FcγRI, FcγRIIa, FcγRIIb, FcγRIIc, and FcγRIIIb including their allelic variations. In alternative embodiments, the variants of the present invention may optionally have increased (or decreased) effector functions as well as an increased serum half-life. In particularly preferred embodiments, a variant of the invention may have increased ADCC activity and/or increased binding to a FcγR as well as increased serum half-life as compared to its polypeptide parent. In other embodiments, the variant of the invention may further have an increased CDC activity as compared to its polypeptide parent.

The variants may find use in a wide range of products. In one embodiment the variant is a therapeutic, a diagnostic, or a research reagent, preferably a therapeutic.

Since they display increased binding to FcRn, the variant of the invention are anticipated to have longer in vivo half-lives, more precisely longer in vivo serum half-lives than their parent polypeptides. As a consequence, such variants have useful applications as parent polypeptide substitutes when the parent polypeptide is too rapidly cleared from the blood circulation or for use in the treatment of chronic or long-term diseases which requires long half-life active principles.

When the variants are selected from the group of antibodies, they may find use in an antibody composition that is monoclonal or polyclonal. In a preferred embodiment, the said antibody variants are used to kill target cells that bear the target antigen, for example cancer cells. In an alternate embodiment, the variants are used to block, antagonize or agonize the target antigen, for example for antagonizing a cytokine or cytokine receptor, for neutralizing an infectious agent like a bacterium or a virus or a toxin, for example, a bacterial toxin. In an alternately preferred embodiment, the variants are used to block, antagonize or agonize the target antigen and kill the target cells that bear the target antigen.

In a preferred embodiment, a variant antibody is administered to a patient to treat an antibody-related disorder. A "patient" for the purposes of the present invention includes humans and other animals, preferably mammals and most preferably humans. By "antibody related disorder" or "antibody responsive disorder" or "condition" or "disease" herein are meant a disorder that may be ameliorated by the administration of a pharmaceutical composition comprising a variant of the present invention. Antibody related disorders include but are not limited to autoimmune diseases, immunological diseases, infectious diseases, inflammatory diseases, neurological diseases, pain, pulmonary diseases, hematological conditions, fibrotic conditions, and oncological and neoplastic diseases including cancer. By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia and lymphoid malignancies. Other conditions that may be treated include but are not limited to rheumatoid arthritis, juvenile rheumatoid arthritis, Crohn's disease, ulcerative colitis, Sjorgren's disease, multiple sclerosis, ankylosing spondylitis, asthma, allergies and allergenic conditions, graft versus host disease, and the like.

A further object of the invention is to provide pharmaceutical compositions comprising the said variant. The said formulations are prepared by mixing the polypeptide variant having the desired degree of purity with optional physiologically acceptable pharmaceutically acceptable carrier, excipients or stabilizers in the form of lyophilised formulations or aqueous solutions. (Remington's Pharmaceutical Sciences 16th edition, Osol, A. Ed., 1980, incorporated by reference herein in its entirety). Such pharmaceutical compositions are destined for treating a patient in need.

In order to treat a patient in need, a therapeutically effective dose of the variant may be administered. By "therapeutically effective dose" herein is meant a dose that produces the effects for which it is administered. The exact dose will depend on the purpose of the treatment, and will be ascertainable by one skilled in the art using known techniques. Dosages may range from 0.001 to 100 mg/kg of body weight or greater, for example 0.1, 1.0, 10, or 50 mg/kg of body weight, with 1 to 10 mg/kg being preferred. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

Administration of the pharmaceutical composition comprising a variant may be done in a variety of ways, including, but not limited to, orally, subcutaneously, intravenously, parenterally, intranasally, intraortically, intraocularly, rectally, vaginally, transdermally, topically (e.g., gels, salves, lotions, creams, etc.), intraperitoneally, intramuscularly, intrapulmonary.

Therapeutic described herein may be administered with other therapeutics concomitantly, i.e., the therapeutics described herein may be co-administered with other therapies or therapeutics, including for example, small molecules, other biologicals, radiation therapy, surgery, etc.

Another object of the present invention is to provide isolated nucleic acids encoding variants according to the invention. Most often, the DNA encoding the parent polypeptide is available or can be obtained. Consequently, the DNA encoding the variant of interest can be generated by altering the DNA encoding parent polypeptide thanks to a variety of methods known in the prior art. These methods include, but are not limited to site-directed mutagenesis, random mutagenesis, PCR mutagenesis and cassette mutagenesis. Amino acid substitutions are preferably made by site-directed mutagenesis (see, for example, Zoller and Smith, 1982, Nucl. Acids Res. 10:6487-6500; Kunkel, 1985, Proc. Natl. Acad. Sci USA 82:488, which are hereby incorporated by reference in their entireties).

Alternatively or additionally, the desired amino acid sequence encoding a polypeptide variant can be determined and thus can be generated synthetically by well-known methods of the prior art.

Once their encoding nucleic acids are obtained, the variants of the present invention can be made by any method known in the art. In one embodiment, the variant sequences (e.g. IgG variant sequences) are used to create nucleic acids that encode the member sequences, and that may then be cloned into host cells, expressed and assayed, if desired. These practices are carried out using well-known procedures, and a variety of methods that may find use in are described in Molecular Cloning—A Laboratory Manual, 3rd Ed. (Maniatis, Cold Spring Harbor Laboratory Press, New York, 2001), and Current Protocols in Molecular Biology (John Wiley & Sons), both incorporated by reference in their entirety. The nucleic acids that encode the variants may be incorporated into an expression vector in order to express the protein. Expression vectors typically include a protein operably linked, that is, placed in a functional relationship, with control or regulatory sequences, selectable markers, any fusion partners, and/or additional elements. The variant (e.g. IgG variants) of the present invention may be produced by culturing a host cell transformed with nucleic acid, preferably an expression vector, containing nucleic acid encoding the variant, under the appropriate conditions to induce or cause expression of the protein. A wide variety of appropriate host cell lines may be used, including but not limited to mammalian cells, bacteria, insect cells, and yeast. For example, a variety of mammalian cell lines that may find use are described in the ATCC cell line catalog, available from the American Type Culture Collection. Host cells may be, but not limited to, YB2/0 (YB2/3HL.P2.GII.IGAg.20 cell, deposit to the American Type Culture Collection, ATCC no CRL-1662), SP2/0, YE2/0, 1R983F, Namalwa, PERC6, CHO cell lines, particularly CHO-K-1, CHO-Lecl0, CHO-Lecl, CHO-Lecl3, CHO Pro-5, CHO dhfr-, Wil-2, Jurkat, Vero, Molt-4, COS-7, 293-HEK, BHK, KGH6, NSO, SP2/0-Ag 14, P3X63Ag8.653, C127, JC, LA7, ZR-45-30, hTERT, NM2C5, UACC-812 and the like. The methods of introducing exogenous nucleic acid into host cells are well known in the art, and will vary with the host cell used. In a preferred embodiment of the invention, the variant is expressed in YB2/0 cell, and is an anti-CD20 antibody, or an anti-RhD antibody.

In addition, a variant according to the present invention may be produced by a transgenic non-human animal or transgenic plant. Also, a transgenic non-human animal can be obtained by directly injecting a desired gene into a fertilized egg (Gordon et al., 1980 Proc Natl Acad Sci USA.; 77:7380-4). The transgenic non-human animals include mouse, rabbit, rat, goat, cow, cattle or fowl, and the like. A transgenic non-human animal having a desired gene can be obtained by introducing the desired gene into an embryonic stem cell and preparing the animal by an aggregation chimera method or injection chimera method (Manipulating the Mouse Embryo, A Laboratory Manual, Second edition, Cold Spring Harbor Laboratory Press (1994); Gene Targeting, A Practical Approach, IRL Press at Oxford University Press (1993)). Examples of the embryonic stem cell include embryonic stem cells of mouse (Evans and Kaufman, 1981, Nature; 292:154-156), rat, goat, rabbit, monkey, fowl, cattle and the like. In addition, a transgenic non-human animal can also be prepared using a clonal technique in which a nucleus into which a desired gene is introduced is transplanted into an enucleated egg (Ryan et al., 1997 Science; 278: 873-876; Cibelli et al., 1998 Science, 280: 1256-1258). The polypeptide variant can be produced by introducing DNA encoding the variant molecule into an animal prepared by the above method to thereby form and accumulate the variant molecule in the animal, and then collecting the polypeptide variant from the animal. The polypeptide variant may be made to be formed and accumulated in the milk, egg or the like of the animal.

Another object of the invention is to provide a method for identifying Fc variants which are optimized variants i.e. which have an increased binding for an Fc ligand as compared to a corresponding wild-type Fc region. Said method comprising the steps of:

(i) generating a nucleic acid library consisting of a set of nucleic acids encoding Fc variants (ii) producing the Fc variants by the expression of the nucleic acids comprised in the said library (iii) selecting among the Fc variants produced in step (ii), those which are able to bind to the Fc ligand (iv) measuring the binding property of the Fc variants selected in step (iii) and that of one Fc control for the Fc ligand and (v) selecting the Fc variants which display an increased binding for the Fc ligand as compared to the said Fc control The nucleic acid sequences comprised in the said nucleic acid library may be RNA or DNA. In a preferred embodiment, the said library comprises DNA sequences encoding Fc variants.

The Fc control is selected from the group consisting of wild-type Fc regions and known Fc variants which have binding property for the Fc ligand equal or higher than that of wild-type Fc.

The Fc ligand can be selected from FcRn and Fc.gamma.receptors, the list not being limitative.

In one embodiment, the nucleic acids of the library which encode Fc variants can be generated by altering the DNA sequence encoding for the wild-type Fc. As used herein, by "alter the nucleic acid sequence" is meant the introduction of mutations such as insertions, deletions or substitutions of nucleotides in a given nucleic acid sequence. Such mutations can be performed by well-known methods of the prior art. These methods include, but are not limited to, random mutagenesis, site-directed mutagenesis, PCR mutagenesis and cassette mutagenesis.

In a preferred embodiment, the library is generated by random mutagenesis based on the use of one or more low fidelity DNA polymerases. Such random mutagenesis is described in the PCT application WO0238756 incorporated by reference in its entirety. Accordingly, the library may be generated by the mixing of sub-libraries generated with one single polymerase or a specified combination of polymerases as described in the material and methods part of the example of the present application.

In another embodiment, the said nucleic acid library is generated by altering the DNA sequences encoding for a pool of pre-optimized Fc variants using one of the above-mentioned methods. Random mutagenesis is preferably used. Pre-optimized Fc variants are Fc variants which comprise at least one amino acid modification and display an increased binding for the Fc ligand as compared to the wild-type Fc. Pre-optimized Fc variants have preferably 1 to 4 amino acid modifications as compared to the wild-type Fc. Such pre-optimized Fc variants can be obtained from the screening of a library generated by mutation of a wild-type Fc. They also refer to Fc variants described in the prior art (for examples see above the first part of the present application dedicated to the description of the related art). The pool of pre-optimized Fc variants comprises several polypeptides, more preferably from about 2 to about 100 pre-optimized variants.

The libraries generated from pre-optimized variants enable to select more optimized Fc variants. For illustration see table 5 of the present application which shows the binding affinity of the best Fc variants selected from the screening of such a library.

Step (ii) i.e the expression of Fc variants can be performed by well-known methods using host cells as described previously. In a preferred embodiment the Fc library is expressed on the surface of bacteriophages (phage display) using standard procedures (see Smith, Science, 1985, 228: 1315).

Step (iii) can be performed by generating Fc variants-Fc ligand complexes and then separating the bound Fc variants from the unbound Fc variants. In order to perform this separation step, the Fc ligand may be advantageously immobilized on a solid support or should be able to be immobilized on a solid support during the process of step (iii). Examples of such procedures are described in Example 1 of the present application. The step (iii) preferably comprises several rounds of selection which enable to identify the most effective Fc ligands (for illustration see Example 2).

In step (iv), the binding properties of Fc variants for Fc ligand can be evaluated by well-known methods of the prior art. For example, the one skilled in the art may perform an appropriate ELISA. The variant is selected if its specific signal is at least 1.2-fold stronger than that of the Fc parent. Appropriate ELISA assays can be performed on isolated Fc or on Fc displayed on phage as illustrated in example II and in example IV of the present application.

As an alternative or for confirmation purpose, the one skilled in the art may determine the dissociation constant using Surface Plasmon Resonance (SPR) experiments as illustrated in the example IV of the present application. If the variant has a dissociation constant 3-fold lower then that of the Fc parent then the said variant is selected in step (v).

The present invention is further illustrated by, without on any way being limited to, the examples below.

EXAMPLES

Example 1

Identification of Fc Variants with Increased Binding to FcRn as Compared to Fc-Wild-Type and Binding Characterization of Said Variants I. Material and Methods I.1. Expression and Purification of Human FcRn The expression of soluble human FcRn using the baculovirus system was performed by GTP Technology (Labège, France) as previously described (Popov et al., Mol. Immunol. 33:521-530 (1996)). The α chain cDNA encoding the leader peptide and extracellular domains (codons 1-290) was tagged, with a TEV sequence and a 6× polyhistidine tag. The derivative α-chain and the β2 microglobulin chain were cloned into pFastBacDual under the P10 and polyhedrine promoters, respectively. A biotinylated version of FcRn (FcRn-biot) was prepared by chemical coupling with the FluoReporter® Biotin-XX Protein Labeling Kit, F2610 (Molecular Probes) according to the manufacturer's protocol. A fusion protein was also produced containing the β2 microglobulin chain and the α-chain fused to the amino terminal part of the bacteriophage β3 protein and the CVDE protein (FcRn-p3). More than 90% pure proteins were obtained after IgG-Sepharose and IMAC purification steps.

I.2. Construction of the Fc Libraries

Figure 1:
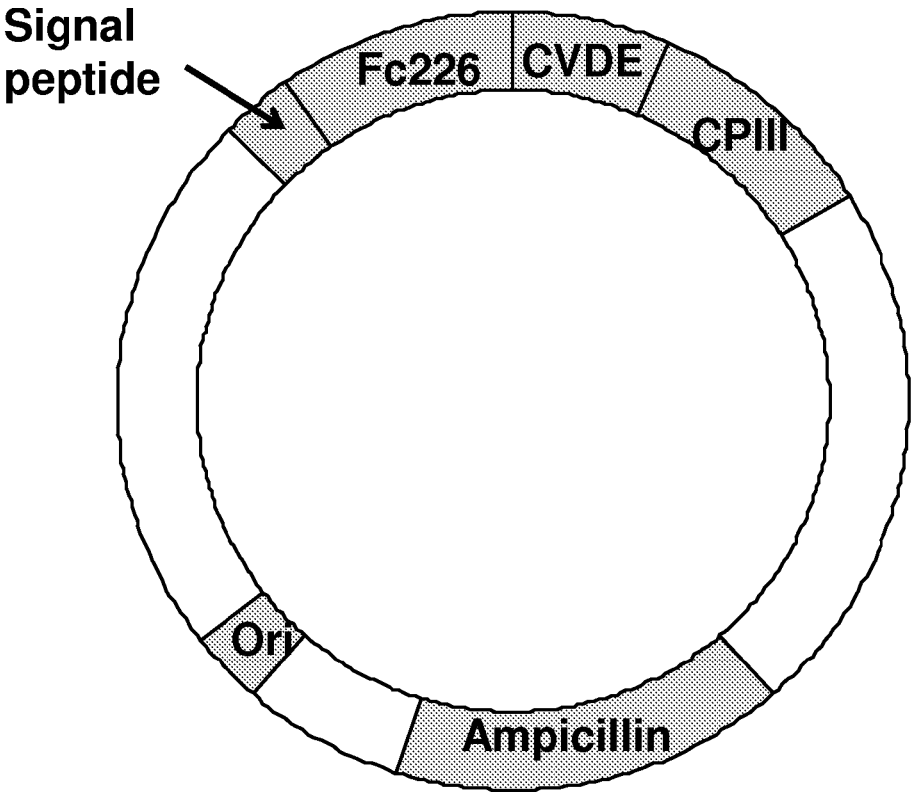
FIG. 1 shows the phagemid vector pMG58 in which human Fc gene encoding amino acid residues 226-447 (EU index as in Kabat) derived from a human IgG1 heavy chain (Fc226, SEQ no 1) was cloned into.

Human Fc gene encoding amino acid residues 226-447 (EU index as in Kabat) i.e. Fc polypeptide, derived from a human IgG1 heavy chain (SEQ no 1), (Poul M A et al., Eur. J. Immunol. 25 (7): 2005-2009 (1995) was cloned into the phagemid vector pMG58 (pMG58_Fc226, FIG. 1) as a BamHI/EcoRI fragment using standard PCR protocols. The said vector is depicted in FIG. 1. Several fully randomised libraries were generated using the MUTAGEN™ procedure (WO0238756) that uses low fidelity human DNA polymerases (mutases) to introduce random mutations homogeneously over the whole target sequence. Three distinct mutases (pol β, pol η and pol ι) were used in different conditions to create complementary mutational patterns. These human polymerases were produced and purified as described previously (Mondon et al., Biotechnol J. 2: 76-82 (2007), Emond et al. Protein Eng. Des. Sel. 21: 267-274 (2008)).

I.2-a. Mutagenesis with the Mutagen™ Process

The human Fc gene (Fc gene) was double replicated with mutases using the 5' primer MG_619: 5'-AGTACTGACTC-TACCTA<u>GGATCC</u>TGCCCACCGTGC-3' (SEQ ID No 5) and the 3' primer MG_621 5'-ACTGCTCGATGTCCGTAC-TATGCGGCCGCG<u>AATTC</u>-3' (SEQ ID No 6) (BamHI and EcoRI restriction sites are underlined and italic characters correspond to the non-specific tails). A mixture containing 0.6 μg of the pMG58_Fc226 plasmid as template (wild type Fc for Mut1 library or Fc variants for Mut2 library), primers MG_619 and MG_621 (250 nM each) and the appropriate replication buffer (detailed below) was treated for 5 min. at 95° C. and immediately cooled down to 4° C. to denature DNA strands. For pol β, replication buffer was 50 mM Tris HCl pH 8.8, 10 mM $MgCl_2$, 10 mM KCl, 1 mM DTT and 1% (v/v) glycerol. Replication buffer for pol η (or pol η and pol ι) was 25 mM Tris HCl pH 7.2, 5 mM $MgCl_2$, 10 mM KCl, 1 mM DTT and 2.5% (v/v) glycerol. After the denaturation step, mutagenic replications were performed by adding 50 μM dATP/dCTP, 100 μM dTTP/dGTP and 1 μg of pol β or 100 μM dNTPs and 1 μg of pol η (or pol η and pol ι, 1 μg of each mutase). The replication reaction was carried out at 37° C. for two hours. The replication products were then desalted and concentrated on microcon columns (Millipore).

1.2.b. Selective Amplification and Cloning of Mutated Fragments

The replication products previously obtained were amplified through a selective PCR with tail primers. The primers (MG_619 and MG_621) were designed with a tail that is non-complementary to the template allowing specific amplification of the DNA fragments synthesised by the mutases. A fraction of the replication products was added to a mixture containing the PCR buffer (20 mM Tris-HCl pH 8.4, 50 mM KCl), 1.5 mM $MgCl_2$, 10 pmol of the 5' and 3' primers, 200 μM dNTPs and 1.25 U Platinum Taq DNA polymerase (InvitroGen). The PCR cycles were as follow, first cycle: 2 min. at 94° C., 10 sec. at 64° C., 30 sec. at 75° C., 1 min at 94° C. and then 30 selective cycles: 20 sec. at 94° C. and 30 sec. at 75° C.

The amplified replication products were purified on 1% (w/v) agarose gels, digested with BamHI and EcoRI restriction enzymes and cloned into the pMG58 vector. The ligation mixtures were transformed in electrocompetent E. coli XL1-Blue cells and subsequently plated on solid 2YT medium (16 g/l peptones, 10 g/l yeast extract, 5 g/l NaCl, 15 g/l agar) supplemented with 100 μg/ml ampicillin and 1% (w/v) glucose. After growth, the number of colonies was determined to estimate the size of the libraries and 96 clones per library were randomly subjected to PCR and high throughput DNA sequencing. Cells were scrapped in 2YT medium with 15% glycerol, frozen and kept at −80° C.

For the first round of mutagenesis and screening (MS1), four different libraries were constructed. A first library was obtained using pol β on the wild type Fc gene and contained $3.2\times10^6$ clones (called Mut1.1). The DNA of this first library was used to generate the second and the third libraries, using respectively pol β ($3.8\times10^6$ clones, Mut1.2) and pol η and ι ($3.0\times10^6$ clones, Mut1.3). This strategy in two cumulative replication steps permitted to increase the mutation rate. The fourth library was generated with polymerase η alone on the wild type Fc gene ($1.0\times10^6$ clones, Mut1.4). Finally, these four libraries were proportionally mixed to obtain the final library called Mut1, representing $1.1\times10^7$ different clones.

For the second round of mutagenesis and screening (MS2), two different libraries were constructed using a DNA pool of 42 single and double mutants isolated during MS1 and having improved FcRn-binding by phage-ELISA. A first library was obtained using pol β ($1.9\times10^7$ clones, Mut2.1) and a second library with pol η ($1\times10^6$ clones, Mut2.2). Finally, these two libraries were proportionally mixed to obtain the final library called Mut2, representing $2\times10^7$ different clones.

I.2.c. Quality Control of the Fc Libraries by Sequencing

The quality of the different libraries generated previously was assessed by PCR on cells to amplify the Fc gene (with the 5' primer 5'-CAGGAAACAGCTATGACC-3' (SEQ ID NO: 7) and the 3' primer 5'-TCACGTGCAAAAGCAGCGGC-3' (SEQ ID NO:8) and high throughput sequencing (with the 5' primer 5'-TGATTACGCCAAGCTTGC-3' (SEQ ID NO:9). The sequences of 96 clones randomly picked in each library (Mut1.1 to Mut1.4 and Mut2.1 to Mut2.2) were thereby determined. Finally, 35 clones of the pooled library Mut1 and 86 clones of the pooled library Mut2 were also sequenced to control the quality of the final library before the selection process.

The modifications of the mutated sequences were analysed using MilleGen proprietary software Mutanalyse4Fc adapted for the Fc molecule from the Mutanalyse 2.5 software described previously (Mondon et al., Biotechnol J. 2: 76-82 (2007)). This analysis confirmed that the mutations are randomly distributed along the entire gene, without any "hot spot"

Mut1 Analysis:

the frequency of mutations of Mut1 library is of 6.3 mutations per kilo bases (kb), which means 4.2 mutations per gene (666 nt). Amongst these mutations, 81.4% are substitutions, 16.8% are deletions and 1.8% additions, these last two categories introducing frame shifts in the gene. When considering only the sequences in frame, the mutation frequency is of 4.0 mutations per kb, i.e. 2.7 mutations per gene (1 to 6 mutated nucleotides per gene). The mutation analysis was also performed at the protein level to determine the active part of the library. Finally, the Mut1 library contains 28.6% of clones expressing the wild type fragment (non mutated or with silent mutations), 40.0% of clones containing a sequence out of frame or with a stop codon (not expressed) and 31.4% of clones with a mutated sequence (Fc variants). These last clones represent the active part of the library, comprising $3.5\times10^6$ different clones with on average 2.3 mutated amino acids per molecule.

Mut2 Analysis:

the frequency of mutations of Mut2 library is of 4.5 mutations per kilo bases (kb), which means 3.0 mutations per gene. Amongst these mutations, 96.3% are substitutions, 3.2% are deletions and 0.5% additions. When considering only the sequences in frame, the mutation frequency is of 4.3 mutations per kb, i.e. 2.9 mutations per gene (1 to 7 mutated nucleotides per gene). At the protein level, the Mut2 library contains 17.4% of clones expressing the wild type fragment (non mutated or with silent mutations), 9.3% of clones containing a sequence out of frame or with a stop codon (not expressed) and 73.3% of clones with a mutated sequence (Fc variants). These last clones represent the active part of the library, comprising $1.5\times10^7$ different clones with on average 1.9 mutated aa per molecule.

II. Phage Display Expression of the Fc Libraries and Selection of FcRn Improved Binders The Fc library was expressed at the surface of the bacteriophage M13 using standard procedures (Smith G P, Science 228: 1315 (1985)). E. coli XL1-Blue bacteria containing the Mut1 library (pMG58 vector) were grown in 60 ml of 2YT supplemented with 100 μg/ml ampicillin, 15 μg/ml tetracycline and 1% (w/v) glucose at 30° C., 230 rpm until $OD_{600nm}$=0.6 is reached. Cells were then infected with M13 helper phage (M13KO7, Biolabs, ratio bacteria/phage=1/3) at 37° C. for 20 min and phage-Fc production was continued overnight at 26° C., 230 rpm in 2YT/Ampicillin/Glucose with IPTG 0.5 mM and kanamycin 30 μg/ml. The following day, phages were precipitated with PEG6000 using standard protocols, resuspended in 1 ml phosphate buffer pH6 (sodium phosphate 100 mM, sodium chloride 50 mM pH6.0, called P6) and titrated by infecting XL1-Blue cells. Three selection strategies were applied using different conditions (FIG. 2) and 3 to 8 rounds of selection were performed per strategy (see below).

II.1. Selections on Solid Phase (Strategies 1 and 2) (See FIG. 2A):

For solid phase selections, $4\times10^{11}$ phages in P6/5% skimmed milk/0 1% Tween 20 were incubated on 8 wells of Maxisorp immunoplates previously coated with 0.5 μg neutravidin and 0.5 μg biotinylated FcRn (strategy 1) or 0.5 μg FcRn-p3 (strategy 2) and blocked with 5% skimmed milk in P6. After incubation for 2 hours at 37° C., wells were washed 20 times with P6/0.1% Tween 20 and eluted by incubation in 100 μl phosphate buffer pH7.4 (sodium phosphate 100 mM, sodium chloride 50 mM pH7.4)/well for 2 hours at 37° C. After titration, eluted phages were used to reinfect 10 ml of exponentially growing XL1-Blue bacteria and subsequently plated on solid 2YT medium/ampicillin/glucose. The following day, cells were scrapped in 2YT medium with 15% glycerol, frozen and kept at −80° C. until the next round of selection.

II.2. Selection in Liquid Phase (Strategy 3) (See FIG. 2B):

For liquid phase selection, $4\times10^{11}$ phages were first incubated with 250 nM or 100 nM biotinylated FcRn in 1 ml P6/5% skimmed milk/0.1% Tween 20 for 1 hour at room temperature under low agitation. Streptavidin coated magnetic beads (Dynal), previously blocked with 5% skimmed milk in P6 were then added to the phages for 30 minutes at room temperature. Phage-bead complexes were washed 15 times with P6/0.1% Tween 20 using a magnet (magnetic particle concentrator, Dynal). Phages were eluted by incubation in 500 μl phosphate buffer pH7.4 (sodium phosphate 100 mM, sodium chloride 50 mM, pH 7.4) for 2 hours at room temperature. Beads were discarded using the magnet and eluted phages in the supernatants were collected. After titration, eluted phages were used to reinfect 10 ml of exponentially growing XL1-Blue bacteria and subsequently plated on solid 2YT medium/ampicillin/glucose. The following day, cells were scrapped in 2YT medium with 15% glycerol, frozen and kept at −80° C. until the next round of selection.

II.3. Sequence Analysis:

During screening processes (MS1 and MS2), for each strategy, from round 3 to round 8, 48 to 96 clones were sequenced after PCR on cells (as described in I.2-c.). Sequence analysis was performed using MilleGen proprietary software AnalyseFc internally developed to rapidly analyse the selected Fc variants. Fc Variants were named according to the round of selection from which they were isolated (for Mut1 screening: B3A to B6A for strategy 1, S3A to S6A for strategy 2 and L3A/B to L6A-F for strategy 3, for Mut2 screening: C3A to C8A for strategy 1, T3A to T8A for strategy 2 and M3A/B for strategy 3). Numbers (1 to 96) refer to the localisation on the PCR plate for sequencing. Finally during the whole selection process, 227 different mutated clones were isolated for Mut1 and 223 different mutated clones for Mut2. All these clones were characterised using phage-ELISA assays.

II.4. Directed Mutagenesis

The sequence analysis of the improved Fc-variants isolated during MS1 showed that a large number of clones contained similar mutations (N434Y, N434S, P230S, P230T . . . ). Directed mutagenesis was performed to remove these mutations in order to reveal the effect of the associated mutations.

These new mutants were named based on the parental clone with an A or B added at the end of the name. 61 new mutants were tested. Some of these mutants are illustrated in table 1. The mutants considered as positive have a specific signal between 1.2 and 2.6-fold higher than that of Fc-WT in phage ELISA assay (see below). After MS2, several new mutants were constructed by directed mutagenesis by adding one or two mutations in the hinge region (P230S or P228L or P228R or P228L/P230S or P228R/P230S). These mutants were named based on the parental clone with a letter (A to G) added at the end of the name. 24 new mutants were tested and are illustrated in table 5.

II.5. Phage-ELISA Assays of the Selected Variants (FIG. 3)

The binding characteristics of the variants isolated during MS1 and MS2 displayed on the phage were determined using an ELISA test at pH6.0 with FcRn-p3 coated on wells (FIG. 3). Briefly, phage-Fc variants were produced as isolated clones on a 96-well plate in 800 µl cultures in 2YT/ampicillin/glucose infected with helper phage M13K07 (as described in paragraph 3). Phages produced overnight at 26° C. were recovered in the supernatants after 30 minutes centrifugation at 3000 g. These supernatants were directly diluted (1/2 and 1/4) in P6/5% skimmed milk/0.1% Tween 20 and tested on Maxisorp immunoplates previously coated with 0.25 µg FcRn-p3/well and blocked with 5% skimmed milk in P6. After incubation for 2 hours at 37° C., wells were washed 3 times with P6/0.1% Tween-20 and bound phages were detected with an HRP anti-M13 antibody (GE Healthcare).

Using this ELISA test, the 227 Fc variants selected during MS1 were tested in comparison with the wild type Fc (Fc-WT) and a positive control. This positive control (called Fc-H variant) is the double mutant T250Q/M428L and was described as having an improved affinity for FcRn (×28, Hinton P R et al., J. Biol. Chem. 279(8): 6213-6216 (2004)). This variant was generated by standard PCR protocols with two long oligonucleotides comprising the mutated codons and the restriction sites: 5' primer (SEQ ID NO: 10)

5'-CGGGATCCTGCCCACCGTGCCCAGCACCTGAACTCCTGGGGGGACCG

TCAGTCTTCCTCTTCCCCCCAAAACCCAAGGACCAACTCATGATCTCCCG

GAC-3' and 3' primer (SEQ ID NO: 11)

5'-GCGAATTCTTTACCCGGAGACAGGGAGAGGCTCTTCTGCGTGTAGTG

GTTGTGCAGAGCCTCATGCAGCACGGAGCATGAGAAG-3'

(BamHI and EcoRI restriction sites are underlined and the characters in grey correspond to the mutated codons). In the phage-ELISA assay, the Fc-H variant had a specific signal on average 3.2-fold stronger than the wild type Fc, i.e. Fc-WT (ratio variant/Fc-WT) and amongst the 227 Fc-variants tested, 73 variants had a ratio/Fc-WT>3.2, which means that they had a better binding to FcRn than the Fc-H variant (table 2). Positive variants from MS1 and having a single point amino acid modification have a specific signal from about 1.2-fold to 3.5-fold stronger than the wild-type Fc (see table 1).

TABLE 1

Variants having a single amino acid modification identified during MS1 or obtained by directed mutagenesis

| Variant name | Mutation | ratio/Fc-WT |
|---|---|---|
| B4A_13 | P228L | 3.5 |
| B3A_32 | P228R | 3.1 |
| B5A_35 | P230S | 2.8 |
| L3A_20 | V303A | 2.8 |
| L5D_47 | P230Q | 2.7 |
| S3A_05 | N434S | 2.7 |
| B4A_22A | A378V | 2.6 |
| B5A_05 | H433R | 2.3 |
| S3A_04 | P230T | 2.3 |
| B4A_08 | V397M | 2.2 |
| B5A_25B | N315D | 2.1 |
| B5A_15 | M428L | 2.0 |
| L3B_21A | V302A | 1.9 |
| S3A_25A | V264E | 1.9 |
| L3A_01 | T256N | 1.8 |
| S3A_08 | P387S | 1.8 |
| L3A_35 | S440N | 1.7 |
| L3B_20 | E382G | 1.7 |
| B3A_08 | C226G | 1.6 |
| B5A_17A | Q362E | 1.6 |
| B5A_43 | R416G | 1.6 |
| L5A_01 | N389K | 1.5 |
| S3A_09A | S426T | 1.4 |
| S3A_21 | N297D | 1.4 |
| B3A_17 | T307A | 1.3 |
| B5A_31A | Q342R | 1.2 |
| L3A_10 | L309P | 1.2 |
| L3A_16 | A378T | 1.2 |
| L3A_25 | V264A | 1.2 |
| L3B_19 | Q386R | 1.2 |
| B4A_12 | K414R | 1.1 |
| B4A_29 | K447E | 1.1 |
| L4F_02 | A330T | 1.1 |
| L5D_01 | V305A | 1.1 |
| L6A_39 | N389T | 1.1 |
| S5A_18A | F404L | 1.1 |
| L5D_29A | Q342K | 1.1 |
| B4A_44A | K290R | 1.1 |
| L6C_10B | D265G | 1.1 |
| L4A_39 | D401G | 1.0 |
| B6A_34A | N390S | 1.0 |
| L6C_44A | T359A | 1.0 |
| B5A_04A | N384I | 1.0 |
| S3A_24A | E269D | 1.0 |
| L5D_09A | T289I | 1.0 |
| S3A_01 | Q311R | 0.9 |
| S3A_42 | K360R | 0.9 |
| L4F_14 | G371D | 0.9 |
| L5B_35 | N276S | 0.9 |
| L6A_29 | S267N | 0.9 |
| B3A_02A | N421S | 0.9 |
| S4A_17B | Q362R | 0.9 |
| S3A_26A | T394A | 0.9 |
| B5A_14A | Q347R | 0.9 |
| L6B_22 | P395S | 0.8 |
| B5A_28A | K360N | 0.8 |
| L5D_41A | K322R | 0.8 |
| L5A_31 | N361S | 0.5 |

TABLE 2 variants selected during MS1

| Variant name | Mutations | Ratio/Fc-WT |
|---|---|---|
| S5A_41 | P230T/V303A/K322R/N389T/F404L/N434S | 9.0 |
| B5A_01 | P228R/N434S | 8.2 |
| S5A_26 | Q311R/K334R/Q342E/N434Y | 7.9 |
| B4A_21 | C226G/Q386R/N434Y | 6.9 |
| S4A_07 | T307P/N389T/N434Y | 6.6 |
| B5A_48 | P230S/N434S | 6.5 |

TABLE 2-continued

| variants selected during MS1 | | |
|---|---|---|
| Variant name | Mutations | Ratio/Fc-WT |
| L6B_31 | P230T/V305A/T307A/A378V/L398P/N434S | 6.3 |
| S4A_01 | P230T/P387S/N434S | 6.2 |
| S3A_24 | P230Q/E269D/N434S | 6.1 |
| S4A_14 | N276S/A378V/N434S | 5.9 |
| S4A_12 | R355Q/T393N/S426T/N434Y | 5.8 |
| S5A_47 | P230T/N434S | 5.8 |
| S5A_43 | P230S/V284L/A378V | 5.7 |
| B5A_16 | S239A/S298G/N315D/Q347R/N434Y/S440R | 5.6 |
| B5A_23 | Q362E/N434Y | 5.4 |
| S4A_24 | V264E/R301C/A378V/E382G | 5.4 |
| L4A_28 | M428L/N434S/Q438R/P445S | 5.2 |
| S4A_03 | A378V/N434S | 5.2 |
| S4A_29 | P230Q/F241L/V264E | 5.2 |
| S5A_07 | A378V/N421T/N434S | 5.1 |
| B6A_31 | S375G/M428L/H433P | 5.0 |
| L5D_09 | P230Q/T289I/N434S | 4.8 |
| S4A_06 | K288R/T307P/N421S/N434S | 4.7 |
| B5A_17 | N315D/Q362R/N434Y | 4.6 |
| S4A_02 | A378V/N434Y | 4.6 |
| S4A_36 | P230Q/V264A/P352S/A378V | 4.5 |
| S4A_44 | P227S/N434Y | 4.5 |
| L5B_14 | C226G/N434S | 4.4 |
| L6B_41 | P230S/M428L | 4.4 |
| S6A_48 | R355Q/K392E/T393N/S426T/N434Y | 4.4 |
| B6A_41 | N434Y/Q438R/K447E | 4.3 |
| L5D_18 | V397M/N434S | 4.3 |
| S3A_25 | V264E/N434S | 4.3 |
| S5A_20 | P230Q/F2 41Y/K246R/D270E | 4.3 |
| S4A_25 | D265G/S408T/N434Y/S444F | 4.2 |
| S4A_42 | V264A/N434Y/G446A | 4.2 |
| B5A_18 | V412A/M428L/H433R/N434S/K447E | 4.1 |
| B4A_39 | E382G/N434S | 4.0 |
| L4A_45 | P228L/N297D | 4.0 |
| L6A_11 | M428L/H433R | 4.0 |
| S4A_30 | V303A/N434S | 4.0 |
| B4A_01 | E345Q/A378S/E380Q/N434Y | 3.9 |
| B4A_22 | S383R/V397M/N434S | 3.9 |
| S4A_17 | V302A/N389T/N434S | 3.8 |
| B4A_03 | R292W/T307P/A330V/N434S | 3.7 |
| B5A_04 | N384I/N434Y | 3.7 |
| B6A_20 | K320T/N434Y/K439R/K447E | 3.7 |
| S4A_05 | A378V/D401A/N434Y | 3.7 |
| S4A_11 | N389T/N434Y | 3.7 |
| S6A_24 | A231T/V397M/N434S | 3.7 |
| B4A_46 | G371D/N434Y | 3.6 |
| B5A_25 | F243L/N315D/T411A/N434S | 3.6 |
| S3A_06 | P230T/A231T/A378V | 3.6 |
| B3A_02 | N421S/N434Y | 3.5 |
| B4A_13 | P228L | 3.5 |
| S3A_07 | V264E/A378V/E382G | 3.5 |
| S4A_27 | M252L/N434S | 3.5 |
| B3A_15 | L309P/N434S | 3.4 |
| B3A_34 | N434Y/S440N | 3.4 |
| B6A_34 | N315D/A330V/N434S | 3.4 |
| S3A_09 | S426T/N434S/K439R | 3.4 |
| S5A_46 | Q386R/N434Y | 3.4 |
| B4A_44 | P230S/K29OR | 3.3 |
| B6A_36 | F241L/V305A/D356N/N434Y | 3.3 |
| L5D_29 | Q342K/N434Y | 3.3 |
| S5A_05 | N434Y/S440R | 3.3 |
| S5A_19 | F243L/N434Y | 3.3 |
| S5A_27 | A327V/A378V/N389T/N434Y | 3.3 |
| B5A_28 | K360N/N434Y | 3.2 |
| L3A_39 | S375G/P395S/N434S | 3.2 |
| L4A_15 | P395S/N434H | 3.2 |
| L4F_16 | N434Y/K447N | 3.2 |
| S5A_40 | T299M/N434Y | 3.2 |

The 223 variants selected during MS2 were tested using the same ELISA protocol but in comparison with the Fc-H variant and the best Fc variant isolated during MS1 (S5A_41), because the difference between the Fc-WT signal and the signal of the Fc variants was too great to be compared on the same ELISA plate. Amongst the 223 Fc variants tested, 209 Fc variants were better than the Fc-H (ratio/Fc-H>1.1) and 39 Fc variant were better than the best Fc variant isolated during MS1. To compare the variants with the Fc-WT, an estimated ratio/Fc-WT was calculated by multiplying the ratio/Fc-H of the variants by the ratio/Fc-WT of the Fc-H (=3.2) determined during MS1 (ratio/Fc-WT=3.2×ratio/Fc-H) (table 3)

TABLE 3

| variants of MS2 | | | |
|---|---|---|---|
| Variant name | Mutations | Ratio/ Fc-H | Ratio/ FWT |
| C6A_69 | T307A/N315D/A330V/E382V/N389T/N434Y | 8.9 | 28.4 |
| C6A_78 | T256N/A378V/S383N/N434Y | 8.7 | 27.8 |
| T5A_74 | N315D/A330V/N361D/A378V/N434Y | 8.6 | 27.6 |
| C6A_74 | V259I/N315D/N434Y | 8.5 | 27.2 |
| C6A_60 | P230S/N315D/M428L/N434Y | 8.4 | 26.8 |
| T5A_58 | F241L/V264E/T307P/A378V/H433R | 8.1 | 26.1 |
| C6A_72 | T250A/N389K/N434Y | 8.0 | 25.7 |
| T5A_93 | V305A/N315D/A330V/P395A/N434Y | 8.0 | 25.7 |
| T5A_78 | V264E/Q386R/P396L/N434S/K439R | 8.0 | 25.6 |
| T5A_87 | N315D/A330V/Q362R/N434Y | 7.8 | 25.0 |
| C6A_66 | E294del/T307P/N434Y | 7.7 | 24.6 |
| C6A_85 | V305A/N315D/A330V/N389K/N434Y | 7.4 | 23.8 |
| C8A_15 | N315D/A327V/A330V/V397M/N434Y | 7.4 | 23.7 |
| T5A_89 | P230T/F241L/V264E/D265G/A378V/N421T | 7.1 | 22.8 |
| T7A_92 | V264E/P396L/S415N/N434S | 6.7 | 21.4 |
| T6A_57 | P227L/V264E/A378V/N434S | 6, 4 fhr 6.4 | 20.3 |
| T5A_94 | V264E/A378T/P396L | 5.8 | 18.5 |
| T6A_75 | P230T/N315D/Q362R/S426T/N434Y | 5.7 | 18.3 |
| C3A_13 | C226G/N315D/A330V/N434Y | 5.6 | 17.9 |
| T5A_55 | P230L/F241L/F243L/V264E/T307P/A378V | 5.6 | 17.9 |
| T6A_85 | T250A/N315D/N325S/A330V/N434Y | 5.1 | 16.3 |
| C5A_39 | K290E/N315D/Q342R/E382V/N434Y | 5.0 | 15.9 |
| T5A_57 | F241L/N315D/A330V/K392R/N434Y | 4.9 | 15.8 |
| C5A_09 | F241L/V264E/T307P/A378V/N434S | 4.8 | 15.2 |
| T6A_22 | P230T/V264E/S403T/N434S | 4.7 | 15.2 |
| T5A_81 | V264E/A378V/R416K | 4.6 | 14.9 |
| C6A_12 | P230T/N315D/Q362E/N434Y | 4.6 | 14.9 |
| C4A_14 | C226G/N315D/N434Y | 4.6 | 14.8 |
| T4A_42 | C226G/N315D/Q362R/N434Y | 4.6 | 14.7 |
| T5A_25 | C226G/V264E/Q347R/K370R/A378V/N434S | 4.6 | 14.7 |
| T4A_48 | V308I/N315D/A330V/E382V/N434Y | 4.5 | 14.5 |
| C6A_48 | P230T/V264E/A378V/N434S | 4.5 | 14.4 |
| T5A_45 | A231T/F241L/V264E/A378T/V397M/N434S | 4.5 | 14.3 |
| T6A_23 | P230L/V264E/A378V/N434S | 4.4 | 14.1 |
| C5A_65 | P230T/N315D/A330V/Q386K/N434Y | 4.2 | 13.5 |
| C6A_88 | C226G/N315D/A330V/N389T/N434Y | 4.2 | 13.4 |
| C4A_13 | S267R/T307P/A378V/N421T/N434Y | 4.1 | 13.2 |
| C3A_35 | P230S/N315D/P387T/N434Y | 4.0 | 12.9 |
| T4A_37 | P230S/V264E/P352S/A378V/N434S | 4.0 | 12.8 |
| C5A_18 | P230T/N315D/Q362R/N434Y | 3.9 | 12.3 |
| T3A_22 | F241L/V264E/A378V/N434S | 3.8 | 12.2 |
| C5A_12 | N315D/Q362E/N389K/N434Y | 3.8 | 12.1 |
| C4A_29 | T307P/N315D/N361S/Q362R/N434Y | 3.8 | 12.0 |
| T4A_44 | C226G/V264E/A378V/F404L | 3.8 | 12.0 |
| C3A_42 | N315D/A330V/N389K/V397M/N434Y | 3.7 | 12.0 |
| C7A_82 | P230T/K246R/N389T/P395S/N434Y | 3.7 | 11.9 |
| T4A_31 | P230T/F241L/V264E/T307P/A378V | 3.7 | 11.7 |
| T7A_48 | P230T/L234R/N315D/A330V/N434Y | 3.6 | 11.6 |
| T7A_49 | P230T/N315D/K320E/Q362R/N434Y | 3.6 | 11.6 |
| C7A_43 | V264E/T307P/A378V/P396S/N434S | 3.6 | 11.5 |
| T4A_26 | V264E/T307P/A378V/E382G/Q386R | 3.6 | 11.5 |
| T4A_19 | T307P/A378V/N434S | 3.6 | 11.4 |
| C4A_06 | P230T/N315D/A330V/N434Y | 3.6 | 11.4 |
| T4A_46 | P230T/N389K/N434Y | 3.6 | 11.4 |
| T8A_24 | V264E/T307P/A378V/N434S | 3.5 | 11.1 |
| C6A_36 | T307P/N315D/E382G/Q419H/N434Y | 3.4 | 10.9 |
| C7A_68 | V264E/N315D/A378V/N390S/G420R/N434Y | 3.4 | 10.9 |
| C5A_15 | V303A/N315D/A330V/E382V/N434Y | 3.4 | 10.9 |
| T5A_40 | P230T/V264E/T307P/A378V/N421T | 3.4 | 10.8 |
| C4A_28 | V264E/A378V/N434Y | 3.4 | 10.8 |
| C4A_41 | N315D/A330V/Q362E/N434Y | 3.4 | 10.8 |
| T6A_42 | C226G/N434Y | 3.4 | 10.7 |
| T4A_33 | P230T/V264E/A378V/N389T/D399N/H433R | 3.3 | 10.7 |
| T5A_24 | V264E/A378V/N434S | 3.3 | 10.7 |
| T8A_87 | F241L/V264E/A378V/N421T/N434S/L443R | 3.3 | 10.7 |

TABLE 3-continued

| variants of MS2 | | | |
|---|---|---|---|
| Variant name | Mutations | Ratio/ Fc-H | Ratio/ FWT |
| T6A_39 | C226Y/A378V/N421T/N434S | 3.3 | 10.4 |
| C3A_45 | F243L/N315D/A330V/N389K/N434Y | 3.3 | 10.4 |
| C3A_09 | S298G/N434Y | 3.2 | 10.4 |
| T6A_21 | N315D/A378V/N434Y | 3.1 | 10.0 |
| C6A_13 | T307P/A378V/N434Y | 3.1 | 10.0 |
| C3A_27 | N315D/S354P/S383N/N434Y | 3.1 | 10.0 |
| T6A_16 | P230T/V264E/N315D/K370R/A378V | 3.1 | 9.9 |
| C3A_21 | N315D/A330V/S400P/N434Y | 3.0 | 9.8 |
| C3A_08 | V264E/P352S/A378V/N434S | 3.0 | 9.7 |
| T4A_18 | N315D/Q342R/E382V/N434Y | 3.0 | 9.7 |
| T4A_04 | N315D/A330V/E382V/N434Y | 3.0 | 9.7 |
| T7A_58 | N315D/Q362E/N434Y | 2.9 | 9.4 |
| C6A_04 | Q342R/E382V/N434Y | 2.9 | 9.4 |
| C5A_19 | V264A/V305A/N315D/A330V/N434Y | 2.9 | 9.3 |
| T6A_13 | P230T/N315D/A330V/Q362R/N434Y | 2.9 | 9.3 |
| T7A_87 | P230S/N315D/Q362R/N434Y | 2.9 | 9.3 |
| C3A_24 | T307P/N389T/D401G/N421T/N434Y | 2.9 | 9.2 |
| C4A_22 | P230T/N434Y | 2.9 | 9.1 |
| T6A_47 | P230T/K320T/N434Y | 2.8 | 9.1 |
| C5A_58 | V264E/A378V/P396L/N434S | 2.8 | 9.1 |
| T6A_40 | P230A/F241L/V264E/A378V/N421T | 2.8 | 9.1 |
| T5A_51 | V264E/A378V/F404L/N434S | 2.8 | 9.0 |
| C4A_25 | N315D/A330V/V397M/N434Y | 2.8 | 8.9 |
| T3A_15 | V264E/A378V/T394A/F404L/N434S | 2.8 | 8.9 |
| C7A_18 | V264E/A378V/K414R/N421T/N434Y | 2.8 | 8.9 |
| T7A_18 | V264E/A378V/Q386R/N434S | 2.8 | 8.9 |
| C4A_36 | N315D/K320T/N434Y | 2.8 | 8.9 |
| C5A_75 | T307N/N315D/N434Y | 2.8 | 8.9 |
| C5A_28 | T307P/N434Y | 2.8 | 8.8 |
| T5A_05 | V264E/E269G/A378V/N421T/N434S | 2.7 | 8.8 |
| C8A_41 | N315D/E382V/H433P/N434Y | 2.7 | 8.8 |
| C5A_44 | N315D/N389K/N434Y | 2.7 | 8.7 |
| C5A_03 | V264A/N315D/N434Y | 2.7 | 8.7 |
| T4A_45 | V264E/L309P/P396L/N434S | 2.7 | 8.7 |
| C4A_27 | V264A/T299A/A378V/E382G/N434Y | 2.7 | 8.7 |
| T6A_12 | V264E/A378V/N421T/N434S | 2.7 | 8.6 |
| T7A_76 | V264E/K370R/A378V/P396L/H439R | 2.7 | 8.5 |
| T5A_08 | V264E/P291Q/A378V/N434S | 2.6 | 8.5 |
| M3A_21 | F241L/V264E/T307P/A378V/N421T | 2.6 | 8.4 |
| C5A_20 | N315D/S415D/N434Y | 2.6 | 8.4 |
| T6A_09 | P230T/T307A/N315D/A327V/N434Y | 2.6 | 8.3 |
| C7A_27 | V264E/T307N/A378V/V397M/N434Y | 2.6 | 8.2 |
| T7A_46 | V264E/A378V/G385R/N434S | 2.6 | 8.2 |
| T8A_81 | V264A/N315D/E382V/N434Y | 2.5 | 8.2 |
| T7A_57 | P230T/T307A/N315D/A330V/Q418E/N434Y | 2.5 | 8.1 |
| C3A_43 | N315D/R416G/N434Y | 2.5 | 8.1 |
| C4A_18 | N315D/A330V/A378V/N434Y | 2.5 | 8.1 |
| T4A_41 | F241R/V264E/T307P/A378V | 2.5 | 8.0 |
| C3A_01 | N315D/A330V/N434Y | 2.5 | 8.0 |
| T8A_41 | V264E/P343S/A378V/N434S | 2.5 | 7.9 |
| T5A_28 | F241L/V264E/A378V/N434Y | 2.5 | 7.9 |
| T3A_10 | N315D/A330V/N389K/N434Y | 2.4 | 7.8 |
| T3A_01 | V264E/T307P/A378V/N421T | 2.4 | 7.8 |
| T5A_59 | Q342R/R355G/E382V/N434Y | 2.4 | 7.8 |
| M3B_09 | V264A/N315D/A330V/N389K/N434Y | 2.4 | 7.7 |
| C8A_14 | V305A/Q386R/N434Y | 2.4 | 7.6 |
| C4A_01 | N315D/Q362R/N389K/N434Y | 2.4 | 7.5 |
| C4A_24 | L309P/N315D/A330V/N434Y | 2.3 | 7.5 |
| C7A_13 | F241L/V264E/A378V/N421T/N434Y | 2.3 | 7.4 |
| T4A_32 | V264E/A378V/H433R | 2.3 | 7.4 |
| T3A_16 | F241L/V264E/T307P/A378V | 2.3 | 7.4 |
| C7A_89 | T307P/A327T/N389T/N421T/N434Y | 2.3 | 7.4 |
| C5A_50 | D270N/N315D/N434Y | 2.3 | 7.3 |
| T3A_41 | V264E/T307P/A378V | 2.3 | 7.2 |
| C4A_45 | K246R/H285Y/N315D/A330V/N434Y | 2.3 | 7.2 |
| T7A_24 | V264E/A378V/N421T/N434Y | 2.3 | 7.2 |
| T4A_28 | P230T/A378V | 2.2 | 7.0 |
| T5A_37 | S298G/N315D/A330V/N434Y | 2.2 | 7.0 |
| C3A_31 | N315D/A330V/N389K/D401G/N434Y | 2.2 | 6.9 |
| C4A_15 | E233D/N315D/N434Y | 2.2 | 6.9 |
| C7A_02 | V264E/K370R/A378V/N434Y | 2.2 | 6.9 |
| C7A_37 | F241L/N315D/N389K/N434Y | 2.2 | 6.9 |
| C7A_69 | V264E/H285Y/A378V/N434Y | 2.1 | 6.9 |
| C7A_52 | D265G/A378V/N434Y | 2.1 | 6.8 |
| T5A_64 | P230T/V264A/N325S/V397M/N434S | 2.1 | 6.7 |

TABLE 3-continued

| variants of MS2 | | | |
|---|---|---|---|
| Variant name | Mutations | Ratio/ Fc-H | Ratio/ FWT |
| C7A_23 | S298N/A378V/N434Y | 2.1 | 6.6 |
| C7A_67 | N315D/A330V/N389R/N434Y | 2.1 | 6.6 |
| T5A_03 | V264E/P396L/N434S | 2.0 | 6.4 |
| C8A_08 | V264A/N315D/A330V/N434Y | 2.0 | 6.4 |
| C3A_03 | N315D/N434Y | 2.0 | 6.4 |
| T3A_47 | T307P/A378T/V397M | 2.0 | 6.3 |
| C5A_63 | S298N/N315D/A330V/N434Y | 2.0 | 6.3 |
| T7A_17 | V264E/P291S/Q362R/A378V/N434Y | 2.0 | 6.3 |
| T4A_43 | 1332V/K370R/A378V/N434S | 2.0 | 6.3 |
| M3A_18 | T307P/A378V/N421T | 1.9 | 6.2 |
| C6A_05 | T307A/N315D/A330V/N434Y | 1.9 | 6.2 |
| C3A_15 | V264E/T307A/A378V | 1.9 | 6.0 |
| T5A_29 | N315D/E382V/N434Y | 1.9 | 6.0 |
| T5A_52 | N315D/A327V/A330V/N434Y | 1.9 | 5.9 |
| T8A_45 | S375A/A378V/N434Y | 1.8 | 5.9 |
| C6A_21 | N315D/A330V/K360R/N389K/N434Y | 1.8 | 5.8 |
| T7A_05 | V264E/T359A/N434Y | 1.8 | 5.8 |
| T8A_50 | V264E/P396L/N434Y | 1.8 | 5.8 |
| T7A_94 | S267N/P352S/A378V/P396L/N434S | 1.8 | 5.8 |
| C6A_35 | T250A/N315D/A330V/N434Y | 1.8 | 5.7 |
| C7A_22 | N315D/K334E/A378V/N434Y | 1.8 | 5.7 |
| M3A_06 | F241L/V264E/A378T/V397M | 1.8 | 5.7 |
| T7A_13 | C226Y/N315D/N434Y | 1.8 | 5.7 |
| T5A_90 | N315D/A330V/K392R/S424L/N434Y | 1.8 | 5.7 |
| C3A_39 | A231V/Q342E/N434Y | 1.8 | 5.6 |
| T3A_13 | N315D/V369A/N434Y | 1.8 | 5.6 |
| T8A_34 | T307A/N315D/T335A/N434Y | 1.8 | 5.6 |
| M3A_26 | V264E/T307P/K340E/Q342R/A378V | 1.8 | 5.6 |
| C3A_23 | N389K/N434Y | 1.8 | 5.6 |
| M3A_08 | V264E/T307P/A378T/V397M | 1.7 | 5.6 |
| C8A_61 | P230T/V264E/P396L/N434Y | 1.7 | 5.5 |
| M3B_04 | F241L/V264E/Q342R/A378V | 1.7 | 5.5 |
| C4A_32 | V264E/N315D/A378V | 1.7 | 5.4 |
| T7A_35 | N315D/Q362R/N434Y/S444P | 1.7 | 5.4 |
| C7A_49 | N315D/A330V/T394A/N434Y | 1.7 | 5.3 |
| C7A_28 | N315D/S383N/N434Y | 1.6 | 5.3 |
| T6A_58 | F241L/V264E/T307P/K338R/A378V/N434S | 1.6 | 5.2 |
| C6A_33 | S426T/N434Y | 1.6 | 5.2 |
| C6A_93 | V264M/D265N/N315D/A330V/N434Y | 1.6 | 5.0 |
| M3A_22 | P230S/A378V/K439R | 1.5 | 5.0 |
| T3A_37 | F241L/V264E/A378V | 1.5 | 4.9 |
| T7A_95 | N315D/Q342R/N384T/N434Y | 1.5 | 4.9 |
| C3A_18 | F241L/V264E/A378V/N421T | 1.5 | 4.8 |
| T3A_28 | T307P/A378V/Q418R | 1.5 | 4.8 |
| T3A_06 | T307P/A378V | 1.5 | 4.8 |
| C6A_23 | V264E/N434Y | 1.5 | 4.7 |
| T3A_21 | N315D/K317R/N434Y | 1.5 | 4.7 |
| T3A_34 | V264E/P352S/A378V | 1.4 | 4.6 |
| C5A_48 | T350A/N434Y | 1.4 | 4.6 |
| T3A_43 | V264E/E345G/A378V | 1.4 | 4.5 |
| M3A_01 | N361D/N434Y | 1.4 | 4.4 |
| T4A_39 | V264E/A378V/P396L | 1.4 | 4.4 |
| C5A_41 | N315D/A327T/A330V/Q362R/N434Y | 1.3 | 4.3 |
| M3A_34 | S267N/T307N/K370R/A378V | 1.3 | 4.3 |
| T4A_34 | V264E/A378V/Q418K | 1.3 | 4.3 |
| C3A_07 | T307P/A330T/A378V | 1.3 | 4.2 |
| T3A_11 | P291S/N315D/A327V/A330V/N434Y | 1.3 | 4.0 |
| C6A_02 | T307N/N315D/A330V/N434Y | 1.2 | 3.9 |
| T3A_09 | V264E/A378V/N421T | 1.2 | 3.9 |
| T5A_44 | F241L/V264E/T307P/A378T/V397M | 1.2 | 3.8 |
| T3A_12 | T256N/A378V | 1.2 | 3.8 |
| M3B_23 | F241L/V264E/T307P | 1.2 | 3.8 |
| M3A_35 | V264E/N315D/P396L | 1.1 | 3.7 |
| T3A_26 | V397A/N434Y | 1.1 | 3.6 |
| T3A_08 | V264E/A378V/F404L | 1.1 | 3.5 |
| T6A_93 | T299K/Q311R/N315D/N434Y | 1.1 | 3.5 |
| M3A_12 | N315D/Q362R/N421D/N434S | 1.1 | 3.4 |
| T3A_20 | V303I/N434Y | 1.1 | 3.4 |
| T3A_30 | V264E/A378V/V422A | 1.1 | 3.4 |

Overall, 282 Fc variants having better binding for FcRn than Fc-H were isolated during MS1 and MS2 processes.

Analysis of the sequences of these 282 Fc variants revealed that they include mutations all over the molecule on 115 different positions (table 4).

TABLE 4 mutations of MS1 and MS2 variants

| Position | Percentage of variants | Modification |
|---|---|---|
| C226 | 3.9 | G or Y |
| P227 | 0.7 | S or L |
| P228 | 1.1 | R or L |
| P230 | 16.3 | S, T, L, A or Q |
| A231 | 1.4 | T or V |
| E233 | 0.4 | D |
| L234 | 0.4 | R |
| S239 | 0.4 | A |
| F241 | 9.2 | L, Y or R |
| F243 | 1.4 | L |
| K246 | 1.1 | R |
| T250 | 1.1 | A |
| M252 | 0.4 | L |
| T256 | 0.7 | N |
| V259 | 0.4 | I |
| V264 | 33.0 | A, E or M |
| D265 | 1.4 | G or N |
| S267 | 1.1 | N or R |
| E269 | 0.7 | D or G |
| D270 | 0.7 | N or E |
| N276 | 0.4 | S |
| V284 | 0.4 | L |
| H285 | 0.7 | Y |
| K288 | 0.4 | R |
| T289 | 0.4 | I |
| K290 | 0.7 | R or E |
| P291 | 1.1 | S or Q |
| R292 | 0.4 | W |
| E294 | 0.4 | deletion |
| N297 | 0.4 | D |
| S298 | 1.8 | G or N |
| T299 | 1.1 | M, A or K |
| R301 | 0.4 | C |
| V302 | 0.4 | A |
| V303 | 1.4 | A or I |
| V305 | 2.1 | A |
| T307 | 16.3 | P, A or N |
| V308 | 0.4 | I |
| L309 | 1.1 | P |
| Q311 | 0.7 | R |
| N315 | 34.0 | D |
| K317 | 0.4 | R |
| K320 | 1.4 | T or E |
| K322 | 0.4 | R |
| N325 | 0.7 | S |
| A327 | 2.5 | V or T |
| A330 | 17.0 | V or T |
| I332 | 0.4 | V |
| K334 | 0.7 | E or R |
| T335 | 0.4 | A |
| K338 | 0.4 | R |
| K340 | 0.4 | E |
| Q342 | 3.6 | R, E or K |
| P343 | 0.4 | S |
| E345 | 0.7 | Q or G |
| Q347 | 0.7 | R |
| T350 | 0.4 | A |
| P352 | 1.8 | S |
| S354 | 0.4 | P |
| R355 | 1.1 | Q or G |
| D356 | 0.4 | N |
| T359 | 0.4 | A |
| K360 | 0.7 | N or R |
| N361 | 1.1 | D or S |
| Q362 | 6.7 | R or E |
| V369 | 0.4 | A |
| K370 | 2.1 | R |
| G371 | 0.4 | D |
| S375 | 1.1 | A or G |
| A378 | 37.2 | V, T or S |
| E380 | 0.4 | Q |

TABLE 4-continued mutations of MS1 and MS2 variants

| Position | Percentage of variants | Modification |
|---|---|---|
| E382 | 6.0 | V or G |
| S383 | 1.4 | R or N |
| N384 | 0.7 | I or T |
| G385 | 0.4 | R |
| Q386 | 2.5 | R or K |
| P387 | 0.7 | S or T |
| N389 | 9.2 | T, K or R |
| N390 | 0.4 | S |
| K392 | 1.1 | E or R |
| T393 | 0.7 | N |
| T394 | 0.7 | A |
| P395 | 1.4 | A or S |
| P396 | 4.6 | S or L |
| V397 | 5.0 | A or M |
| L398 | 0.4 | P |
| D399 | 0.4 | N |
| S400 | 0.4 | P |
| D401 | 1.1 | A or G |
| S403 | 0.4 | T |
| F404 | 1.8 | L |
| S408 | 0.4 | T |
| T411 | 0.4 | A |
| V412 | 0.4 | A |
| K414 | 0.4 | R |
| S415 | 0.7 | D or N |
| R416 | 0.7 | K or G |
| Q418 | 1.1 | R, K or E |
| Q419 | 0.4 | H |
| G420 | 0.4 | R |
| N421 | 7.8 | T, S or D |
| V422 | 0.4 | A |
| S424 | 0.4 | L |
| S426 | 1.8 | T |
| M428 | 2.1 | L |
| H433 | 2.8 | R or P |
| N434 | 79.1 | Y, S or H |
| Q438 | 0.7 | R |
| K439 | 1.4 | R |
| S440 | 1.1 | R or N |
| L443 | 0.4 | R |
| S444 | 0.7 | F or P |
| P445 | 0.4 | S |
| G446 | 0.4 | A |
| K447 | 1.4 | E or N |

Moreover, 16 positions are preferentially mutated and are considered as key positions: C226, P230, F241, V264, T307, N315, A330, Q342, Q362, A378, E382, N389, P396, V397, N421 and N434. Particularly, 4 positions are more preferably mutated and are considered as most preferred key positions: V264, N315, A378 and N434 (FIG. 4).

Fc variants of MS2 having better binding for FcRn compared to the best variant of MS1 (S5A_41), are showed in Table 5.

TABLE 5 best variants of MS2

| Variant name | Mutations | Ratio/ Fc-H | Standard deviation | Ratio/ Fc-WT |
|---|---|---|---|---|
| C6A_69 | T307A/N315D/A330V/E382V/N389T/N434Y | 8.9 | 1.7 | 28.4 |
| C6A_78 | T256N/A378V/S383N/N434Y | 8.7 | 1.9 | 27.8 |
| T5A_74 | N315D/A330V/N361D/A378V/N434Y | 8.6 | 1.6 | 27.6 |
| C6A_74 | V259I/N315D/N434Y | 8.5 | 1.5 | 27.2 |
| C6A_60 | P230S/N315D/M428L/N434Y | 8.4 | 1.8 | 26.8 |
| T5A_58 | F241L/V264E/T307P/A378V/H433R | 8.1 | 1.5 | 26.1 |
| C6A_72 | T250A/N389K/N434Y | 8.0 | 1.1 | 25.7 |
| T5A_93 | V305A/N315D/A330V/P395A/N434Y | 8.0 | 1.6 | 25.7 |

TABLE 5-continued

| best variants of MS2 | | | | |
|---|---|---|---|---|
| Variant name | Mutations | Ratio/ Fc-H | Standard deviation | Ratio/ Fc-WT |
| T5A_78 | V264E/Q386R/P396L/N434S/K439R | 8.0 | 1.5 | 25.6 |
| T5A_87 | N315D/A330V/Q362R/N434Y | 7.8 | 1.4 | 25.0 |
| C6A_66 | E294del/T307P/N434Y | 7.7 | 0.9 | 24.6 |
| C6A_85 | V305A/N315D/A330V/N389K/N434Y | 7.4 | 1.5 | 23.8 |
| C8A_15 | N315D/A327V/A330V/V397M/ N434Y | 7.4 | 1.8 | 23.7 |
| T5A_89 | P230T/F241L/V264E/D265G/A378V/ N421T | 7.1 | 1.2 | 22.8 |
| T7A_92 | V264E/P396L/S415N/N434S | 6.7 | 1.5 | 21.4 |
| T6A_57 | P227L/V264E/A378V/N434S | 6.4 | 1.7 | 20.3 |
| T5A_94 | V264E/A378T/P396L | 5.8 | 1.0 | 18.5 |
| T6A_75 | P230T/N315D/Q362R/S426T/N434Y | 5.7 | 1.3 | 18.3 |
| C3A_13 | C226G/N315D/A330V/N434Y | 5.6 | 0.9 | 17.9 |
| T5A_55 | P230L/F241L/F243L/V264E/T307P/ A378V | 5.6 | 1.2 | 17.9 |
| T6A_85 | T250A/N315D/N325S/A330V/N434Y | 5.1 | 1.7 | 16.3 |
| C5A_39 | K290E/N315D/Q342R/E382V/N434Y | 5.0 | 0.6 | 15.9 |
| T5A_57 | F241L/N315D/A330V/K392R/N434Y | 4.9 | 1.0 | 15.8 |
| C5A_09 | F241L/V264E/T307P/A378V/N434S | 4.8 | 0.2 | 15.2 |
| T6A_22 | P230T/V264E/S403T/N434S | 4.7 | 0.9 | 15.2 |
| T5A_81 | V264E/A378V/R416K | 4.6 | 1.0 | 14.9 |
| C6A_12 | P230T/N315D/Q362E/N434Y | 4.6 | 0.6 | 14.9 |
| C4A_14 | C226G/N315D/N434Y | 4.6 | 0.8 | 14.8 |
| T4A_42 | C226G/N315D/Q362R/N434Y | 4.6 | 0.4 | 14.7 |
| T5A_25 | C226G/V264E/Q347R/K370R/A378V/ N4345 | 4.6 | 0.2 | 14.7 |
| T4A_48 | V308I/N315D/A330V/E382V/N434Y | 4.5 | 0.7 | 14.5 |
| C6A_48 | P230T/V264E/A378V/N434S | 4.5 | 0.8 | 14.4 |
| T5A_45 | A231T/F241L/V264E/A378T/V397M/ N4345 | 4.5 | 0.6 | 14.3 |
| T6A_23 | P230L/V264E/A378V/N434S | 4.4 | 0.7 | 14.1 |
| C5A_65 | P230T/N315D/A330V/Q386K/N434Y | 4.2 | 0.5 | 13.5 |
| C6A_88 | C226G/N315D/A330V/N389T/N434Y | 4.2 | 0.4 | 13.4 |
| C4A_13 | S267R/T307P/A378V/N421T/N434Y | 4.1 | 0.3 | 13.2 |
| C3A_35 | P230S/N315D/P387T/N434Y | 4.0 | 0.7 | 12.9 |
| T4A_37 | P230S/V264E/P352S/A378V/N434S | 4.0 | 0.5 | 12.8 |
| 55A_41 | P230T/V303A/K322R/N389T/F404L/ N4345 | 3.9 | 0.6 | 12.4 |
| C6A_78D | P228R/T256N/A378V/N434Y | 28.3 | 6.7 | 90.5 |
| T5A_74D | P228R/N315D/A330V/N361D/A378V/ N434Y | 26.0 | 5.8 | 83.1 |
| C6A_74D | P228R/V259I/N315D/N434Y | 18.6 | 4.6 | 59.7 |
| T5A_74F | P228R/P2305/N315D/A330V/N361D/ A378V/N434Y | 16.8 | 5.5 | 53.8 |
| C6A_78B | P228L/T256N/A378V/N434Y | 14.4 | 1.9 | 45.9 |
| C6A_69G | P228R/P2305/T307A/N315D/A330V/ E382V/N389T/N434Y | 11.9 | 4.2 | 38.2 |
| C6A_74C | P228L/V259I/N315D/N434Y | 11.0 | 2.8 | 35.3 |
| C6A_69E | P228R/T307A/N315D/A330V/E382V/ N389T/N434Y | 10.0 | 2.8 | 32.0 |
| C6A_78F | P228R/P230S/T256N/A378V/N434Y | 9.4 | 1.8 | 30.1 |
| C6A_78C | P230S/T256N/A378V/N434Y | 9.2 | 2.4 | 29.4 |
| C6A_78A | T256N/A378V/N434Y | 8.7 | 1.0 | 27.8 |
| C6A_74E | P228L/P230S/V259I/N315D/N434Y | 8.6 | 2.7 | 27.5 |
| C6A_60B | P228R/N315D/M428L/N434Y | 8.6 | 3.9 | 27.4 |
| C6A_69C | P230S/T307A/N315D/A330V/E382V/ N389T/N434Y | 8.4 | 1.3 | 26.8 |
| C6A_69F | P228L/P230S/T307A/N315D/A330V/ E382V/N389T/N434Y | 8.2 | 3.1 | 26.3 |
| T5A_74C | P228L/N315D/A330V/N361D/A378V/ N434Y | 7.5 | 1.3 | 24.0 |
| C6A_60D | P228R/P230S/N315D/M428L/N434Y | 7.4 | 1.4 | 23.8 |
| C6A_74F | P228R/P230S/V259I/N315D/N434Y | 7.3 | 1.9 | 23.2 |
| T5A_74E | P228L/P230S/N315D/A330V/N361D/ A378V/N434Y | 7.1 | 2.0 | 22.6 |
| C6A_78E | P228L/P230S/T256N/A378V/N434Y | 6.0 | 0.4 | 19.1 |
| C6A_74A | P230S/V259I/N315D/N434Y | 6.0 | 1.0 | 19.0 |
| T5A_74B | P230S/N315D/A330V/N361D/A378V/ N434Y | 5.9 | 1.0 | 18.8 |
| C6A_60C | P228L/P230S/N315D/M428L/N434Y | 5.3 | 1.9 | 17.1 |
| C6A_69D | P228L/T307A/N315D/A330V/E382V/ N389T/N434Y | 4.8 | 1.0 | 15.3 |
| C6A_60A | P228L/N315D/M428L/N434Y | 2.4 | 1.0 | 7.7 |

III. E. Coli Expression of the Fc Variants

The Fc-WT sequence as well as the Fc-H variant and Fc variants isolated during MS1 and MS2 were subcloned from the pMG58 phagemid vector into the pMG62 vector, using BamHI and EcoRI restriction sites, permitting soluble periplasmic expression with a C-terminal 6×His tag for purification and a V5 tag for detection in ELISA assays. Production of recombinant Fc polypeptides was performed in HB2151 E. coli strain (induction with 0.5 mM IPTG for 16 hours at 20° C.). Purification was performed on Ni-NTA using standard protocols and around 200-504 μg of each polypeptide were obtained.

IV. FcRn Binding Characterisation of the Fc Variants Using ELISA and Surface Plasmon Resonance (SPR)

IV.1. FcRn Binding Characterization of S5A_41, S3A_07 and Fc-H variants as compared to Fc_WT IV.1.a. ELISA Assays The binding characteristics of the Fc variants produced in a soluble format were determined in comparison with the Fc-WT using an ELISA test at pH6.0 with FcRn-p3 coated on wells. Purified Fc variants (as described in III) serially diluted in P6/5% skimmed milk/0.1% Tween-20 were tested on Maxisorp immunoplates previously coated with 0.25 μg FcRn-p3/well and blocked with 5% skimmed milk in P6. After incubation for 2 hours at 37° C., wells were washed 3 times with P6/0.1% Tween-20 and bound Fc-variants were detected with an HRP anti-V5 antibody (invitroGen) (measurement of OD450 nm) (FIG. 5a). ELISA test was performed on S5A_41, the best variant of MS1, and S3A_07, a variant equivalent to Fc-H variant, and Fc-H variant. These ELISA tests confirmed that Fc-H, S5A_41 and S3A_07 had improved binding to FcRn compared with the Fc-WT (FIG. 5b, FIG. 5c and FIG. 5d). For each binding curve, the measurement of Fc concentration at 50% saturation of the curve (EC50) was used to characterise the binding properties of the Fc variants compared to Fc-WT. The ratios thereby obtained confirmed that the S5A_41 is a better binder than Fc-H variant and S3A_07 is equivalent to Fc-H variant (Table 6).

IV.1.b. SPR (Surface Plasmon Resonance) Assays

The interaction of Fc variants with immobilized FcRn was monitored performed on a BIAcore X100 instrument using a CM5 sensor chip (Biacore, GE Healthcare). The methodology was similar to that previously described for analyzing Fc-FcRn interactions (Popov S. et al., Mol Immunol. 33 (6): 521-530 (1996)). Recombinant soluble FcRn was coupled to flow cell 2 of the sensor chip using amine-coupling chemistry. The flow cells were activated for 3 min with a 1:1 mixture of 0.1 M N-hydroxysuccinimide and 0.1 M 3-(N,N-dimethylamino)propyl-N-ethylcarbodiimide at a flow rate of 30 μl/min. Recombinant human FcRn (5 μg/ml in 10 mM sodium acetate, pH 5.0) was injected over flow cell 2 for 8 min at 10 μl/min, which resulted in a surface density of 1200 to 1300 response units (RU). Surfaces were blocked with a 3-min injection of 1 M ethanolamine-HCl, pH 8.5. Flow cell 1 was used as a control surface without FcRn and was prepared similarly to sample flow cell. The data from this blank flow cell were subtracted from the sample data.

Fc fragments were diluted in PBS/Tween-20 (50 mM phosphate buffer, pH 6.0, 150 mM NaCl, 0.02% $NaN_3$, 0.01% Tween-20) which is used as running buffer in equilibrium binding experiments. All measurements were performed at 25° C. with Fc fragment concentrations typically ranging from 1 to 200 nM at a flow rate of 10 μl/min.

Data were collected for 10 min and 1-min pulse of PBS, pH 8 containing 0.05% Tween-20 was used to regenerate the surfaces.

Sensorgrams were generated and analyzed by using BIAevaluation software version 3.1. The equilibrium RU observed for each injection was plotted against the concentration of Fc. The equilibrium Kd values were derived by analysis of the plots by using the steady-state affinity model included in the BIAevaluation software.

The Kd ratios thereby obtained confirmed that the S5A_41 is a better binder than Fc-H variant and S3A_07 is equivalent to Fc-H (Table 6).

IV.1.c. Summary of the Obtained Results

The table 6 hereunder shows FcRn binding characterization of variants S5A_41, S3A_07 and Fc-H as compared to Fc_WT by (i) phage ELISA, (ii) ELISA and (iii) SPR. In all cases, variant S5A_41 displayed a significantly higher capacity to bind FcRn than Fc_WT.

TABLE 6

FcRn binding characterisation of the Fc variants using ELISA and Surface Plasmon Resonance (SPR). For phage-ELISA and Fc-rec-ELISA, the ratio refer to Variant specific signal divided by Fc-WT specific signal. For SPR, the ratio refers to Fc-WT Kd divided by Variant Kd.

| Fc variants | phage-ELISA Ratio/Fc-WT | Fc-rec-ELISA Ratio/WT | SPR Ratio/Fc-WT |
|---|---|---|---|
| Fc-WT | 1.0 | 1.0 | 1.0 |
| Fc-H | 3.2 | 27.1 | 7.6 |
| S3A_07 | 3.5 | 25.3 | 5.2 |
| S5A_41 | 9.0 | 66.3 | 10.7 |

IV.2. FcRn Binding Characterization of Other MS2 Variants as Compared to Fc_WT by SPR and ELISA Several Fc variants of MS2 were produced as described above in part III. The ability of each variant to bind FcRn was assayed by (i) SPR and by (ii) ELISA as described above in part IV.2.b and in part IV.2.c, respectively.

Several results are shown in FIG. 7.

Table 7 hereunder shows the results obtained for each MS2 variant tested by (i) SPR and (ii) ELISA. The previous results obtained by ELISA-phage are also indicated.

ELISA and SPR assays showed that all Fc variants are better binder than wild-type Fc for FcRn, which correlated with the results previously obtained by ELISA assays on phage-Fc variants.

The Kd values of the MS2 variants at pH=6 ranged from 5.2 to 22.7 nM, which corresponds to an increase in affinity of 1.3 to 5.8 fold as compared to Fc-WT.

TABLE 7

FcRn binding characterization of the Fc variants using ELISA and Surface Plasmon Resonance (SPR). For phage-ELISA, the ratio refers to variant specific signal divided by Fc-WT specific signal. For ELISA, the ratio refers to Fc-WT EC50 divided by variant EC50. For SPR, the ratio refers to Fc-WT Kd divided by variant Kd.

| | phage- | ELISA on Fc-recombinant variants | | SPR | |
|---|---|---|---|---|---|
| Name of clone | ELISA ratio/WT | EC50 (nm) | ratio/ Fc-WT | $K_d$ (nM) at pH = 6 | Ratio/ Fc-WT |
| Fc-WT | 1.0 | 461.2 | 1 | 30.2 | 1 |
| Fc-H | 3.2 | 16.6 | 28 | 10.7 | 2.8 |
| C6A_60 | 26.8 | 2.6 | 177 | 5.2 | 5.8 |
| C6A_74 | 27.2 | 7.3 | 63 | 5.9 | 5.2 |
| C6A_78 | 27.8 | 4.7 | 97 | 5.8 | 5.2 |
| C6A_69 | 28.4 | 3.7 | 124 | 7.2 | 4.2 |
| T5A_74 | 27.6 | 5.5 | 85 | 7.1 | 4.2 |
| C6A_66 | 24.6 | 4.9 | 95 | 9.7 | 3.1 |
| C6A_72 | 25.7 | 7.8 | 59 | 12.4 | 2.4 |
| T5A_78 | 25.6 | 4.7 | 97 | 12.4 | 2.4 |
| 55A_41 | 9.0 | 9.0 | 51 | 13.9 | 2.2 |

TABLE 7-continued

FcRn binding characterization of the Fc variants using ELISA and Surface Plasmon Resonance (SPR). For phage-ELISA, the ratio refers to variant specific signal divided by Fc-WT specific signal. For ELISA, the ratio refers to Fc-WT EC50 divided by variant EC50. For SPR, the ratio refers to Fc-WT Kd divided by variant Kd.

| | phage- | ELISA on Fc-recombinant variants | | SPR | |
|---|---|---|---|---|---|
| Name of clone | ELISA ratio/WT | EC50 (nm) | ratio/ Fc-WT | $K_d$ (nM) at pH = 6 | Ratio/ Fc-WT |
| T5A_94 | 18.5 | 166.0 | 3 | 13.7 | 2.2 |
| T5A_58 | 26.1 | 9.8 | 47 | 15.4 | 2.0 |
| T5A_81 | 14.9 | 144.8 | 3 | 22.7 | 1.3 |

The capacity of the Fc variants to bind FcRn at different pHs was also assessed by ELISA assay.

For each Fc variant previously tested, ELISA assays were performed at a concentration providing an OD450 nm ranging from 0.8 and 1.0 when performing the ELISA assay at pH=6. The experimental conditions are those described previously in part IV.1.a. Table 8 hereunder indicates the concentration of each Fc variant used for performing ELISA assays.

TABLE 8

Concentration of each Fc variant used to show the distinct binding affinities to FcRn at different pHs.

| | Fc Concentration (nM) |
|---|---|
| Fc-WT | 200.0 |
| Fc-H | 6.2 |
| C6A_69 | 1.2 |
| T5A_74 | 1.2 |
| C6A_60 | 1.2 |
| S5A_41 | 2.0 |
| C6A_78 | 2.5 |
| C6A_74 | 5.0 |
| C6A_72 | 5.0 |
| T5A_78 | 12.5 |
| C6A_66 | 20.0 |
| T5A_58 | 50.0 |

FIG. 7 shows the results of ELISA assays obtained for each variant. $OD_{450\ nm}$ correlates with the amount of Fc variants bound to immobilized FcRn (detection of bound Fc variants with HRP anti-V5 antibody). The higher the specific signal at $OD_{450\ nm}$ was, the higher the binding of the Fc-variant to FcRn was.

FIG. 7 clearly shows that the binding of Fc variants with FcRn varies upon pH. As expected, the binding of Fc variants to FcRn at pH 7.4 is insignificant as compared to the binding at pH 6.0.

It may be concluded that the amino acid modifications introduced to obtain Fc variants of the present invention may significantly increase the binding to FcRn at pH 6.0 as compared to that of Fc-WT but may not significantly modify the binding at pH 7.4 which remains very low.

Example 2

Production of IgG Variants Based on Fc Variants and Biological Characterization of Said IgG I. Expression of the IgG Variants I.1. Vector Construction The Fc variants C6A_69; C6A_78; T5A_74; C6A_74; C6A_60 and C6-A66 were prepared in a IgG format with an anti-CD20 specificity in YB2/0 cell line. For comparative purpose, IgG based on wild-type Fc (IgG-WT) was also produced.

In order to maximize productivity in the YB2/0 cell line, the full length heavy and light chains cDNA as well as Fc fragment coding the variants were neo-synthesized with codon optimisation for Rattus norvegicus. Unwanted features such as cryptic splicing sites or restriction sites were removed. Only a restriction site (ApaI) was present at the junction variable/constant region.

In a first step, wild-type heavy chain was cloned between NheI and AscI in the expression vector CHK622-08, optimized for expression in YB2/0, resulting in the intermediate construct HCD20-Opti-GA. The optimized light chain was then cloned between SpeI and XbaI restriction sites resulting in the final construct HKCD20-Opti-GA for expression of the wild-type anti-CD20 antibody (named IgG-WT hereunder).

Fc variants were prepared by replacing the wild IgG1 Fc fragment present in HKCD20-Opti-GA by its appropriated version. This was cloned between ApaI and AscI restriction sites (FIG. 8a).

Every fragment cloning was done by classical digestion/ligation procedures, prior bacterial transformation. Expression constructs were screened by enzymatic digestion plus PCR and validated by sequencing.

I.2. Cell Culture Production $5 \cdot 10^6$ cells of the YB2/0 cell line (ATCC, CRL-1662) were electroporated with each expression linearised vector, then diluted at 25,000 cells/mL in RPMI 1640 medium+5% v/v dialysed FCS (InvitroGen) and dispensed under 1 mL/well in 24-well plates. After 3 days of cell recovery, selection pressure was applied by adding concentrated geneticin (Invitrogen) at 0.5 g/L final and concentrated methotrexate (Sigma) at 25 mM final, 2 mL/well. After 11 days of incubation, resistant cells were pooled for each of the 8 constructs (encoding for the selected IgG MS2 variants, and IgG-WT) and progressively diluted with DMEM medium+5% v/v Ultra-low IgG FCS (InvitroGen) until two (2) 2 L-roller bottles containing 0.9 L of cell suspension each can be incubated at 2 rotation/minute. Cells were allowed to grow and die (4 to 5 days) before supernatant collection, clarification by low-speed centrifugation and volume reduction by ultra-filtration on Pellicon XL Filter (Millipore).

II. Purification and Characterisation of IgG Variants

The concentrated culture supernatants were injected into a HiTrap protein A FF column (GE Healthcare). Bound antibodies were eluted with sodium citrate buffer 0.1 M, pH 3.0 and fractions were neutralized using 100 μl of 1 M Tris pH 7.5 per ml of elution buffer. Fractions containing the antibodies were pooled and dialyzed into PBS pH 6.0, and the samples were sterile-filtered (0.22 nm) and stored at 4° C.

The purified IgGs were characterised by SDS-PAGE under non-reducing and reducing conditions. Coomassie Blue-stained gels indicated that the IgGs, whatever the mutations, were purified to greater than 95% homogeneity and displayed the characteristic heavy and light chain bands for each IgG (FIG. 8b and FIG. 8c).

III. FcRn Binding Characterisation of the IgG Variants

The binding properties of IgG variants to FcRn were determined by three distinct tests: (i) by ELISA assay, (ii) by SPR and (iii) by a competition binding assay performed on Jurkat-cell line expressing a truncated FcRn in the presence of fluorescent-labelled Rituximab (an anti-CD20 IgG)

III.1. ELISA

III.1.a. Material and Method

The binding properties of the IgG variants produced in Y2B/O were determined using an ELISA test at pH6.0 with FcRn-p3 coated on wells. For comparative purpose, ELISA assay was also performed on IgG-WT Purified IgG variants serially diluted in P6/5% skimmed milk/0.1% Tween-20 were tested on Maxisorp immunoplates previously coated with 0.1 μg FcRn-p3/well and blocked with 5% skimmed milk in P6. After incubation for 2 hours at 37° C., wells were washed 3 times with P6/0.1% Tween-20 and bound IgG variants were detected with an HRP Fab'2 goat anti-human Fab'2 (Interchim).

For each IgG variants, the percentage of bound FcRn was plotted versus the log of the concentration of IgG-variant. For each resulting binding curve, the measurement of the IgG concentration related to 50% saturation of the curve (EC50) was determined and compared to the EC50 of WT-IgG.

III.1.b. ELISA Results

The ELISA tests showed that the produced IgG variants had an increased binding to FcRn as compared to that of WT-IgG. This fact is clearly illustrated by binding curves (see FIG. 9) and by EC50 values.

As illustrated in table 9 hereunder, the EC50 of IgG-variants are at least 5.8-fold lower than that of wild-type IgG. The best EC50 is obtained for C6A_69 variant.

TABLE 9

Concentration at 50% saturation (EC50) obtained from the ELISA binding curve of each IgG variant. The ratio refers to WT EC50 divided by variant EC50.

| IgG Variants | EC50 (ng/ml) | Ratio variant/WT |
|---|---|---|
| WT | 11060 | 1.0 |
| C6A_69 | 1021.6 | 10.8 |
| C6A_78 | 1440.9 | 7.7 |
| T5A_74 | 1191.8 | 9.3 |
| C6A_74 | 2116.0 | 5.2 |
| C6A_60 | 1904.0 | 5.8 |
| C6A_66 | 1900.4 | 5.8 |

111.2. IgG/FcRn Binding Affinity Measurements with SPR

III.2.a. Material and Method

The interaction of IgG-WT and IgG variants with recombinant, immobilized human-FcRn was monitored by surface plasmon resonance (SPR) detection using a BIAcore X100 instrument (GE Healthcare). The experimental protocol was similar to that used for determining the affinity of Fc variants (see paragraph IV.2.b. above).

The equilibrium RU observed for each injection was plotted against the concentration of Fc. The equilibrium Kd values were derived by analysis of the plots by using the steady-state affinity model included in the BIAevaluation software. Kinetic parameters were determined by global fitting of association and dissociation phase data with a model 1:2.

III.2.b. SPR Results

The binding affinity (Kd values) of the IgG-WT for human FcRn was 78.3 nM. As illustrated in table 10, The Kd values of the 6 IgG variants were ranged from 10.5 to 18.8 nM which showed an increase in affinity for FcRn at pH 6.0 of 4 to 7 fold as compared to that of IgG-WT.

TABLE 10

Kd values obtained by SPR. The ratio refers to WT-Kd divided by variant Kd. In order to determine the kinetic parameters, datasets for the interaction of the IgG WT and variants with human FcRn were fit with 1:2 model included in the BIAevaluation software. The curves obtained with IgG WT didn't fit with the 1:2 model whereas the curves obtained with the IgG variant C6A_66 and all other variants fit well with the model 1:2 (data not shown).

| | $K_d$(nM) | Ratio WT/variant |
|---|---|---|
| WT | 78.27 | 1 |
| C6A_69 | 18.77 | 4 |
| C6A_78 | 17.64 | 4 |
| T5 A_74 | 10.55 | 7 |
| C6 A_74 | 12.87 | 6 |
| C6 A_60 | 13.79 | 6 |
| C6 A_66 | 15.18 | 5 |

As illustrated in table 11 hereunder, the enhanced affinity of the IgG variants for human FcRn relative to the WT were predominantly driven by increased association kinetics (kon values). Thus, the ratio that refer to variants kon divided by WT-kon ranged from 13 to 23, indicating a significant increase in affinity of variants to FcRn. The increased values of Koff of the IgG variants relative to WT were ranged from 2 to 4, displaying a faint impact of the dissociation as compared to the association.

TABLE 11

Rates of dissociation (koff) and association (kon) determined by SPR

| | $k_{on}$ ($\times 10^5$) | $k_{off}$(1/s) | $K_D$ (nM) |
|---|---|---|---|
| WT | 0.36 | 0.00355 | 99 |
| C6A_69 | 7.60 | 0.00837 | 11 |
| C6A_78 | 8.19 | 0.00981 | 12 |
| T5A_74 | 5.22 | 0.00885 | 17 |
| C6A_74 | 5.81 | 0.01349 | 23 |
| C6A_60 | 8.12 | 0.00788 | 9.7 |
| C6A_66 | 4.83 | 0.01264 | 26 |

III.3. Binding to Jurkat-FcRn

III.3.a. Material and Method

Competition immunofluorescence assays were performed to evaluate the ability of IgG WT and variants to interact with FcRn by a method adapted from that described by Dall'Ozzo et al. (Dall'Ozzo S, Tartas S, Paintaud G, Cartron G, Colombat P, Bardos P, Watier H, Thibault G, Cancer Res., 2004 Jul. 1; 64(13):4664-9).

Briefly, IgG WT and variants were diluted in PBS pH6 at a final concentration ranging from 0.06 to 2 mg/ml and incubated with Jurkat FcRn (150000 cell) in the presence of Alexa-conjugated Rituximab (labelled Rituximab) at a concentration of 50 μg/ml. After 20 minutes, the cells were analyzed by flow cytometry in order to quantify Alexa-Rituximab binding. The results were expressed as a percentage of the mean fluorescence intensity (MFI), 100% refers to the mean fluorescence intensity (MFI) obtained with Alexa-conjugated Rituximab alone (i.e. without competitor) and 0% refers to the MFI value measured when Jurkat FcRn was not incubated with Alexa conjugated Rituximab. Each experiment was done in triplicate.

Controls comprise the incubation of (i) unlabelled Rituximab or (ii) IgG-WT.

For each tested IgG, the MFI was plotted versus the log of IgG concentration. The concentration (IC50) of each tested IgG which provides an inhibition of 50% of the MFI signal was determined.

A general description of this assay may also be found in the French patent application published as FR 2 894 983.

III.3.b. Experimental Results

Several results are shown in FIG. 11 where the binding or Ritixan and of various variants according to the invention to Jurkat FcRn has been determined as described in the Materials and Methods Section above and expressed as mean fluorescence intensity (MFI) values.

As illustrated in table 12 hereunder, the IC50 obtained for the variants of the invention are significantly lower than that obtained for WT-IgG. The decrease in IC50 for IgG variants of the invention was from 40 to 60-fold except for C6A_66.

TABLE 12

IC50 obtained for binding competition assay performed on Jurkat cells expressing FcRn in the presence of fluorescent-labelled Rituximab. The "50% RTX = 1" values consist of IC50 values that are also expressed μg/ml.

| | IC50 (μg/ml) | 50% RTX = 1 |
|---|---|---|
| Rituximab | NA | ≠1 |
| WT | 219 | 5 |
| C6A_69 | 4 | 240 |
| C6A_78 | 4 | 275 |
| T5A_74 | 4 | 224 |
| C6A_74 | 5 | 200 |
| C6A_60 | 3 | 234 |
| C6A_66 | 21 | 48 |

III.4. Conclusion

The three distinct tests performed to characterize the binding properties of IgG variants to FcRn provided consistent results. In all case, IgG variants of the invention displayed a significant increased binding to FcRn as compared to that of IgG wild type.

IV. Functional Characterisation IgG Variants and Comparison with IgG-WT and LFB-R603

The ability of IgG variants to bind Fcγ receptors and their ADCC and CDC activities were assessed in order to fully-characterize their biological functions.

IV.1. Binding of I IgG Variants Binding to hFcγRIIIA

IV.1.a. ELISA Assay: Binding of IgG Variant to Immobilized Recombinant hFcγRIIIA The human recombinant FcγRIIIA (F158 allotype) was biotinylated with EZ-link NHS-PEO kit (Pierce), diluted at 1 μg/ml in assay buffer (Tris 25 mM, NaCl 150 mM, pH 7.35, 0.05% Tween-20, 0.1% BSA) and coated onto React-Bind™ streptavidin ELISA plates (Pierce) for 2 h at room temperature. During this incubation time, IgG-F(ab')2 anti-F(ab')2 complexes were prepared in assay buffer by mixing 5 μg/ml of IgG and 2 μg/ml F(ab')2 anti-human F(ab')2 labelled with horseradish peroxidase (Jackson ImmunoResearch) for 2 h at room temperature. Serial dilutions of complexes were added to plates and incubated for 2 h at room temperature under gentle shaking. After washing plates with assay buffer, bound complexes to hFcγRIIIA were detected with TMB (Pierce). Absorbance at 450 nm was read using a plate reader (Tecan).

For each IgG variants, the percentage of bound FcγRIIIA (which is obtained from OD450 nm) was plotted versus the concentration of IgG-variant.

As shown in FIG. 10, the binding of IgG variants to hFcγRIIIA is similar to that of the IgG WT, except for variant C6A_66 which fails to bind hFcγRIIIA.

IV.2. ADCC Activity

The natural killer (NK cells) cells were purified from the peripheral blood of healthy donors by the negative depletion technique developed by the company Miltenyi. The ADCC test comprises incubating the NK cells with the target cells of the Raji line that express the CD20 receptor, in the presence of different concentrations of anti-CD20 antibodies. After 16 hours of incubation, the cytotoxicity induced by the anti-CD20 antibodies is chromogenically measured by quantifying in cell supernatants the level of an intracellular enzyme called lactate dehydrogenase (LDH) which is released by the lysed target cells. The results are shown in FIG. 12.

The specific lysis results are expressed as the percent lysis as a function of antibody concentration. EC50 (quantity of antibody that induces 50% of maximum lysis) were calculated using PRISM software. Control experiments were performed with (i) Rituximab, (ii) WT-IgG produced in Y2/0 cells and LFB-R603 which is an anti-CD20 antibody known to have ADDC function that has been described by de Romeuf et al. in 2004 (de Romeuf C, Dutertre C A, Le Garff-Tavernier M, Fournier N, Gaucher C, Glacet A, Jorieux S, Bihoreau N, Behrens C K, Béliard R, Vieillard V, Cazin B, Bourel D, Prost J F, Teillaud J L, Merle-Béral H. Chronic lymphocytic leukaemia cells are efficiently killed by an anti-CD20 monoclonal antibody selected for improved engagement of FcgammaRIIIA/CD16. Br J Haematol. 2008 March; 140(6):635-43). as well as in the PCT application no WO 2006/064121.

Table 13 hereunder shows the EC50 for each variant and compares the ADCC function of IgG variants with that of LFB-R603 and WT-IgG.

All IgG variants display ADCC activity except C6A_66 variant. This variant has no ADCC activity which is consistent with its very low affinity for FcγRIII.

It should be noticed that C6A_69, C6A_60 and C6A_74 have an increased ADCC activity as compared to IgG-WT. The other variants (namely C6A_78 and T5A_75) have an ADCC activity similar to that of IgG-WT.

TABLE 13

EC50 (quantity of antibody that induces 50% of maximum lysis) obtained from ADCC assay. The ratio refers variant EC50 divided by LFB-R603 EC50.

| | EC50 (μg/ml) | Ratio R603/Variant |
|---|---|---|
| LFB-R603 | 0.2 | 1.0 |
| Rituximab | >5000 | N.A. |
| WT | 1.2 | 6.0 |
| C6A_69 | 0.5 | 2.3 |
| C6A_78 | 1.0 | 4.7 |
| T5A_74 | 0.7 | 3.3 |
| C6A_74 | 0.2 | 0.9 |
| C6A_60 | 0.3 | 1.6 |
| C6A_66 | >5000 | N.A. |

IV.3. CDC Activity

In this technique, the target CD20+ cells of the Raji line were incubated with different concentrations of anti-CD20 antibodies (0 to 5000 ng/ml) in the presence of baby rabbit serum as a source of complement (Cedarlane ref.: CL3441, dilution to 1/10). After 1 hour of incubation at 37° C., the quantity of LDH released in the supernatant by the lysed target cells is measured chromogenically (Roche Applied Sciences Cytotoxicity Detection Kit) and is used to quantity the complement-dependent cytotoxicity mediated by the antibodies. The results are expressed as a percentage of lysis. EC50 (quantity of antibody that induces 50% of maximum lysis) and Emax (percentage of maximum lysis) were calculated using PRISM software.

Table 14 hereunder shows the Emax and EC50 obtained for each variant.

The level of CDC activity varies upon IgG variants.

C6A_78 and C6A_60 have a CDC activity significantly higher that of IgG-WT whereas C6A_69, T5_74 and C6A_66 display low CDC activity.

The CDC activity of C6A_74 variant is similar to that of IgG-WT.

TABLE 14

EC50 (quantity of antibody that induces 50% of maximum lysis) obtained from CDC assay.

| | Emax (lysis %) | EC50 (ng/ml) |
|---|---|---|
| LFB-R603 | 61.87 | 514.0 |
| Rituximab | 65.60 | 419.0 |
| WT | 57.32 | 541.1 |
| C6A_69 | N.A. | >5000 |
| C6A_78 | 75.99 | 117.3 |
| T5A_74 | N.A. | >5000 |
| C6A_74 | 59.90 | 458.4 |
| C6A_60 | 77.22 | 92.66 |
| C6A_66 | 10.28 | 935.1 |

IV.3. Conclusion

The six IgG variants of the invention recombinantly produced in Y2B/0 cell line have an increased binding to FcRn receptor as compared to the IgG-WT (produced in the same host cell and in the same condition).

IgG variants of the invention have at least the same binding affinity to FcgRIII and the at least the same ADCC activity than IgG-WT, except C6AA_66 which shows poor affinity for FcgRIII.

The IgG variants display distinct CDC activities.

To conclude, in some aspects, amino acid modifications according to the invention enable to obtain IgG variants which have an increased binding for FcRn combined with one or more Fc effector activities which are at least similar to that of the corresponding parent IgG (i.e IgG-WT).

In other aspect, amino acid modifications according to the invention enable to obtain IgG variants which have an increased binding for FcRn combined with at least one decreased Fc effector activity such as CDC or ADCC.

Table 15 hereunder shows the main conclusions concerning IgG variants of the present study.

TABLE 15

Main results obtained for the IgG variants of the invention as compared to IgG-WT;

| Variant | Mutations | Liaison FcRn | ADCC | CDC |
|---|---|---|---|---|
| C6A_69 | T307A/N315D/A330V/E382V/N389T/N434Y | ++ | ↗ | ↘ |
| C6A_78 | T256N/A378V/S383N/N434Y | ++ | ✓ | ↗ |
| T5A_74 | N315D/A330V/N361D/A378V/N434Y | ++ | ✓ | ↘ |
| C6A_74 | V259I/N315D/N434Y | ++ | ↗ | ✓ |
| C6A_60 | P230S/N315D/M428L/N434Y | ++ | ↗ | ↗ |
| C6A_66 | E294del/T307P/N434Y | ++ | ↘ | ↘ |

++: Increased binding to FcRn as compared to WT-IgG;

↗: Increased activity as compared to WT-IgG;

↘: Decreased activity as compared to WT-IgG;

✓: Activity similar to that of WT-IgG

TABLE 7

| Sequences included in the sequence listing | |
|---|---|
| SEQ ID NO: | Sequences |
| 1 | Human IgG1 Fc (residues 226-447 according to EU index as Kabat) |
| 2 | Human IgG2 Fc |
| 3 | Human IgG3 Fc |
| 4 | Human IgG4 Fc |
| 5 | Primer |
| 6 | Primer |
| 7 | Primer |
| 8 | Primer |

TABLE 7-continued

| Sequences included in the sequence listing | |
|---|---|
| SEQ ID NO: | Sequences |
| 9 | Primer |
| 10 | Primer |
| 11 | Primer |
| 12 | Fragment of heavy chain of human IgG1 Glm1,17 allotype |
| 13 | Fragment of heavy chain of human IgG1 Glm3 allotype |
| 14 | Fragment of the heavy chain of human IgG2 |
| 15 | Fragment of the heavy chain of human IgG3 |
| 16 | Fragment of the heavy chain of human IgG4 |

SEQUENCE LISTING

```
<160> NUMBER OF SEQ ID NOS: 16

<210> SEQ ID NO 1
<211> LENGTH: 222
<212> TYPE: PRT
<213> ORGANISM: Homo sapiens
<220> FEATURE:
<221> NAME/KEY: MISC_FEATURE
<222> LOCATION: (131)..(131)
<223> OTHER INFORMATION: For G1m1,17 allotype, X is D
<220> FEATURE:
<221> NAME/KEY: MISC_FEATURE
<222> LOCATION: (131)..(131)
<223> OTHER INFORMATION: For G1m3 allotype, X is E
<220> FEATURE:
<221> NAME/KEY: MISC_FEATURE
<222> LOCATION: (133)..(133)
<223> OTHER INFORMATION: For G1m1,17 allotype, X is L
<220> FEATURE:
<221> NAME/KEY: MISC_FEATURE
<222> LOCATION: (133)..(133)
<223> OTHER INFORMATION: For G1m3 allotype, X is M

<400> SEQUENCE: 1

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Xaa Glu Xaa Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190
```

```
Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220


<210> SEQ ID NO 2
<211> LENGTH: 221
<212> TYPE: PRT
<213> ORGANISM: Homo sapiens

<400> SEQUENCE: 2

Cys Pro Pro Cys Pro Ala Pro Pro Val Ala Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Tyr Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Ala Leu Pro Ala Pro Ile Glu Lys Thr Ile Ser Lys
            100                 105                 110

Thr Lys Gly Gln Pro Arg Glu Pro Gln Val Tyr Thr Leu Pro Pro Ser
        115                 120                 125

Arg Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Met Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Lys
    210                 215                 220


<210> SEQ ID NO 3
<211> LENGTH: 222
<212> TYPE: PRT
<213> ORGANISM: Homo sapiens

<400> SEQUENCE: 3

Cys Pro Arg Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Gln Phe Lys Trp Tyr Val Asp Gly Val Glu Val His Asn Ala Lys Thr
    50                  55                  60

Lys Pro Arg Glu Glu Gln Tyr Asn Ser Thr Phe Arg Val Val Ser Val
65                  70                  75                  80
```

```
Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Thr Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Ser Gly
145                 150                 155                 160

Gln Pro Glu Asn Asn Tyr Asn Thr Thr Pro Pro Met Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Ile Phe Ser Cys Ser Val Met His Glu Ala Leu His
        195                 200                 205

Asn Arg Phe Thr Gln Lys Ser Leu Ser Leu Ser Pro Gly Lys
    210                 215                 220


<210> SEQ ID NO 4
<211> LENGTH: 221
<212> TYPE: PRT
<213> ORGANISM: Homo sapiens

<400> SEQUENCE: 4

Cys Pro Ser Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Met Glu Val His Asn Ala Lys Thr Lys
    50                  55                  60

Pro Arg Glu Glu Gln Phe Asn Ser Thr Phe Arg Val Val Ser Val Leu
65                  70                  75                  80

Thr Val Val His Gln Asp Trp Leu Asn Gly Lys Glu Tyr Lys Cys Lys
                85                  90                  95

Val Ser Asn Lys Gly Leu Pro Ala Pro Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220
```

<210> SEQ ID NO 5
<211> LENGTH: 35
<212> TYPE: DNA
<213> ORGANISM: Artificial
<220> FEATURE:
<223> OTHER INFORMATION: Primer

<400> SEQUENCE: 5 agtactgact ctacctagga tcctgcccac cgtgc 35

<210> SEQ ID NO 6
<211> LENGTH: 35
<212> TYPE: DNA
<213> ORGANISM: Artificial
<220> FEATURE:
<223> OTHER INFORMATION: Primer

<400> SEQUENCE: 6 actgctcgat gtccgtacta tgcggccgcg aattc 35

<210> SEQ ID NO 7
<211> LENGTH: 18
<212> TYPE: DNA
<213> ORGANISM: Artificial
<220> FEATURE:
<223> OTHER INFORMATION: primer

<400> SEQUENCE: 7 caggaaacag ctatgacc 18

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8 tcacgtgcaa aagcagcggc 20

<210> SEQ ID NO 9
<211> LENGTH: 18
<212> TYPE: DNA
<213> ORGANISM: Artificial
<220> FEATURE:
<223> OTHER INFORMATION: Primer

<400> SEQUENCE: 9 tgattacgcc aagcttgc 18

<210> SEQ ID NO 10
<211> LENGTH: 100
<212> TYPE: DNA
<213> ORGANISM: Artificial
<220> FEATURE:
<223> OTHER INFORMATION: Primer

<400> SEQUENCE: 10 cgggatcctg cccaccgtgc ccagcacctg aactcctggg gggaccgtca gtcttcctct 60 tccccccaaa acccaaggac caactcatga tctcccggac 100

<210> SEQ ID NO 11
<211> LENGTH: 84
<212> TYPE: DNA
<213> ORGANISM: Artificial
<220> FEATURE:

<223> OTHER INFORMATION: Primer

<400> SEQUENCE: 11 gcgaattctt tacccggaga cagggagagg ctcttctgcg tgtagtggtt gtgcagagcc 60 tcatgcagca cggagcatga gaag 84

<210> SEQ ID NO 12
<211> LENGTH: 232
<212> TYPE: PRT
<213> ORGANISM: Homo sapiens

<400> SEQUENCE: 12

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 13
<211> LENGTH: 232
<212> TYPE: PRT
<213> ORGANISM: Homo sapiens

<400> SEQUENCE: 13

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val

```
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 14
<211> LENGTH: 228
<212> TYPE: PRT
<213> ORGANISM: Homo sapiens

<400> SEQUENCE: 14

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190
```

```
Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225


<210> SEQ ID NO 15
<211> LENGTH: 279
<212> TYPE: PRT
<213> ORGANISM: Homo sapiens

<400> SEQUENCE: 15

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275


<210> SEQ ID NO 16
<211> LENGTH: 228
<212> TYPE: PRT
<213> ORGANISM: Homo sapiens

<400> SEQUENCE: 16
```

-continued

```
Glu Ser Lys Tyr Gly Pro Pro Cys Pro Ser Pro Ala Pro Glu Phe Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Met Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225
```

The invention claimed is:

1. A variant of a parent polypeptide comprising a Fc region, which variant exhibits increased binding to FcRn as compared to said parent polypeptide and comprises a combination of amino acid modifications selected from the group consisting of:

N315D/A330V/N361D/A378V/N434Y,
V264E/N315D/A378V/N390S/G420R/N434Y,
N315D/A378V/N434Y,
N315D/A330V/A378V/N434Y,
N315D/K334E/A378V/N434Y,
V264E/N315D/A378V,
P228R/N315D/A330V/N361D/A378V/N434Y,
P228R/P230S/N315D/A330V/N361D/A378V/N434Y,
P228L/N315D/A330V/N361D/A378V/N434Y,
P228L/P230S/N315D/A330V/N361D/A378V/N434Y,
P230S/N315D/A330V/N361D/A378V/N434Y,
P230T/V264E/N315D/K370R/A378V, of the Fc region, wherein the numbering of the amino acids in the Fc region is that of the EU index as in Kabat.

2. The variant according to claim 1, wherein said variant is an antibody.

3. The variant according to claim 2, wherein said antibody is an IgG antibody.

4. A pharmaceutical composition comprising a variant as defined in claim 1.

5. A medicament comprising a variant according to claim 1.

6. An isolated nucleic acid encoding a variant as defined in claim 1.

7. A vector comprising the nucleic acid of claim 6.

8. An isolated host cell containing the vector of claim 7.

9. A method for producing a variant according to claim 1, comprising culturing a host cell containing a vector comprising an isolated nucleic acid encoding said variant so that the nucleic acid is expressed.

*10. A variant according to claim 1, wherein the Fc region of the parent polypeptide is SEQ ID NO: 1, SEQ ID NO: 2, SEQ ID NO: 3, or SEQ ID NO: 4.*

* * * * *